US008093043B2

(12) United States Patent
Pagano et al.

(10) Patent No.: US 8,093,043 B2
(45) Date of Patent: Jan. 10, 2012

(54) β-TRCP1, β-TRCP2 AND RSK1 OR RSK2 INHIBITORS AND METHODS FOR SENSITIZING TARGET CELLS TO APOPTOSIS

(75) Inventors: Michele Pagano, New York, NY (US); Elinor Dehan, New York, NY (US)

(73) Assignee: New York University, New York, NY (US)

( * ) Notice: Subject to any disclaimer, the term of this patent is extended or adjusted under 35 U.S.C. 154(b) by 178 days.

(21) Appl. No.: 12/478,003

(22) Filed: Jun. 4, 2009

(65) Prior Publication Data
US 2009/0318535 A1 Dec. 24, 2009

Related U.S. Application Data

(60) Provisional application No. 61/058,801, filed on Jun. 4, 2008.

(51) Int. Cl.
C12N 15/85 (2006.01)
C07H 21/02 (2006.01)
C07H 21/04 (2006.01)
A61K 48/00 (2006.01)

(52) U.S. Cl. ......... 435/325; 536/23.1; 536/24.5; 514/44
(58) Field of Classification Search .................. None
See application file for complete search history.

(56) References Cited

U.S. PATENT DOCUMENTS

| 4,946,778 | A | 8/1990 | Ladner et al. |
| 4,959,317 | A | 9/1990 | Sauer |
| 5,132,405 | A | 7/1992 | Huston et al. |
| 5,168,062 | A | 12/1992 | Stinski |
| 5,385,839 | A | 1/1995 | Stinski |
| 5,476,786 | A | 12/1995 | Huston |
| 5,554,601 | A | 9/1996 | Simpkins et al. |
| 5,580,859 | A | 12/1996 | Felgner et al. |
| 5,585,277 | A | 12/1996 | Bowie et al. |
| 5,589,466 | A | 12/1996 | Felgner et al. |
| 5,616,491 | A | 4/1997 | Mak et al. |
| 5,654,168 | A | 8/1997 | Bujard et al. |
| 5,679,582 | A | 10/1997 | Bowie et al. |
| 5,777,195 | A | 7/1998 | Fienberg et al. |
| 5,801,030 | A | 9/1998 | McVey et al. |
| 6,020,141 | A | 2/2000 | Pantoliano et al. |
| 2007/0049539 | A1 | 3/2007 | Smith et al. |
| 2007/0082884 | A1 | 4/2007 | Taunton et al. |
| 2009/0117577 | A1* | 5/2009 | Pagano .............................. 435/6 |
| 2009/0156479 | A1* | 6/2009 | Strous et al. .................... 514/12 |

FOREIGN PATENT DOCUMENTS

| CA | 2012311 A1 | 9/1990 |
| WO | 8912690 A1 | 12/1989 |
| WO | 9205263 A1 | 4/1992 |
| WO | 9421807 A2 | 9/1994 |
| WO | 9528494 A1 | 10/1995 |
| WO | 9901157 A1 | 1/1999 |
| WO | 9901158 A1 | 1/1999 |
| WO | 9901175 A1 | 1/1999 |
| WO | 9949029 A1 | 9/1999 |
| WO | 0170949 A1 | 9/2001 |
| WO | 03020722 A1 | 3/2003 |
| WO | 2009040512 A2 | 4/2009 |

OTHER PUBLICATIONS

Bormann et al., "Cloning and heterologous expression of the entire set of structural genes for nikkomycin synthesis from *Streptomyces tendae* Tu901 in *Streptomyces lividans*", J Bacteriology vol. 178, No. 4, (1996) p. 1216-1218.
Brown et al., "Mechanism of p53 degradation" Biochimica et Biophysica Acta 1332 (1997) O1-O6.
Carmell et al., "Germline transmission of RNAi in mice", Nature structural biology vol. 10, No. 2, 2003.
Huse et al., "Generation of a large combinatorial library of the immunoglobulin repertoire in phage lambda", Recearch Article 1989.
Kaplitt et al., "Expression of a functional foreign gene in adult mammalian brain following in vivo trasfer via a herpes simplex virus type 1 detective viral vector", Molecular and Cellular Neurosciences 2, 320-330 (1991).
Koike et al., "Molecular Cloning and Genomic Structure of the BetaTRCP2 Gene on Chromosome 5q35.1", Biochemical and biophysical research communications 269, 103-109 (2000).
Maoche et al., "Cloning of the gene encoding the human erythopoietin receptor", Blood, 1991, 78:2557-2563.
Needleman et al., "A General Method Applicable to the Search for Similarities in the Amino Acid Sequence of Two Proteins", J Mol Biol. (1970) 48, 443-453.
Patton et al., "Combinatorial control in ubiquitin-dependent proteolysis: don't Skp the F-box hypothesis", TIG Review 1998, vol. 14, No. 6.
Samulski et al., "A recombinant plasmid from which an infectious adeno-associated virus genome can be excised in vitro and its use to study viral replication", J of Viorology, 1987, p. 3096-3101.
Samulski et al., "Helper-Free Stocks of Recomvinant Adeno-Associated Viruses: Normal Integration Does Not Require Viral Gene Expression", Journal of Virology vol. 63, No. 9, 1989, p. 3822-3828.
Scherr et al., "Gene Silencing Mediated by Small Interfering RNAs in Mammalian Cells", Current Medicinal Chemistry, 2003, 10:245-256.
Splevak et al., "*Saccharomyces cerevisiae* cdc15 Mutants arrested at a late stage in anaphase are rescued by Xenopus cDNAs Encoding N-ras or a protein with Beta-Transducin Repeats", Molecular and Cellular Biology vol. 13, No. 8, 1993, p. 4953-4966.
Zhang et al., "Long-Distance PCR-Based Strategy for Preparing Knock-In vectors Directly from ES cell genomic DNA", BioTechniques vol. 25, No. 5, 1998.
Dehan et al., "bTrCP-and Rsk1/2-Mediated Degradation", Molecular Cell, vol. 33, 109-116, 2009.

(Continued)

Primary Examiner — Amy Bowman
(74) Attorney, Agent, or Firm — Fish & Richardson P.C.

(57) ABSTRACT

The invention relates to modulating BimEL levels (Bcl-2-Interacting Mediator of cell death, Extra Long isoform) to sensitize cancer cells to cell death or apoptosis. In certain embodiments, the invention relates to increasing BimEL levels. In certain embodiments, the invention relates to inhibitors of at least one of β-TrCP1/2 or RSK1/2 proteins that sensitize tumor cells to chemotherapy-induced death or apoptosis. Additionally, the invention relates to cancer therapies, diagnostics, and methods for identifying novel drugs or drug candidates for increasing BimEL levels.

6 Claims, 12 Drawing Sheets

OTHER PUBLICATIONS

Cote et al., "Generation of human monoclonal antibodies reactive with cellular antigens", Proc Natl Acad Sci USA vol. 80.pp. 2026-2030. (1983).

Lin et al., "Sequence of a cDNA Clone Encoding Pig Heart Mitochondrial CoA Transferase", J Biological Chemistry, vol. 267, No. 2, pp. 975-978: 1992.

Magram et al., developmental regulation of a cloned adult b-globin gene in transgenic mice, Nature vol. 315; 1985.

Villa-Komaroff et al., "A bacterial clone synthesizing proinsulin", Proc. Natl. Acad. Sci. USA 1978; 75:3727-3731.

DeBoer et al.,"The tac promoter: a functional hybrid derived from the trp and lac promoters", Proc. Natl. Acad. Sci. USA 1983; 80:21-25.

Gilbert, et al,. "Useful proteins from recombinant bacteria" in Scientific American 1980; 242:74-94.

Smith et al., "Single-step purification of polypeptides expressed in *Escherichia coli* as fusions with glutathione S-transferase", Gene, 1988; 67:31-40.

Kollias et al., Regulated expression of Human Ag-, b-, and Hybrid gb-Globin Genes in Transgenic Mice: Manipulation of the developmental expression patterns , Cell; 1986; 46:89-94.

Miller and Rosman et al., "Liposomes in the therapy of infectious diseases and cancer", Bio Techniques, 1992; 7:980-990.

Stratford-Perricaudet et al., "Widespread Long-Term Gene Transfer to Mouse Skeletal Muscles and Heart", J Clin Invest., 1992; 90:626-630.

La Salle et al., "An Adenovirus vector for gene transfer into neurons and glia in the brain", Science, 1993; 259:988-990.

Lebkowski et al., "Adeno-Associated Virus: a Vector System for Efficient Introduction of DNA into a Variety of Mammalian Cell Types", Mol. Cell Biol., 1988; 8:3988-3996.

Wu et al., "Hepatocyle-directed Gene Transfer in vivo leads to transient improvement of hypercholesterolemia in low density lipoprotein receptor-deficient rabbits", J. Biol. Chem. 1992; 267:963-967.

Wu and Wu et al., "Receptor-mediated Gene Delivery and Expression in vivo", J. Biol. Chem. 1988; 263:14621-14624.

Williams et al., "Introduction of foreign genes into tissues of living mice by DNA-coated microprojectiles", Proc. Natl. Acad. Sci USA, 1991; 88:2726-2730.

Curiel et al., "High-Efficiency gene transfer mediated by adenovirus coupled to DNA- polylysine complex", Hum. Gene. Ther., 1992, 3:147-154.

Wu and Wu et al., "Receptor-mediated in Vitro Gene Transformation by a Soluble DNA Carrier System", J. Biol. Chem., 1987, 262:4429-4432.

Mir et al., "Long-term, high level in vivo gene expression after electric pulse-mediated gene transfer into skeletal muscle", Acad. Sci., 1998, 321:893-899.

Roemer et al., "Knock-In and Knock-out",New Biol., 1991; 3:331.

Elefanty et al., "Characterization of hematopoietic progenitor cells that express the transcription factor SCL, using a lacZ "knock-in" strategy", Proc. Natl. Acad. Sci USA, 1998; 95:11897-11902.

Westphal and Leder et al.,"Transposon-generated 'knock-out' and 'knock-in' gene-targeting constructs for use in mice", Curr. Biol. 1997; 7:530.

Araki et al., "Targeted integration of DNA using mutant lox sites in embryonic stem cells", Nucleic Acids Res, 1997; 25:868-872.

Zhou et al., "Mouse model for the lysosomal disorder galactosialidosis and correction of the phenotype with overexpressing erythroid precursor cells", Genes and Development, 1995; 9:2623-34.

Coffman et al., A genetic approach for studying the physiology of the type 1A (AT1A) Angiotensin receptor, Semin. Nephrol. 1997; 17:404.

Esther et al., "Mice lacking angiotensin-converting enzyme have low blood pressure, renal pathology, and reduced male fertility",Lab. Invest., 1996; 74:953.

Kohler and Milstein et al., "Continuous celtures of fused cells secreting antibody of predefined specificity", Nature, 1975; 256:495-497.

Kozbor et al., "The production of monoclonal antibodies from human lymphocytes", Immunology Today, 1983; 4:72.

Cole et al., "Generation of human monoclonal antibodies reactive with cellular antigens". Proc. Natl. Acad. Sci USA, 1983; 80:2026-2030.

Cole et al., "The EBV-hybridoma technique and its application to human lung cancer", Monoclonal Antibodies and Cancer Therapy, Alan R. Liss, Inc., pp. 77-96, 1985.

Blondelle et al., "Novel antimicrobial compounds identified using synthetic combinatorial library technology", TIBTech, 1996; 14:60.

Sapkota et al., "BI-D1870 is a specific inhibitor of the p90 RSK (ribosomal S6 kinase) isoforms in vitro and in vivo", Biochem. J., 2007, 401:29-38.

Smith et al., "Identification of the First Specific Inhibitor of p90 Ribosomal S6 Kinase (RSK) Reveals an Unexpected Role for RSK in Cancer Cell Proliferation", Cancer Res., 2005, 65:1027-1034.

Cohen et al., "Structural Bioinformatics-Based Design of Selective, Irreversible Kinase Inhibitors", Science, 2005, 308:1318-21.

Ngyuen et al., Anti-Cancer Agents in Medicinal Chemistry, 2008, 8, 710-716.

Elbashir et al., "Duplexes of 21-nucleotide RNAs mediate RNA interference in cultured mammalian cells", Nature, 2001; 411:494-498.

Abbas-Turki et al., "Lentiviral-Mediated RNA Interference", Human Gene Ther., 2002; 13(18): 2197-2201.

Tiscornia et al., "A general method for gene knockdown in mice by using lentiviral vectors expressing small interfering RNA", Proc. Natl. Acad. Sci USA., 2003; 100:1844-8.

Hannon et al., "RNA interference", Nature, 2002; 418:244-51.

Bernstein et al., "The rest is silence", RNA, 2001; 7(11):1509-1521.

Krickevsky and Kosik et al., "RNAi functions in cultured mammalian neurons", Proc. Natl. Acad. Sci USA., 2002; 99 (18):11926-9.

Cornell et al., "Germline transmission of RNAi in mice", Nat. Struct. Biol. 2003; 10(2):91-92.

Donzelli et al., "Dual mode of degradation of Cdc25 A phosphatase", EMBO J., 2002; 21:4875-84.

Bouillet et al., "Proapoptotic Bcl-2 relative Bim Required for Certain Apoptotic Responses, Leukocyte Homeostasis, and to Preclude Autoimmunity", Science, 1999; 286:1735-1738.

Lindsten et al., "The Combined Functions of Proapoptotic Bcl-2 Family Members Bak and Bax are essential for normal development of multiple tissues", Mol. Cell, 2000, 6:1389-1399.

Dorrello et al., "S6K1- and bTrCp- mediated degradation of PDCD4 promotes protein translation and cell growth", Science, 2006; 314:467-471.

Hahn et al., "Enumeration of the Simian Virus 40 Early Region Elements Necessary for Human cell Transformation", Mol Cell Biol. 2002; 22:2111-2123.

Margottin-Goguet et al., "Prophase Destruction of Emi1 by the SCFbTrCp/Slimb Ubiquiting Ligase Activates the Anaphase Promoting Complex to Allow Progression beyond Prometaphase", Dev Cell, 2003; 4:813-26.

Anjum et al., "The tumor seppressor DAP Kinase is a target of RSK-Mediated Survival Signaling", Curr Biol., 2005, 15:1762-1767.

Roux et al., "RAS/ERK Signaling Promotes Site-specific Ribosomal Protein S6 Phosphorylation via RSK and Stimulates Cap-dependent Translation", J. Biol Chem., 2007, 282:14056-64.

Kuribara et al., "Role of Bim in Apoptosis of Normal and Bcr-Abl-Expressing Hematopoietic Progenitors", Mol. Cell. Biol. 2004, 24:6172-83.

Kuroda et al., "Bim and Bad mediate imatinib-induced killing of Bcr/Abl+ leukemic cells, and resistance due to their loss is overcome by a BH3 mimetic", Proc. Natl. Acad. Sci. USA, 2006, 103; 14907-12.

Cartlidge et al., "Oncogenic BRAFV600E inhibits BIM expression to promote melanoma cell survival", Pigment Cell Melanoma Res., 2008, 21:534-44.

Sheridan et al., "Oncogenic B-RafV600E inhibits Apoptosis and Promotes ERK-dependent inactivation of bad and bim", J. Biol. Chem., 2008, 283:22128-35.

Bai et al., "SKP1 Connects Cell Cycle Regulators to the Ubiquitin Proteolysis Machinery through a Novel Motif, the F-box", 1996, Cell 86:263-274.

Cenciarelli et al., "Identification of a family of human F-box proteins", 1999, Current Biol. 9: 1177.

Winston et al., "A family of mammalian F-box proteins", 1999, Curent Biol. 9:1180.

Margottin et al., "A novel human WD protein, h-bTrCP, that interacts with HIV-1 Vpu connects CD4 to the ER degradation pathway through an F-Box Motif", 1998, Mol. Cell 1:565.

Gonen et al., "Identification of the Ubiquitin Carrier Proteins, E2s, involved in signal-induced conjugation and subsequent degradation of IkBa", 1999, J. Biol. Chem. vol. 274(21):14823-14830.

Hatakeyama et al., "Ubiquitin-dependent degradation of IkBa is mediated by a ubiquitin ligase Skp1/Cul 1/F-box protein FWD1", 1999, Proc. Natl. Acad. Sci. USA 96: 3859-3863.

Hattori et al., "Molecular dissection of the interactions among IkBa, FWD1, and Skp1 required for Ubiquitin-mediated proteolysis of IkBa", 1999, J. Biol. Chem. 274:29641.

Kroll et al., "Inducible Degradation of IkBa by the proteasome requires interaction with the F-box protein h-bTrCP", 1999, J. Biol Chem 274:7941-7945.

Ohta et al., "ROC1, a Homolog of APC11, Represents a Family of Cullin Partners with an associated ubiquitin activity", 1999, Mol. Cell 3:535.

Shirane et al., "Common Pathway for the Ubiquitination of IkBa, IkBb, and IkBe Mediated by the F-box Protein FWD1", 1999 J. Biol. Chem 274:28169.

Spencer et al., "Signal-induced ubiquitination of IkBa by the F-box protein Slimb/ b-TrCP", 1999, Genes Dev. 13:284.

Wu and Ghosh et al., "b-TrCP Mediates the Signal-induced Ubiquitination of IkBb", 1999, J. Biol. Chem. 274:29591.

Yaron et al., "Identification of the receptor component of the IkBa-ubiquitin ligase", 1998, Nature 396:590.

Jiang and Struhl et al., "Regulation of the Hedgehog and wingless signalling pathways by the F-box/WD40-repeat protein Slimb", 1998, Nature 391:493.

Marikawa and Elinson et al., "b-TrCP is a negative regulator of the Wnt/b-catenin signaling pathway and dorsal axis formation in *Xenopus* embryos", 1998, Mech. Dev. 77:75-80.

Hart et al., "The F-box protein b-TrCP associates with phosphorylated b-catenin and regulates its activity in the cell", 1999, Curr. Biol. 9:207.

Kitagawa et al.,"An F-box protein, FWD1, mediates ubiquitin-dependent proteolysis of b-catenin", 1999, EMBO J. 18:2401.-2410.

Latres et al., "The human F box protein b-Trcp associates with the Cul1/Skp1 complex and regulates the stability of b-catenin", 1999, Oncogene 18:849-854.

Winston et al., "The SCFb-TRCP-ubiquitin ligase complex associates specifically with phosphorylated destruction motifs in IkBa and b-catenin and stimulates IkBa ubiquitination in vitro", 1999, Genes Dev 13:270.

Lassot et al., ATF4 Degradation Relies on a Phosphorylation-Dependent Interaction with the SCFb-TrCP Ubiquitin Ligase, 2001, Mol. Cell. Biol. 21:2192-2202.

Fukuchi et al., "Ligand-dependent Degradation of Smad3 by a Ubiquitin Ligase Complex of ROC1 and Associated Proteins", 2001, Mol. Biol. Cell 12:1431-1443.

Orian et al., "SCFb-TrCP ubiquitin ligase-mediated processing of NF-kB p105 requires phosphorylation of its C-terminus by IkB kinase", 2000, EMBO J. 19:2580-2591.

Fong and Sun et al., "Genetic evidence for the essential role of b-Transducin repeat-containing protein in the inducible processing of NF-kB2/p100", 2002, J. Biol. Chem 277:22111-22114.

Davis et al., Pseudosubstrate regulation of the SCFb-TrCP ubiquitin ligase by hnRNP-U, 2002, Genes Dev. 16:439.

Kipreos and Pagano ep al., "The F-box protein family", 2000, Genome Biology 1:3002.1-3002.7.

Fuchs et al., "HOS, a human homolog of Slimb, forms an SCF complex with Skp1 and Cullin1 and targets the phosphorylation-dependent degradation of IkB and b-catenin", 1999, Oncogene 18:2039.

Suzuki et al., "IkBa Ubiquitination is catalyzed by an SCF-like complex containing Skp1, Cullin-1, and two F-box/WD40-Repeat Proteins, bTrCp1 and bTrCp2", 1999, Biochem Biophys Res Commun 256:127-132.

Tan et al., "Recruitment of a ROC1-CUL1 Ubiquitin Ligase by Skp1 and HOS to Catalyze the Ubiquitination of IkBa", 1999, Mol. Cell 3:527-533.

Ciechanover et al., "The ubiquitin-proteasome pathway: on protein death and cell life", 1998, EMBO J. 17:7151-7160.

Spataro et al., "The ubiquitin-proteasome pathway in cancer", 1998, Br. J. Cancer 77:448-455.

Peifer et al., "b-Catenin as Oncogene: The smoking Gun", 1997 Science, 275:1752-1753.

Lloyd et al., "p27kip: A multifunctional cyclin-dependent kinase inhibitor with prognostic significance in Human Cancer", 1999, Am. J. Pathol. 154:313.

Guardavaccaro et al., "Control of Meiotic and Mitotic Progression by the F-box Protein b-TrCP1 in vivo", Developmental Cell, 2003, 4:799-812.

Soldatenkov et al., "Inhibition of Homologue of Slib (HOS) Function Sensitized Human Melanoma Cells for Apoptosis", Cancer Res., 1999, 59:5085-5088.

Hood et al., "Natural transplantation in tunicates", Immunology, 2 Ed., 1984, Benjamin/Cummings:Menlo Park, California, p. 384.

Saiki et al., "Primer-Directed Enzymatic Amplifiction of DNA with a Thermostable DNA polymerase", Science 1988, 239:487.

Reeck et al., "Homology in proteins and nucleic acids: a terminology muddle and a way out of it", Cell 1987, 50:667.

Southern, et al., "Detection of specific sequences among DNA fragments separated by gel electrophoresis", J Mol. Biol. 1975; 98:503-517.

Karlin and Altschul et al., "Applications and statistics for multiple high-scoring segments in molecular sequences", Proc. Natl. Acad. Sci. USA 1993, 90:5873-5877.

Karlin and Altschul et al., "Methods for assessing the statistical significance of molecular sequence features by using genaral scoring schemes", Proc Natl. Acad. Sci. USA, 1990, 87:2264-2268.

Altschul et al., "Basic Local Alignment Search Tool", J. Mol. Biol. 1990, 215:403-410.

Altschul et al., "Gapped BLAST and PSI-BLAST: a new generation of protein database search programs", Nucleic Acids Res. 1997, 25:3389-3402.

Myers and Miller et al., "Optimal alignments in linear space", CABIOS 1988, 4:11-17.

Langer et al., "New methods of drug delivery", Science, 1990; 249:1527-1533.

Treat et al., Liposomes in the Therapy of infectious disease and cancer, Lopez-Berestein and Fidler (eds) Liss, NY, pp. 353-365 (1989).

Benoist and Chambon et al., "In vivo sequence requirements of the SV40 early promoter region", Nature 1981; 290:304-310.

Yamamoto et al., "Identification of a functional promoter in the long terminal repeat of Rous sacroma virus", Cell 1980; 22:787-797.

Wagner et al., "Nucleotide sequence of the thymidine kinase gene of herpes simplex virus type 1", Proc. Natl. Acad. Sci. USA 1981; 78:1441-1445.

Brinster et al., "Regulation of metallothionein-thymidine kinase fusion plasmids injected into mouse eggs", Nature 1982; 296:39-42.

\* cited by examiner

Figures 2 B-C
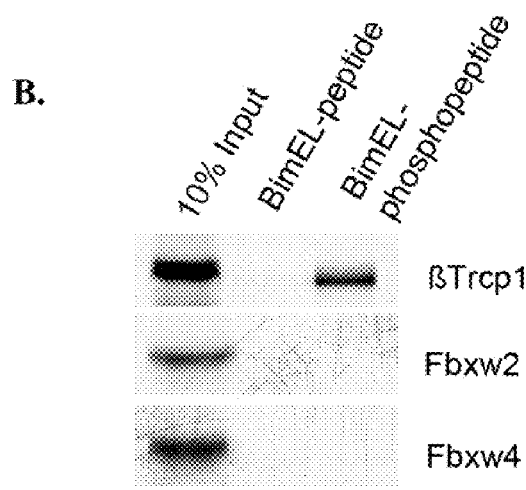
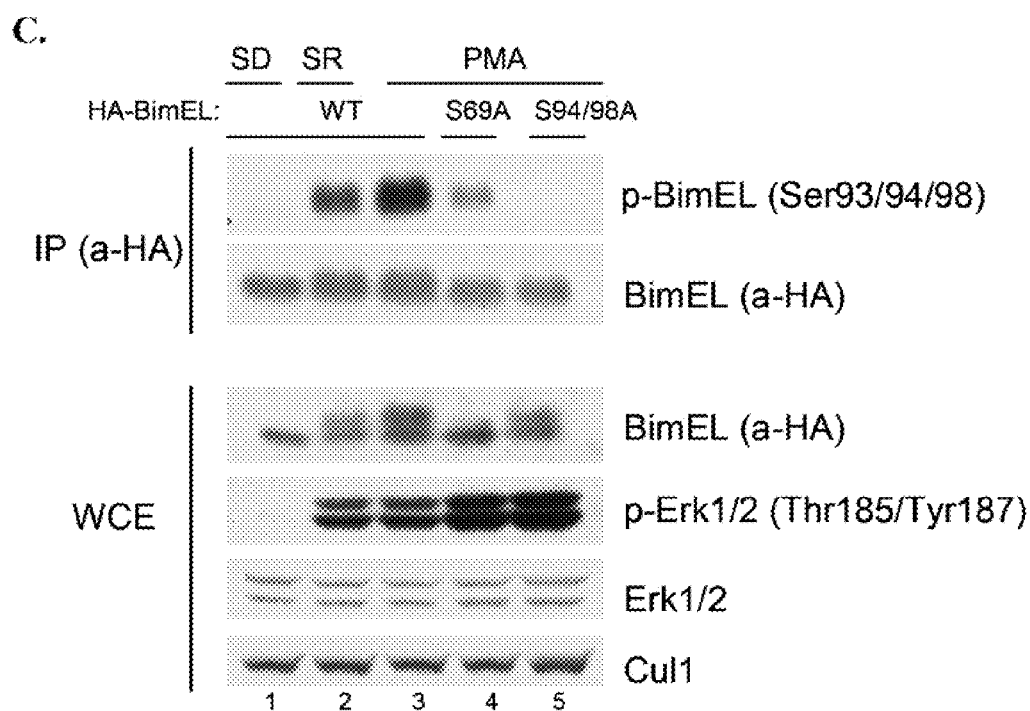

A.
IkBα:  DDRHDSGL
BAD:   RSRHSSYP
DAPK:  LSRKASAV
BIM:   LSRSSSGY

Figures 5 A - B
A.
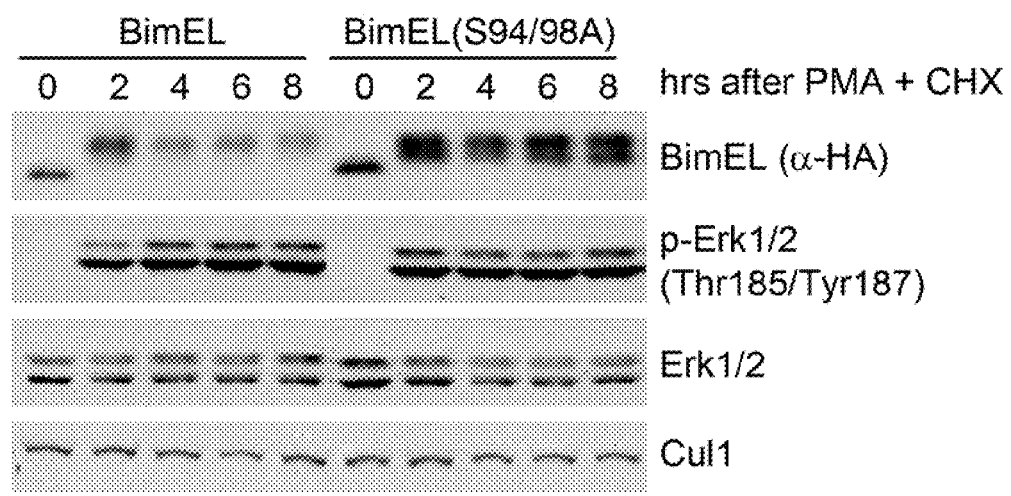
B.
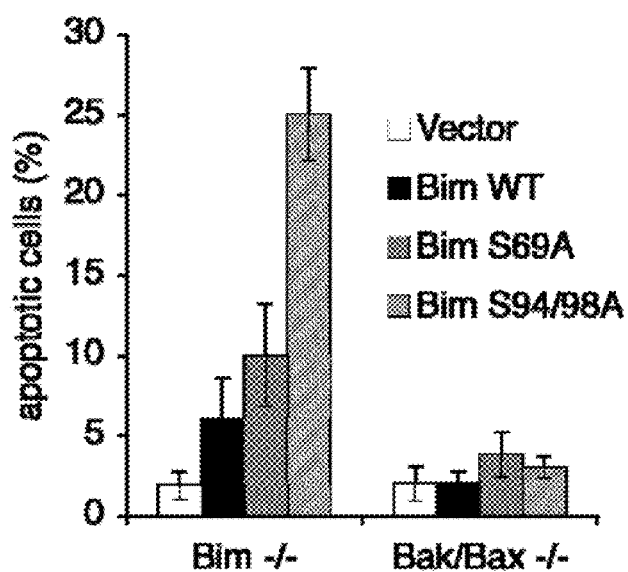

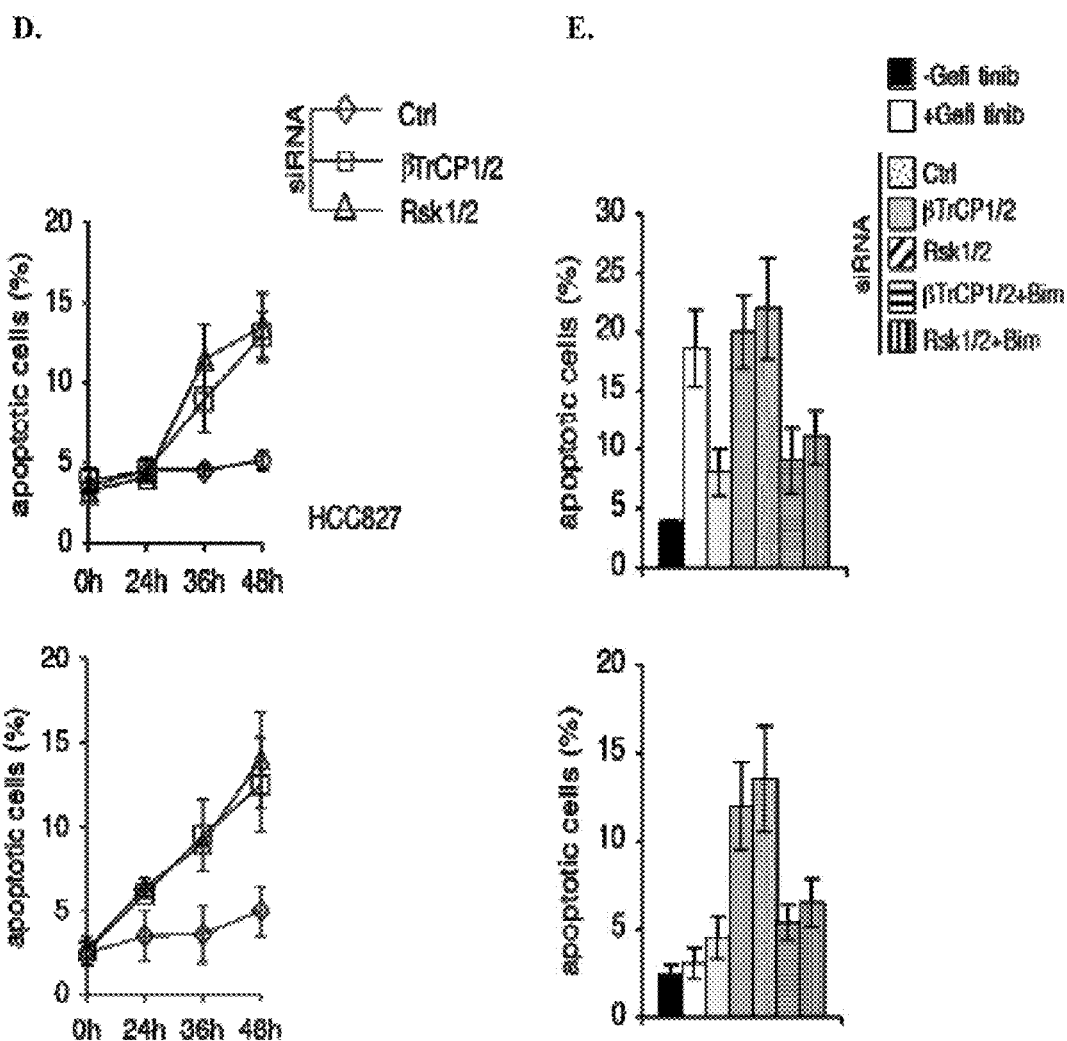
Figures 5 D-E

β-TRCP1, β-TRCP2 AND RSK1 OR RSK2 INHIBITORS AND METHODS FOR SENSITIZING TARGET CELLS TO APOPTOSIS

CROSS REFERENCE TO RELATED APPLICATIONS

The present application claims the benefit of U.S. Provisional Patent Application Ser. No. 61/058,801, filed on Jun. 4, 2008, the contents of which are hereby incorporated by reference in its entirety.

FEDERALLY SPONSORED RESEARCH OR DEVELOPMENT

This invention was made in part in the course of research sponsored by the National Institutes of Health (NIH) Grants R01-GM57587, R37-CA76584 and R21-CA 125173. The U.S. government may have certain rights in this invention.

FIELD OF THE INVENTION

The invention relates to modulating BimEL levels (Bcl-2-Interacting Mediator of cell death, Extra Long isoform) to sensitize cancer cells to cell death or apoptosis. In certain embodiments, the invention relates to increasing BimEL levels. In certain embodiments, the invention relates to inhibitors of β-TrCP1, β-TrCP2 (F-box protein members) RSK1, or RSK2 (p90$^{rsk}$/MAPKAP kinase-1 or 2) that sensitize tumor cells to chemotherapy-induced cell death or apoptosis.

BACKGROUND OF THE INVENTION

The availability of the human and mouse genome sequences has allowed the identification and comparison of their respective degradomes—the complete repertoire of proteases that are produced by these organisms. Because of the essential roles of proteolytic enzymes in the control of cell behavior, survival and cell death, degradome analysis provides a useful framework for the global exploration of these protease-mediated functions in normal and pathological conditions.

The Ubiquitin Pathway

Ubiquitin-mediated proteolysis is an important pathway of non-lysosomal protein degradation which controls the timed destruction of many cellular regulatory proteins including, p27, p53, p300, cyclins, E2F, STAT-1, c-Myc, c-Jun, EGF receptor, IκBα, NFκB and β-catenin (reviewed in Pagano, 1997, FASEB J. 11: 1067). Ubiquitin is an highly conserved 76-amino acid polypeptide that is abundantly present in all eukaryotic cells. The ubiquitin pathway leads to the covalent attachment of a poly-ubiquitin chain to target substrates which are then degraded by the multi-catalytic proteasome complex (see Pagano, supra, for a recent review). Many of the steps regulating protein ubiquitination are known. Initially the ubiquitin activating enzyme (E1), forms a high energy thioester with ubiquitin which is, in turn, transferred to a reactive cysteine residue of one of many ubiquitin conjugating enzymes (Ubcs or E2s). The final transfer of ubiquitin to an e-amino group of a reactive lysine residue in the target protein occurs in a reaction that may or may not require an ubiquitin ligase (E3) protein. The large number of ubiquitin ligases ensures a high level of substrate specificity.

The Ubiquitin Pathway and the Regulation of the G1 Phase by F Box Proteins

Genetic and biochemical studies in several organisms have shown that the G 1 phase of the cell cycle is regulated by the ubiquitin pathway. Proteolysis of cyclins, Ckis and other G1 regulatory proteins is controlled in yeast by the ubiquitin conjugating enzyme Ubc3 (also called Cdc34) and by an E3 ubiquitin ligase formed by three subunits: Cdc53, Skp1 and one of many F box proteins (reviewed in Patton, et al., 1998, Trends in Genet. 14:6). The F box proteins (FBPs) are so called because they contain a motif, the F Box, that was first identified in Cyclin F, and that is necessary for FBP interaction with Skp1 (Bai, et al., 1996, Cell 86:263). Cdc53 (also called Cul A) and Skp1 appear to participate in the formation of at least three distinct E3s, each containing a different FBP. Because these ligases are similar protein modules composed of Skp1, Cul A, and an FBP, they have been named SCF. The three SCFs identified in *S. cerevisiae* are: SCF$^{Cdc4}$ (which recruits the Ckis Sic1 and Far1, the replication factor Cdc6, and the transcriptional activator Gcn4, as substrates through the F-Box protein Cdc4), SCF$^{Grr1}$ (which recruits the G1 cyclins Cln1 and Cln2 as substrates through the F-Box protein GRR1), and SCF$^{Met30}$ (which recruits the G1 cyclin Cln3 as a substrate throughout the F box protein MET30; see Pagano and Patton, supra, for recent reviews).

The interaction of SCF ligase with its substrates occurs via the FBP. FBPs are present in all eukaryotes (at least 54 in mammals; Cenciarelli, et al., 1999, Current Biol. 9: 1177; Winston, et al., 1999, Current Biol. 9: 1180). In addition to the F Box, many FBPs contain additional domains that facilitate both protein:protein interactions, e.g. WD-40 domains or leucine-rich repeats (LRRs), and protein:DNA interactions, e.g. tankyrase binding domains or HNH domains. Since the substrate specificity of SCF ligases is dictated by different FBPs that act as substrate targeting subunits, the large numbers of FBPs with varying combinations of protein or DNA interaction domains ensure highly specific substrate recognition.

FBP1, a Mammalian FBP Involved in Regulation of APC/C

Fbp1, the mammalian homolog of *Xenopus* β-TrCP1 (β-transducin repeat containing protein) (Spevak, et al., 1993, Mol. Cell. Biol. 8:4953), was identified using Skp1 as a bait in a two-hybrid screen (Cenciarelli, et al., supra). Fbp1 is an F box protein containing seven WD-40 domains (Margottin, et al., 1998, Mol. Cell. 1:565), and is involved in the degradation of IκBα family members in response to NFκB activating stimuli (Gonen, et al., 1999, J. Biol. Chem. 274:14823; Hatakeyama, et al., 1999, Proc. Natl. Acad. Sci. USA 96:3859; Hattori, et al., 1999, J. Biol. Chem. 274:29641; Kroll, et al., 1999, J. Biol. Chem. 274:7941; Ohta, et al., 1999, Mol. Cell. 3:535; Shirane, et al., 1999, J. Biol. Chem. 274: 28169; Spencer, et al., 1999, Genes Dev. 13:284; Winston, et al., 1999, Genes Dev. 13:270; Wu and Ghosh, 1999, J. Biol. Chem. 274:29591; Yaron, et al., 1998, Nature 396:590). In addition, consistent with the finding that *Xenopus* and *Drosophila* Fbp1 orthologs act as negative regulators of the Wnt/β-catenin signaling pathway (Jiang and Struhl, 1998, Nature 391:493; Marikawa and Elinson, 1998, Mech. Dev. 77:75), several studies report that human Fbp1 controls β-catenin stability in vitro and in mammalian cultured cells (Hart, et al., 1999, Curr. Biol. 9:207; Hatakeyama, et al., supra; Kitagawa, et al., 1999, EMBO J. 18:2401; Latres, et al., 1999, Oncogene 18:849; Winston, et al., 1999, Genes Dev. 13:270).

Well-characterized substrates of mammalian Fbp1 have been found to share a common destruction motif, DSGxxS, and are recognized by Fbp1 only upon phosphorylation of the two serine residues present in this motif. There is, however, some recent evidence for additional mammalian substrates of Fbp1 lacking a completely conserved binding domain, such as ATF4 (Lassot, et al., 2001, Mol. Cell. Biol. 21:2192), Smad3 (Fukuchi, et al., 2001, Mol. Biol. Cell 12:1431), NFκB p105 (Orian, et al., 2000, EMBO J. 19:2580) and NFκB p100 (Fong and Sun, 2002, J. Biol. Chem. 277:22111). A conserved DSGxxS motif is present not only in Fbp1 substrates but also in certain regulators of Fbp1, such as the HIV protein Vpu, which targets Fbp1 to the non-physiological substrate, CD4, in virally infected cells. (Margottin, et al., supra). The DSGxxS destruction motif may also be found in peptide regulators of Fbp1 termed pseudosubstrates; however, pseudosubstrates escape the normal degradation fate of other FBP target proteins and instead modulate the activity of the FBP, and corresponding Cks, such as cellular localization and substrate targeting. For example, the Fbp1 pseudosubstrate hnRNP-U not only inhibits Fpb1 from targeting inappropriate substrates but also serves to localize Fbp1 to the nucleus (Davis, et al., 2002, Genes Dev. 16:439).

A further level of complexity is added by the presence of a Fbp1/β-TrCP1 (beta-transducin repeat containing protein 1) paralogous gene product, called β-TrCP2 (beta-transducin repeat containing protein 2) or Fbxw1B (78% identical, 86% similar to β-TrCP1; Kipreos and Pagano, 2000, Genome Biology 1:3002.1). Fbp1 and β-TrCP2 are ubiquitously expressed in adult human tissues (Cenciarelli, et al., supra; Koike, et al., 2000, Biochem. Biophys. Res. Commun. 269: 103). In addition, β-TrCP2 has biochemical properties similar to Fbp1 in its ability to sustain the ubiquitinylation of both β-catenin and IκBα family members in vitro and to control their degradation in mammalian cultured cells (Fuchs, et al., 1999, Oncogene 18:2039; Suzuki, et al., 1999, Biochem. Biophys. Res. Commun. 256:127; Tan, et al., 1999, Mol. Cell. 3:527). Despite these similarities, Fbp1 localizes to the nucleus and β-TrCP2 localizes mainly to the cytoplasm (Davis, et al., 2002, Genes Dev. 16:439). It is not clear whether these two FBPs have overlapping functions in vivo, or if each of them recognizes specific substrates.

Deregulation of the Ubiquitin Pathway in Cancer and Other Proliferative Disorders Cancer develops when cells multiply too quickly. Cell proliferation is determined by the net balance of positive and negative signals. When positive signals overcome or when negative signals are absent, the cells multiply too quickly and cancer develops.

Ordinarily cells precisely control the amount of any given protein and eliminate the excess or any unwanted protein. To do so, the cell ubiquitinates the undesired protein to tag the protein for proteasome degradation. This mechanism goes awry in tumors, leading to the excessive accumulation of positive signals (oncogenic proteins), or resulting in the abnormal degradation of negative regulators (tumor suppressor proteins). Thus, without tumor suppressor proteins or in the presence of too much of an oncogenic protein, cells multiply without control, forming tumors (reviewed by Ciechanover, 1998, EMBO J. 17: 7151; Spataro, 1998, Br. J. Cancer 77: 448). For example, abnormal ubiquitin-mediated degradation of the p53 tumor suppressor (reviewed by Brown and Pagano, 1997, Biochim. Biophys. Acta 1332:1), the putative oncogene β-catenin (reviewed by Peifer, 1997, Science 275: 1752) and the Cki p27 (reviewed in Ciechanover, supra; Spataro, supra; Lloyd, 1999, Am. J. Pathol. 154: 313) have been correlated with tumorigenesis, opening to the hypothesis that some genes encoding ubiquitinating enzymes may be mutated in tumors.

Initial evidence indicates that human F box proteins play a role in the ubiquitination of G1 regulatory proteins as do their homologues in yeast. Unchecked degradation of cell cycle regulatory proteins has been observed in certain tumors and it is possible that deregulated ubiquitin ligase plays a role in the altered degradation of cell cycle regulators. A well understood example is that of Mdm2, a ubiquitin ligase whose overexpression induces low levels of its substrate, the tumor suppressor p53.

Alternately, F box proteins have been shown to interact directly with DNA regulating proteins or DNA itself. F box proteins in yeast are known to regulate genomic stability and senescence, and recent data has shown that F box inhibition in mammalian cells can lead to the loss of DNA damage checkpoints.

Even though F-box proteins and related proteins have been shown to be involved in the ubiquitin pathway, relatively little is known about the activities and roles of specific members on the cell cycle or their roles in cell death or apoptosis.

There is a general need for cancer treatments and in particular for treatments relating to regulating or affecting the cell cycle to sensitize tumor or cancer cells to cell death or apoptosis. In particular, there is a need for small molecule inhibitors that are useful as cancer chemotherapeutics, as well as for diagnostic and screening tools for cancer.

SUMMARY OF THE INVENTION

The present invention provides a method of sensitizing a cell to cell death or apoptosis comprising contacting a target cell with an effective amount of an inhibitor of β-TrCP1, β-TrCP2, RSK1, or RSK2. In certain embodiments, the inhibitor results in an increase in the amount of BimEL (Bcl-2-Interacting Mediator of cell death, Extra Long isoform) protein compared to the amount of BimEL protein prior to use of an effective amount of the inhibitor.

In additional embodiments the invention provides a method of killing a target cell comprising contacting a cell with an amount of an inhibitor of β-TrCP1, β-TrCP2, RSK1, or RSK2 that is effective to sensitize the cell to cell death or apoptosis.

In additional embodiments the invention provides a method of screening for an agent useful for inducing cell death or apoptosis of a target cell comprising:
  i) contacting a cell expressing β-TrCP1, β-TrCP2, RSK1, or RSK2 with a test compound; and
  ii) comparing the degradation rate of the β-TrCP1, β-TrCP2, RSK1, or RSK2 to a control, wherein the control is the degradation rate of β-TrCP1, β-TrCP2, RSK1, or RSK2 in the absence of the test compound; and
  iii) selecting a test compound that increases the degradation rate of β-TrCP1, β-TrCP2, RSK1, or RSK2 as compound useful for inducing cell death or apoptosis of a target cell.

In additional embodiments, the invention provides a method of screening for an agent useful for inducing cell death or apoptosis of a cancer cell comprising:
  i) contacting a cell expressing β-TrCP1, β-TrCP2, RSK1, or RSK2 with a test compound;
  ii) comparing the amount of β-TrCP1, β-TrCP2, RSK1, or RSK2 present in the cell in the presence and in the absence of the test compound; and
  iii) selecting a test compound that decreases the amount of β-TrCP1, β-TrCP2, RSK1, or RSK2 in the cell as a compound useful for inducing apoptosis of a cancer cell.

In additional embodiments, the invention provides a method of treating cancer in a mammalian subject which comprises: administering an effective amount of at least one β-TrCP1, β-TrCP2, RSK1, or RSK2 inhibitor to a mammalian subject suffering from cancer, wherein the inhibitor sensitizes cancer cells to chemotherapy induced cell death or apoptosis.

In certain embodiments, the β-TrCP1, β-TrCP2, RSK1, or RSK2 inhibitor results in an increase in the amount of BimEL (Bcl-2-Interacting Mediator of cell death, Extra Long isoform) protein in a cell when compared to the amount of BimEL protein in the cell prior to administering the inhibitor.

In additional embodiments, the target cell is a diseased or abnormal cell from tissue or a cell line that exhibits a disease or an abnormal condition selected from the group consisting of cancer, infection, immune disorder, cardiovascular disease, and inflammatory disorders.

In yet additional embodiments, the method further comprises contacting the cell with a second agent for sensitizing the cell to DNA damage, or for inducing apoptosis or cell death of a target cell.

In additional embodiments, the test compound is an siRNA. In yet additional embodiments, the siRNA comprises SEQ ID NO:19, SEQ ID NO:20, SEQ ID NO:21, or SEQ ID NO:22.

In additional embodiments, the test compound is a small molecule inhibitor of β-TrCP1, β-TrCP2, RSK1, and/or RSK2. In a specific embodiment, the small molecule inhibitor is RSK inhibitor selected from the group consisting of BI-D1870, SL0101, and FMK.

In yet additional embodiments, the β-TrCP1 comprises SEQ ID NO:1, β-TrCP2 comprises SEQ ID NO:4, RSK1 comprises SEQ ID NO:8, and RSK2 comprises SEQ ID NO:10.

In additional embodiments, the invention provides a kit for screening for an agent useful for modulating BimEL (Bcl-2-Interacting Mediator of cell death, Extra Long isoform) protein activity comprising: a BimEL protein, at least one β-TrCP1, β-TrCP2, RSK1, or RSK2 protein, and a means for detecting binding between the BimEL and the β-TrCP1, β-TrCP2, RSK1, or RSK2 protein.

In additional embodiments, the invention provides a kit for screening for an agent useful for inducing cell death or apoptosis comprising: a BimEL (Bcl-2-Interacting Mediator of cell death, Extra Long isoform) protein at least one β-TrCP1, β-TrCP2, RSK1, or RSK2 protein, and a means for detecting binding between the BimEL protein and the β-TrCP1, β-TrCP2, RSK 1, or RSK2 protein.

In yet additional embodiments, the invention provides a method for sensitizing a cell to apoptosis or cell death in a target cell of a mammal in need thereof, which comprises contacting said target cell with an effective amount of an inhibitor of β-TrCP1, β-TrCP2, RSK1, or RSK2. In certain embodiments, the cell is a diseased or abnormal cell from a mammal that exhibits a disease or abnormal condition selected from the group consisting of cancer, infection, immune disorder, cardiovascular disease, and inflammatory disorders. In additional embodiments, the method further comprises contacting the cell with a second agent for sensitizing the cell to DNA damage, or for inducing apoptosis or cell death of a target cell. In certain embodiments, the mammal is a human.

In yet additional embodiments, the inhibitor of β-TrCP1, β-TrCP2, RSK1, or RSK2 comprises SEQ ID NO:19, SEQ ID NO:20, SEQ ID NO:21, or SEQ ID NO:22, respectively.

In yet additional embodiments, the invention provides a method of screening for an agent for sensitizing a target cell to apoptosis or cell death comprising: i) measuring the level of β-TrCP1, β-TrCP2, RSK1, or RSK2 expressed by a target cell, ii) contacting the target cell that expresses β-TrCP1, β-TrCP2, RSK1, or RSK2 with a test compound, iii) measuring the amount of β-TrCP1, β-TrCP2, RSK1, or RSK2 expressed by the cell after said contacting step, iv) comparing the level of β-TrCP1, β-TrCP2, RSK1, or RSK2 expression in said cell before and after said contacting step, and v) selecting as a therapeutic agent candidate a test compound that decreases the level of β-TrCP1, β-TrCP2, RSK1, or RSK2 by said target cell.

In still further embodiments, the invention provides a method of screening for an agent for sensitizing a target cell to apoptosis or cell death comprising: i) measuring the level of BimEL (Bcl-2-Interacting Mediator of cell death, Extra Long isoform) protein expressed by a target cell, ii) contacting the target cell that expresses BimEL protein with a test compound, iii) measuring the amount of BimEL protein expressed by the cell after said contacting step, iv) comparing the level of BimEL expression in said cell before and after said contacting step, and v) selecting as a therapeutic agent candidate a test compound that increases the level of BimEL protein by said target cell.

In certain embodiments, the cell is a diseased or abnormal cell from a mammal that exhibits a disease or abnormal condition selected from the group consisting of cancer, infection, immune disorder, cardiovascular disease, and inflammatory disorders.

BRIEF DESCRIPTION OF THE DRAWINGS

FIGS. 2A-C are immunoblots illustrating that Ser93, Ser94, and Ser 98 are required for BimEL interaction with β-TrCP1.

DETAILED DESCRIPTION

Figure 1:
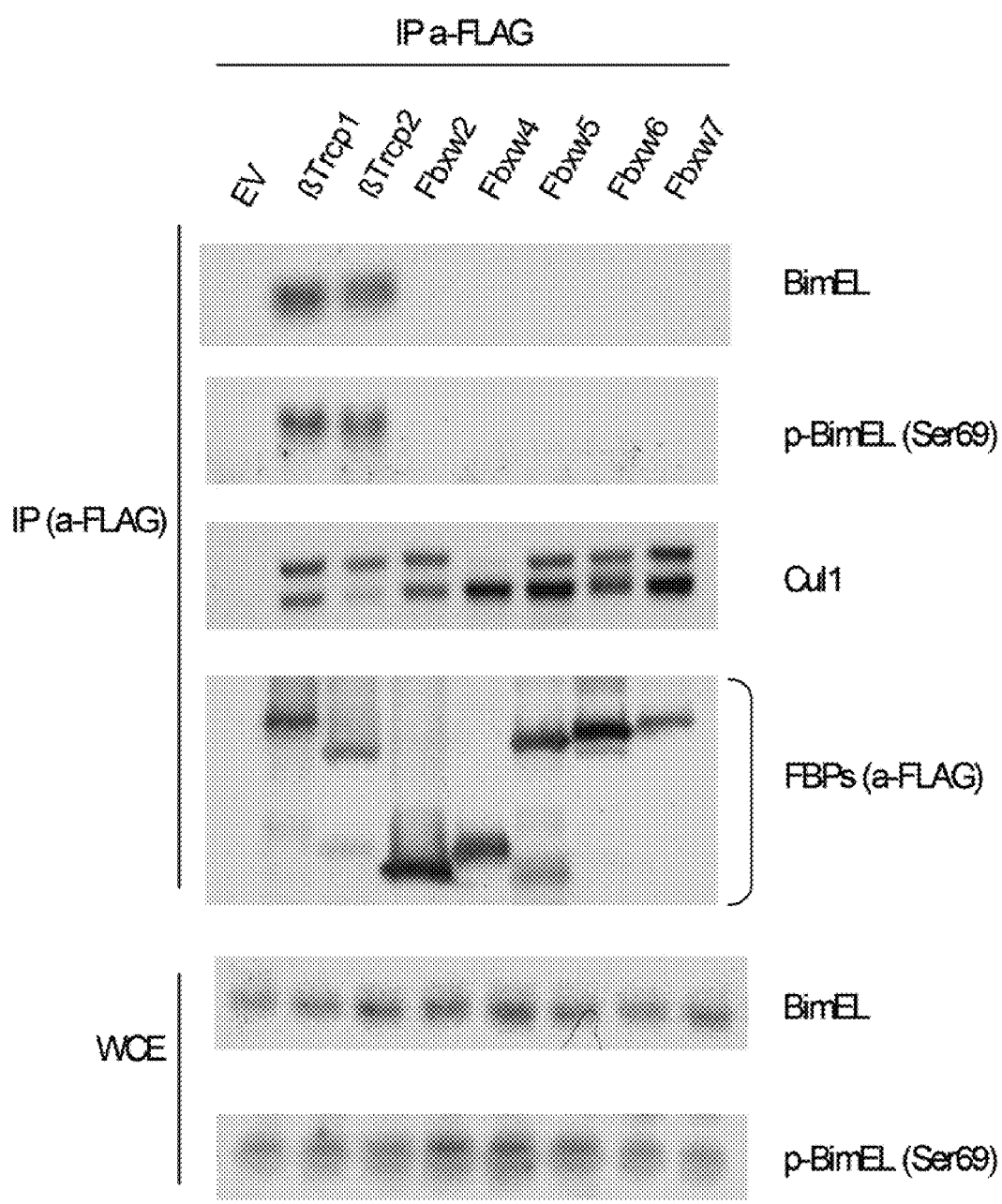
FIG. 1 is an immunoblot illustrating that BimEL specifically interacts with β-TrCp1 and β-TrCP2.

In one embodiment of the present invention, inhibitors of β-TrCP1, β-TrCP2 (F-box protein members) RSK1, or RSK2 (p90$^{rsk}$/MAPKAP kinase-1 or 2) have been found to induce cell death or apoptosis by increasing the abundance of BimEL (Bcl-2Interacting Mediator of cell death, Extra Long isoform) in cancerous cells. Thus, the invention relates to modulating BimEL levels to potentiate killing of a cancerous cell (e.g. a tumor cell), and in particular to increase the amount of BimEL in the cancerous cell. In certain embodiments, the invention relates to modulating BimEL levels to potentiate killing cancerous cells, and in particular to increase BimEL levels to sensitize the cancer cells to apoptosis when exposed to a second agent, such as chemotherapy or radiation. In addition to applications relating to cancer therapies and diagnostics, the BimEL modulators and assays of the present invention will be employed for identifying novel drugs useful for various proliferative and/or differentiative disorders such as major opportunistic infections, immune disorders, cardiovascular diseases and inflammatory disorders.

In another embodiment of the present invention, the F-box proteins β-TrCP1 and β-TrCP2 (referred to herein as β-TrCP1/2) have been shown to be important for the ubiquitin-mediated degradation of BimEL. In particular, the present data reveal that β-TrCP1 and β-TrCP2 bind specifically to phosphorylated BimEL. Three serine residues Ser93, Ser94, and Ser98 were identified as conserved in the $^{93}$SSGxxS$^{98}$ degron sequence typical of β-TrCP1/2 substrates. Phosphorylation on these residues following the induction of survival stimuli is important for β-TrCP1/2 binding to BimEL. A single mutation of any of residues Ser93, Ser94, or Ser98 strongly decreased β-TrCP1/2-BimEL binding and enhanced BimEL apoptotic activity. Silencing of β-TrCP1/2 led to accumulation of BimEL by inhibiting the degradation of BimEL.

Human β-TrCP1 has been sequenced and has an amino acid sequence according to GenBank Accession No. NP 378663 (SEQ ID NO:1); the β-TrCP1 coding sequence is GenBank Accession No. 033637 (SEQ ID NO:2), while a cDNA fragment corresponds to SEQ ID NO:3. The β-TrCP1 gene encodes a member of the F-box protein family which is characterized by an approximately 40 amino acid motif, the F-box (Fbox Motif β-TrCP1: DHIAENILSYLDAKSL-CAAELVCKEWYRVTSDGMLWKK (SEQ ID NO:14)). The F-box proteins constitute one of the four subunits of ubiquitin protein ligase complex called SCFs (SKP1-cullin-F-box), which function in phosphorylation-dependent ubiquitination. The F-box proteins are divided into 3 classes: Fbws containing WD-40 domains, Fbls containing leucine-rich repeats, and Fbxs containing either different protein-protein interaction modules or no recognizable motifs. The protein encoded by this gene belongs to the Fbws class; in addition to an F-box, this protein contains multiple WD-40 repeats. This protein is homologous to *Xenopus* β-TrCP1, yeast Met30, *Neurospora* Scon2 and *Drosophila* Slimb proteins. It interacts with HIV-1 Vpu and connects CD4 to the proteolytic machinery. It also associates specifically with phosphorylated IκBα and β-catenin destruction motifs, most likely functioning in multiple transcriptional programs by activating the NF-κB pathway and inhibiting the β-catenin pathway. Human β-TrCP1 is a variant that contains an additional 108 nt fragment within the coding region, as compared to human variant 2 (β-TrCP2), and thus encodes an in-frame 36 aa longer isoform than human variant β-TrCP2.

Human β-TrCP2 has been sequenced and has an amino acid sequence according to GenBank Accession No. 003930 (SEQ ID NO:4); the coding sequence is GenBank Accession No. 003939 (SEQ ID NO:5).

Human BimEL has been sequenced and is a 198 amino acid long protein according to GenBank Accession No. AAC39593 (SEQ ID NO:6); the coding sequence is GenBank Accession No. AF032457 (SEQ ID NO:7). While human BimEL sequences are preferred in the present methods, other suitable BimEL sequences such as rat or mouse sequences could be utilized.

Human RSK1 has been characterized as a 735 amino acid isoform a, and also a 744 amino acid isoform b that has GenBank Accession No. Q15418 (SEQ ID NO:8) (Ref Seqs ID: isoform a NP_002944.2 (SEQ ID NO:26), isoform b NP_001006666.1); the coding sequence for isoform b is GenBank Accession No. BC014966 Ref Seq ID: NM_001006665.1 (SEQ ID NO:9) (Ref Seq ID: isoform a NM_002953.3 (SEQ ID NO:27, isoform b NM_001006665.1).

Human RSK2 has been sequenced and is a 740 amino acid long protein according to GenBank Accession No. P51812 (Ref Seq ID NP_004577.1) (SEQ ID NO:10); the coding sequence is GenBank Accession No. NM_004586.2 (SEQ ID NO: 11).

Human Cdc25A (cell division cycle 25A protein) has been sequenced and is a 524 amino acid long protein according to GenBank Accession No. NP_001780 (SEQ ID NO:12); the coding sequence is GenBank Accession No. NM_001789 (SEQ ID NO:13).

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual*. 3rd ed. Cold Spring Harbor Laboratory Press: Cold Spring Harbor, N.Y.; Ausubel et al. eds. (2005) *Current Protocols in Molecular Biology*. John Wiley and Sons, Inc.: Hoboken, N.J.; Bonifacino et al. eds. (2005) *Current Protocols in Cell Biology*. John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.; *Nucleic Acid Hybridization*, Hames & Higgins eds. (1985); *Transcription And Translation*, Hames & Higgins, eds. (1984): *Animal Cell Culture* Freshney, ed. (1986); *Immobilized Cells And Enzymes*, IRL Press (1986): Perbal, *A Practical Guide To Molecular Cloning* (1984); and Harlow and Lane. *Antibodies: A Laboratory Manual* (Cold Spring Harbor Laboratory Press: 1988).

DEFINITIONS

The following definitions are provided for clarity and illustrative purposes only, and are not intended to limit the scope of the invention.

The term apoptosis means a form of cell death in which a programmed sequence of events leads to the elimination of cells. Apoptosis plays an important role in developing and maintaining health by eliminating old cells, unnecessary cells, and unhealthy cells. The human body replaces perhaps a million cells a second. Too little or too much apoptosis plays a role in many diseases. When programmed cell death does not work properly, cells that should be eliminated may remain and become immortal. An example of the lack of proper apoptosis occurs for example, in cancer and leukemia. Impaired apoptosis is central for the development of cancer. Defects in apoptosis not only provide the cells an intrinsic survival advantage but also confer resistance to chemotherapeutic drugs. When apoptosis works too well, it kills too many cells and inflicts tissue damage. Apoptosis is also called programmed cell death or cell suicide.

As used herein, apoptosis, cell suicide, and programmed cell death are used interchangeably.

The term "cell death" is used generally to mean any type of cell death, and is not limited to programmed cell death or apoptosis. BimEL is involved in programmed cell death.

A "β-transducin repeat containing protein" or "β-TrCP" herein is a protein belonging to the family of F-box proteins containing 6-7 repeats of WD40 domains. Synonyms of β-TrCP1/2 include Fbw1a, FWD1a, Fbw1b, FWD1b, FBP1, and Hos. An F-box motif is a stretch of about 40 amino acids identified as being necessary for the interaction of F-box proteins with Skp1. The consensus sequence of an F-box motif is described in Bai et al., Cell, 1996; 86:263-274, hereby incorporated by reference in its entirety. A WD40 domain is a consensus sequence of about 40 amino acid repeats rich in tryptophan (Trp) and aspartic acid (Asp) residues (Neer et al., Nature, 1996, 371:297-300 and references therein, all of which hereby incorporated by reference in their entireties). A β-TrCP protein is characterized by being capable of a substrate specificity for at least one, preferably at least two, more preferably at least three, and most preferably at least all of phosphorylated Cdc25A, β-catenin, Emi1 (Guardavaccaro et al., Developmental Cell, 2003; 4:799-812), and IkB (Soldatenkov et al., Cancer Res., 1999; 59:5085-5088). A β-TrCP protein exhibits at least 50%, 70%, 80%, 90%, 95%, 96%, 97%, 98%, or 99% sequence identity to at least one of the β-TrCP1 amino acid sequence (SEQ ID NO:1) or the β-TrCP2 amino acid sequence (SEQ ID NO:4), and includes functionally equivalent derivates of β-TrCP1 and β-TrCP2 such as mutants, conjugates (including radiolabeled or chemically tagged β-TrCP1/2), fusion proteins, and fragments thereof, which retain the substrate specificity of a β-TrCP. "β-TrCP1/2" means "β-TrCP1 and/or β-TrCP2".

As used herein, a "β-TrCP inhibitor" is a compound or agent that causes one or more of the following: reducing β-TrCP1/2 expression, translation, or activity, or increasing β-TrCP1/2 degradation.

A "cell division cycle 25A" or "Cdc25A" protein herein means a protein comprising a peptide sequence corresponding at least to residues 82-88 of human wild-type Cdc25A (with reference to the full sequence, SEQ ID NO:12). Preferably, the peptide sequence comprises a sequence corresponding to residues 80-93 of human wild-type Cdc25A (with reference to the full sequence, SEQ ID NO:12). To function as a substrate for a β-TrCP, the serine residues corresponding to residues 82 and 88 of SEQ ID NO:12 must be at least phosphorylated, preferably double phosphorylated. Exemplary Cdc25A fragments useful for testing binding to or ubiquitination by β-TrCP1/2 include peptides corresponding to residues 73-95 of SEQ ID NO:12 and residues 80-93 of SEQ ID NO:12.

A "DNA damaging agent" is a chemical compound or treatment method that induces DNA damage when applied to a cell, including single-strand breaks, double-strand breaks and alkylation. Such agents include, without limitation, ionizing radiation and waves that induce DNA damage, such as γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Contemplated chemotherapeutic agents include alkylating agents such as mitomycin C, adozelesin, cis-platinum, and nitrogen mustard.

"Ubiquitin ligation", "ubiquitination", and "ubiquitinylation" as used herein all refer to the addition of a ubiquitin polypeptide to a protein substrate targeted for degradation.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Administration

In the case of the present invention, parenteral routes of administration are also possible. Such routes include intravenous, intra-arteriole, intramuscular, intradermal, subcutaneous, intraperitoneal, transmucosal, intranasal, rectal, vaginal, or transdermal routes. If desired, inactivated therapeutic formulations may be injected, e.g., intravascular, intratumor, subcutaneous, intraperitoneal, intramuscular, etc. In a preferred embodiment, the route of administration is oral.

Although there are no physical limitations to delivery of the formulation, oral delivery is preferred because of its ease and convenience, and because oral formulations readily accommodate additional mixtures, such as milk and infant formula.

Adjuvant

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet heniocyanins, and potentially useful human adjuvants such as N-acetyl-muramyl-L-threonyl-D-isogltitamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphoryloxy)-ethylamine, BCG (bacille Calmette-Guerin) and *Corynebacterium parvum*. Preferably, the adjuvant is pharmaceutically acceptable.

Amplification

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E.W. Martin.

Coding Sequence or a Sequence Encoding an Expression Product

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually, but not always, ATG) and a stop codon.

Dosage

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences." By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells, and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., *Cell* 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. Coli*.

Immune Response

An "immune response" refers to the development in the host of a cellular and/or antibody-mediated immune response to a composition or vaccine of interest. Such a response usually consists of the subject producing antibodies, B cells, helper T cells, suppressor T cells, and/or cytotoxic T cells directed specifically to an antigen or antigens included in the composition or vaccine of interest.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., $3^{rd}$ ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., 3$^{rd}$ ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO$_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual*, 2$^{nd}$ ed., vol. 2, ch. 9.50, CSH Laboratory Press, 1989; Ausubel et al. (eds.), 1989, *Current Protocols in Molecular Biology*, Vol. 1, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Patient or Subject

"Patient" or "subject" refers to mammals and includes human and veterinary subjects.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, *Proc. Natl. Acad. Sci. USA* 1990, 87:2264, modified as in Karlin and Altschul, *Proc. Nail. Acad. Sci. USA* 1993, 90:5873-5877. Such an algorithm is incorporated into the NBLAST and XBLAST programs of Altschul et al., *J. Mol. Biol.* 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., *Nucleic Acid. Res.* 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, *CABIOS* 1988; 4: 11-17. Such an algorithm is incorporated into the ALIGN program (version 2.0), which is part of the GCG sequence alignment software package. When utilizing the ALIGN program for comparing amino acid sequences, a PAM 120 weight residue table, a gap length penalty of 12, and a gap penalty of 4 can be used.

In a preferred embodiment, the percent identity between two amino acid sequences is determined using the algorithm of Needleman and Wunsch (*J. Mol. Biol.* 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Pharmaceutically Acceptable

When formulated in a pharmaceutical composition, a therapeutic compound such as an inhibitor of one or more of β-TrCP1/2 or RSK1/2 can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine, including treating food allergies and related immune disorders.

In a preferred embodiment, the pharmaceutical composition is conveniently administered as an oral formulation. Oral dosage forms are well known in the art and include tablets, caplets, gelcaps, capsules, and medical foods. Tablets, for example, can be made by well-known compression techniques using wet, dry, or fluidized bed granulation methods.

Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in die pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

The term "therapeutically effective amount" is used herein to mean an amount or dose sufficient to modulate, e.g., increase or decrease as appropriate, the expression or activity level of a desired protein e.g., by about 10 percent, preferably by about 50 percent, and more preferably by about 80-90 percent. In certain embodiments, the amount of BimEL is increased as a result of decreasing the amount of β-TrCP1, β-TrCP2, RSK1, or RSK2. Preferably, a therapeutically effective amount is sufficient to cause an improvement in a clinically significant condition in the host following a therapeutic regimen involving one or more β-TrCP1, β-TrCP2, RSK1, or RSK2 inhibitors. The concentration or amount of the active ingredient depends on the desired dosage and administration regimen, as discussed below. Suitable dosages may range from about 0.01 mg/kg to about 100 mg/kg of body weight per day, week, or month. The pharmaceutical compositions may also include other biologically active compounds.

According to the invention, a therapeutically effective amount of a β-TrCP1, β-TrCP2, RSK1, or RSK2 inhibitor can be formulated in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Optionally, the β-TrCP1, β-TrCP2, RSK1, or RSK2 inhibitor can be formulated together with an DNA damaging agent such as an alkylating agent.

In another embodiment, the active ingredient can be delivered in a vesicle, in particular a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound(s) can be delivered in a controlled release system. For example, a polypeptide may be administered using, intravenous infusion with a continuous pump, in a polymer matrix such as poly-lactic/glutamic acid (PLGA), a pellet containing a mixture of cholesterol and the active ingredient (Silastic®; Dow Corning, Midland, Mich.; see U.S. Pat. No. 5,554,601) implanted subcutaneously, an implantable osmotic pump, a transdermal patch, liposomes, or other modes of administration.

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

Kits

The invention provides a kit for screening for an agent useful for increasing inhibiting β-TrCP1, β-TrCP2, RSK1, or RSK2 activity, comprising: a BimEL protein, at least one β-TrCP protein, a means for detecting binding between the BimEL and β-TrCP protein, optionally packaged in association with instructions teaching one or more of the methods described herein. In certain embodiments, the invention provides a kit for screening for an agent useful for increasing the amount of BimEL protein comprising: a BimEL protein, at least one β-TrCP protein, RSK1, or RSK2 protein, a means for detecting binding between the BimEL and the β-TrCP, RSK1, or RSK2 protein, optionally packaged in association with instructions teaching one or more of the methods described herein.

Polynucleotide or Nucleotide Sequence

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thiouracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radio-isotopes, fluorescent molecules, biotin, and the like.

Promoter

The promoter sequences may be endogenous or heterologous to the host cell to be modified, and may provide ubiquitous (i.e.+, expression occurs in the absence of an apparent external stimulus) or inducible (i.e., expression only occurs in presence of particular stimuli) expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981; 290:304-310), the promoter contained in the 3' long terminal repeat of Rous sarcoma virus (Yamamoto, et al., Cell 1980; 22:787-797), the herpes thymidine kinase promoter (Wagner et al., Proc. Natl. Acad. Sci. USA 1981; 78:1441-1445), the regulatory sequences of the metallothionein gene (Brinster et al., Nature 1982; 296:39-42); prokaryotic promoters such as the alkaline phosphatase promoter, the trp-lac promoter, the bacteriophage lambda $P_L$ promoter, the T7 promoter, the beta-lactamase promoter (Villa-Komaroff, et al., Proc. Natl. Acad. Sci. USA 1978; 75:3727-3731), or the tac promoter (DeBoer, et al., Proc. Natl. Acad. Sci. USA 1983; 80:21-25); see also "Useful proteins from recombinant bacteria" in Scientific American 1980; 242:74-94; promoter elements from yeast or other fungi such as the Gal4 promoter, the ADC (alcohol dehydrogenase) promoter, and the PGK (phosphoglycerol kinase) promoter.

Small Molecule

The term "small molecule" refers to a compound that has a molecular weight of less than about 2000 Daltons, less than about 1000 Daltons, or less than about 500 Daltons. Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

Substantially Homologous or Substantially Similar

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

Substantially Identical

By "substantially identical" is meant a polypeptide or nucleic acid molecule exhibiting at least 80%, more preferably at least 90%, and most preferably at least 95% identity in comparison to a reference amino acid or nucleic acid sequence. For polypeptides, the length of sequence comparison will generally be at least 20 amino acids, preferably at least 30 amino acids, more preferably at least 40 amino acids, and most preferably at least 50 amino acids. For nucleic acid molecules, the length of sequence comparison will generally be at least 60 nucleotides, preferably at least 90 nucleotides, and more preferably at least 120 nucleotides.

The degree of sequence identity between any two nucleic acid molecules or two polypeptides may be determined by sequence comparison and alignment algorithms known in the art, including but not limited to BLAST, FASTA, DNA Strider, and the GCG Package (Madison, Wis.) pileup program (see, for example, Gribskov and Devereux Sequence *Analysis Primer* (Stockton Press: 1991) and references cited therein). The percent similarity between two nucleotide sequences may be determined, for example, using the Smith-Waterman algorithm as implemented in the BESTFIT software program using default parameters.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

Therapeutically or Prophylactically Effective Amount of an Antibody

The compositions of the invention may include a "therapeutically effective amount" or a "prophylactically effective amount" of an antibody or antigen-binding portion of the desired inhibitor. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Transfection

By "transfection" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection.

Treating or Treatment

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof, or (3) relieving the disease, i.e., causing regression of the state, disorder or condition or at least one of its clinical or sub-clinical symptoms.

The benefit to a subject to be treated is either statistically significant or at least perceptible to the patient or to the physician.

Variant

The term "variant" may also be used to indicate a modified or altered gene, DNA sequence, enzyme, cell, etc., i.e., any kind of mutant.

Vector, Cloning Vector and Expression Vector

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol. 1996; 178:1216-1218).

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), "nt" means nucleotide, and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

Expression BimEL, β-TrCP1/2, and RSK1/2 and Related Substrates

For the screening and evaluation of compounds for their ability to modulate the BimEL interaction with 13β-TrCP1/2, RSK1/2, or other β-TrCP substrates, both in vitro (including reconstituted systems) and in vivo systems (including cellular systems and transgenic animals) systems can be used. Regardless of the screening or testing system of choice, various expression methods can be employed to provide the protein components or cellular/transgenic animals to be used in the method.

A wide variety of host/expression vector combinations (i.e., expression systems) may be employed in expressing DNA sequences for BimEL, β-TrCP1 or fragments or mutants thereof, β-TrCP2 or fragments or mutants thereof, RSK1/2 or fragments or mutants thereof, Cdc25A or fragments or mutants thereof, Skp1, Cul1, β-catenin, Emi1, IκB-α, IκB-β, IκB-ε, and other components to be included. These may be co-expressed from the same vector, expressed from different vectors, or one may be expressed while the other one is added externally to the screening or evaluation system. Useful expression vectors, for example, may consist of segments of chromosomal, non chromosomal and synthetic DNA sequences. Suitable vectors include derivatives of SV40 and known bacterial plasmids, e.g., *E. Coli* plasmids col E1, pCR 1, pBR322, pMal-C2, pET, pGEX (Smith et al., Gene, 1938; 67:3140), pMB9 and their derivatives, plasmids such as RP4; phage DNAS, e.g., the numerous derivatives of phage 1, e.g., NM989, and other phage DNA, e.g., M 13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, various tumor cells lines can be used in expression systems of the invention.

Yeast expression systems can also be used according to the invention to express any protein of interest. For example, the non-fusion pYES2 vector (XbaI, SphI, ShoI, NotI, GstXI, EcoRI, BstXI, BamHI, SacI, KpnI, and HindIII cloning site; Invitrogen) or the fusion pYESHisA, B, C (XbaI, SphI, ShoI, NotI, BstXI, EcoRI, BamHI, SacI, KpnI, and HindIII cloning site, N-terminal peptide purified with ProBond resin and cleaved with enterokinase; Invitrogen), for example, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature, 1981; 290:304-310), the promoter contained in the 3' long terminal repeat of Rous sarcoma virus (Yamamoto, et al., Cell, 1980; 22:787-797), the herpes thymidine kinase promoter (Wagner et al., Proc. Natl. Acad. Sci. U.S.A., 1981; 78:1441-1445), the regulatory sequences of the metallothionein gene (Brinster et al., Nature, 1982; 296:39 42); prokaryotic expression vectors such as the β-lactamase promoter (Villa-Komaroff, et al., Proc. Natl. Acad. Sci. U.S.A., 1978; 75:3727-3731), or the tac promoter (DeBoer, et al., Proc. Natl. Acad. Sci. U.S.A., 1983; 80:21-25); see also "Useful proteins from recombinant bacteria" in Scientific American, 1980; 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature, 1985; 315:338-340; Kollias et al., Cell, 1986; 46:89-94), hematopoietic stem cell differentiation factor promoters, erythropoietin receptor promoter (Maouche et al., Blood, 1991; 15:2557), etc.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992; 7:980-990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991; 2:320-330), defective herpes virus vector lacking a glycoprotein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest., 1992; 90:626-630; see also La Salle et al., Science, 1993; 259:988-990); and a defective adeno-associated virus vector (Samulski et al., J. Virol., 1987; 61:3096-3101; Samulski et al., J. Virol., 1989; 63:3822-3828; Lebkowski et al., Mol. Cell. Biol., 1988; 8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine 1995). In that regard, it is advantageous to employ a viral vector that is engineered to express a minimal number of antigens.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem., 1992; 267:963-967; Wu and Wu, J. Biol. Chem., 1988; 263:14621-14624; Hartmut et al., Canadian Patent Application No. 2,012,311, filed Mar. 15, 1990; Williams et al., Proc. Natl. Acad. Sci. USA, 1991; 88:2726-2730). Receptor-mediated DNA delivery approaches can also be used (Curiel et al., Hum. Gene Ther., 1992; 3:147-154; Wu and Wu, J. Biol. Chem., 1987; 262:4429-4432). U.S. Pat. Nos. 5,580,859 and 5,589,466 disclose delivery of exogenous DNA sequences, free of transfection facilitating agents, in a mammal. A relatively low voltage, high efficiency in vivo DNA transfer technique, termed electrotransfer, has also been described (Mir et al., C. P. Acad. Sci., 1998; 321:893; WO 99/01157; WO 99/01158; WO 99/01175).

Another option is to transcribe and translate cDNA sequences in vitro. Various commercial systems are available for such techniques, including the TNT Quick Coupled Transcription/Translation System with Transcend™ (Promega, Madison, Wis.). For in vitro production of labeled or modified peptides or proteins, labeled or chemically modified amino acid precursors such as, e.g., $^{35}S$-methionine or phosphoserine, can be added to the translation system.

Transgenic Animals

Transgenic mammals can be prepared for evaluating the interaction of human BimEL and β-TrCP1/2, RSK1/2, or any other β-TrCP1/2 substrates. Such mammals provide excellent models for screening or testing drug candidates, i.e., inhibitors of at least one of β-TrCP1/2 or RSK1/2. Thus, human BimEL "knock-in" mammals can be prepared for evaluating the molecular biology of this system in greater detail than is possible with human subjects. In one embodiment, the animal can be double-transgenic, in that both human BimEL and human β-TrCP1/2 or RSK1/2 are expressed in the transgenic animal. It is also possible to evaluate compounds or diseases in "knock-out" animals, e.g., to identify a compound that can compensate for a defect in BimEL, or β-TrCP1/2 or RSK1/2. Both technologies permit manipulation of single units of genetic information in their natural position in a cell genome and to examine the results of that manipulation in the background of a terminally differentiated organism. Trangenic mammals can be prepared by any method, including but not limited to modification of embryonic stem (ES) cells and heteronuclear injection into blast cells.

A "knock-in" mammal is a mammal in which an endogenous gene is substituted with a heterologous gene (Roemer en al., New Biol., 1991; 3:331). Preferably, the heterologous gene is "knocked-in" to a locus of interest, either the subject of evaluation (in which case the gene may be a reporter gene; see Elefanty et al., Proc. Natl. Acad. Sci. USA, 1998; 95:11897) of expression or function of a homologous gene, thereby linking the heterologous gene expression to transcription from the appropriate promoter. This can be achieved by homologous recombination, transposon (Westphal and Leder, Curr. Biol., 1997; 7:530), using mutant recombination sites (Araki et al., Nucleic Acids Res, 1997; 25:868) or PCR (Zhang and Henderson, Biotechniques, 1998; 25:784).

A "knock-out mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al., (Genes and Development, 1995; 9-2623 34) describes PPCA knock out mice. The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. Generally, for homologous recombination, the DNA will be at least about 1 kilobase (kb) in length and preferably 3-4 kb in length, thereby providing sufficient complementary sequence for recombination when the knockout construct is introduced into the genomic DNA of the ES cell.

Double knock-out mammals can be generated by repeating the procedures set forth herein for generating each knock-in or knock-out construct, or by breeding to mammals, each with a single gene knocked out, to each other, and screening for those with the double knockout genotype. Regulated knockout animals can be prepared using various systems, such as the tet-repressor system (see U.S. Pat. No. 5,654,168) or the Cre-Lox system (see U.S. Pat. No. 4,959,317 and No. 5,801,030). The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

In another series of embodiments, transgenic animals are created in which (i) a human BimEL, β-TrCP1/2, RSK1, or RSK2 is stably inserted into the genome of the transgenic animal; and/or (ii) the corresponding endogenous genes are inactivated and replaced with their human counterparts (see, e.g., Coffman, Semin. Nephrol., 1997; 17:404; Esther et al., Lab. Invest., 1996; 74:953; Murakami et al., Blood Press. Suppl., 1996; 2:36). Such animals can be treated with candidate compounds and monitored for neuronal development, neurodegeneration, or efficacy of a candidate therapeutic compound.

Antibodies to BimEL, β-TrCP1/2, RSK1, or RSK2

As described in the Examples, various antibodies useful for detecting BimEL, β-TrCP1/2, RSK1, or RSK2 or any of their substrates, have been produced, some of which are available commercially. Such antibodies may be used in immunoblotting or immunoprecipitation techniques to study binding of β-TrCP1/2, RSK1, or RSK2 or to another one of its substrates, to detect ubiquitinated Cdc25A, to inhibit interaction between BimEL and β-TrCP1/2, RSK1, or RSK2 or one of its other substrates, or for other purposes in the screening and treatment methods described herein. Additional antibodies with different specificity or other particular properties may also be prepared. Antibodies useful for these purposes include but are not limited to polyclonal, monoclonal, chimeric, single chain, Fab fragments, and Fab expression library.

Various procedures known in the art may be used for the production of polyclonal antibodies. For example, various host animals can be immunized by injection with the antigenic polypeptide, including but not limited to rabbits, mice, rats, sheep, goats, etc. For preparation of monoclonal antibodies, any technique that provides for the production of antibody molecules by continuous cell lines in culture may be used. These include but are not limited to the hybridoma technique originally developed by Kohler and Milstein (Nature, 1975; 256:495-497), as well as the trioma technique, the human B-cell hybridoma technique (Kozbor et al., Immunology Today, 1983, 4:72, Cote et al., Proc. Natl. Acad. Sci. U.S.A., 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec., 1989).

According to the invention, techniques described for the production of single chain antibodies (U.S. Pat. Nos. 5,476,786 and 5,132,405 to Huston; U.S. Pat. No. 4,946,778) can be adapted to produce polypeptide-specific single chain antibodies. Indeed, these genes can be delivered for expression in vitro to, e.g., express an antibody inhibiting USP47 interaction with β-TrCP1/2. An additional embodiment of the invention utilizes the techniques described for the construction of Fab expression libraries (Huse et al., Science, 1989; 246: 1275-1281) to allow rapid and easy identification of monoclonal Fab fragments with the desired specificity for a PTPN11 polypeptide, or its derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Screening

A "test substance" or "test compound" is a chemically defined compound or mixture of compounds (as in the case of a natural extract or tissue culture supernatant), whose ability to modulate BimEL activity or amount or that modulates the activity or the amount of β-TrCP1/2, RSK1, or RSK2 the a may be defined by various assays. A "test substance" is also referred to as a "candidate drug" or "candidate compound" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech, 1996; 14:60).

A modulatory effect may be determined by an in vitro method using a recombinant BimEL or β-TrCP1/2, RSK1, or RSK2 reporter gene promoter activity system. Reporter genes for use in the invention encode detectable proteins, and include, but are by no means limited to, chloramphenicol transferase (CAT), β-galactosidase (O-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, the test substance has modulated, e.g., increased BimEL-mediated gene expression, or decreased β-TrCP1/2, RSK1, or RSK2 expression, the test substance is a candidate for development as an agent capable of inducing apoptosis or cell death. Likewise, any such modulator is a candidate for use as a tumor sensitizing agent. The reporter gene assay system described herein may be used in a high-throughput primary screen for antagonists, or it may be used as a secondary functional screen for candidate compounds identified by a different primary screen, e.g., a binding assay screen that identifies compounds that decrease β-TrCP1/2, RSK1, or RSK2 transcription activity, and/or increase BimEL activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing genes encoding at least one of BimEL, β-TrCP1/2, RSK1/2, and/or Cdc25A, and optionally also any of the remaining components of an SCF complex, can be used in screening methods to identify candidate drugs. In one series of embodiments, a permanent cell line is established. Alternatively, cells are transiently programmed to express a BimEL gene by introduction of appropriate DNA or mRNA. As described herein, transgenic animals can also be used to screen for or study agents that increase the level of BimEL. Similarly, it may be desirable for cells to be transiently programmed to express any of the genes encoding β-TrCP1/2, RSK1/2, or Cdc25A by introduction of appropriate DNA or mRNA. As described herein, transgenic animals can also be used to screen for or study agents that increase the level of one or more of β-TrCP1/2, RSK1/2, or Cdc25A.

Identification of candidate substances can be achieved using any suitable assay, including without limitation (i) assays that measure selective binding of test compounds to BimEL, to the BimEL binding site on β-TrCP1/2, or RSK1/2 or another one of its substrates (ii) assays that measure the ability of a test substance to modify (e.g., inhibit) a measurable activity or function of at least one of β-TrCP1/2, or RSK1/2, (iii) assays that measure the ability of a substance to modify (i.e., inhibit) the transcriptional activity of sequences derived from the promoter (i.e., regulatory) regions of at least one of the genes encoding β-TrCP1/2, or RSK1/2; and (iv) assays that modulate (e.g., promote) the degradation of at least one of β-TrCP1/2, or RSK1/2 proteins, while increasing the level of BimEL.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

Test compounds useful in the present invention include, among others, siRNA molecules discussed below and small molecule inhibitors of β-TrCP1, β-TrCP2, RSK1, and/or RSK2. Non-limiting examples of suitable small molecule RSK inhibitors include, among others, molecules described in PCT Publication Nos. WO 2003/020722 and WO 2009/040512, including BI-D1870 (Sapkota et al., Biochem. J., 2007, 401:29-38); compounds described in US Patent Publication No. 20070049539, including SL0101 (Smith et al., Cancer Res., 2005, 65:1027-34); compounds described in US Patent Publication No. US 20070082884, including FMK (Cohen et al., Science, 2005, 308:1318-21) as well as additional compounds described in Ngyuen, Anti-Cancer Agents in Medicinal Chemistry, 2008, 8, 710-716.

RNA Interference (RNAi or siRNA)

Another technique of interest for therapeutic purposes is based on the same principles employed for interfering with at least one of β-TrCP1/2, or RSK1/2 translation in a cellular system, namely siRNA technology. Particularly, expression of selected genes can be suppressed in human cells by transfecting with exogenous, short RNA duplexes (siRNA) where one strand corresponds to a target region of the mRNA, i.e., EST of interest (Elbashir et al., Nature, 2001; 411:494-498). The siRNA molecules are typically greater than 19 duplex nucleotides, and upon entry into the cell, siRNA causes the degradation of single-stranded (ssRNAs) RNAs of identical sequences, including endogenous mRNAs. siRNA is more potent than standard anti-sense technology since it acts through a catalytic mechanism. Effective strategies to deliver siRNAs to target cells in cell culture include physical or chemical transfection. An alternative strategy uses the endogenous expression of siRNAs by various Pol III promoter expression cassettes that allow transcription of functional siRNAs or their precursors (Scherr et al., Curr. Med. Chem., 2003; 10(3):245-56). Recently, the RNA-polymerase III dependent promoter (H1-RNA promoter) was inserted in the lentiviral genome to drive the expression of a small hairpin RNA (shRNA) against enhanced green fluorescent protein (Abbas-Turki et al., Hum. Gene Ther., 2002; 13(18):2197-201). siRNA can also be delivered in a viral vector derived, e.g., from a lentivirus (Tiscornia et a/, Proc. Natl. Acad. Sci. U.S.A., 2003; 100:1844-8). For review articles, see Ilannon, Nature, 2002; 418:244-51 and Bernstein et al., RNA, 2001; 7(11):1509-21. This technology also has been described in vitro in cultured mammalian neurons in Krickevsky and Kosik, Proc. Natl. Acad. Sci. USA, 2002; 99(18):11926-9. siRNA technology is also being used to make transgenic animals (Cornell et al., Nat. Struct. Biol., 2003; 10(2):91-2). RNA is described in Publication Nos. WO 99/49029 and WO 01/70949.

Exemplary siRNA's suitable for β-TrCP1/2, or RSK1/2 include:

```
for human β-TrCP1/2:
GUGGAAUUUGUGGAACAUC        (SEQ ID NO: 19)

for mouse β-TrCP1/2:
AUCAAGAUCAGGGAUAAAA        (SEQ ID NO: 20)

for human RSK1:
CCCAACAUCAUCACUCGAAA       (SEQ ID NO: 21)

for human RSK2:
AGCGCUGAGAAUGGACAGCAA.     (SEQ ID NO: 22)
```

Materials and Methods

The following describes the materials and methods employed in Example 1.

Cells. HeLa (from ATCC) and U2OS (from ATCC) cells were cultured essentially as described in Donzelli et al. (EMBO J., 2002; 21:4875-84). Cells were grown at 37° C. in a 5% $CO_2$ atmosphere in Dulbecco's modified Eagle's medium (Euroclone) supplemented with 10% bovine calf serum (Hyclone) and 2 mM L-glutamine (Euroclone), or in DMEM containing 5% fetal calf serum (FCS, from GIBCO). HEK293 (from ATCC), Bim−/− MEFs and Bax−/−; Bak−/− immortalized mouse embryo fibroblasts (MEFs) (from Dr. Huang at The Walter and Eliza Hall Institute of Medical Research, Australia; see Bouillet et al., Science, 1999, 286: 1735-1738; Lindsten et al., Mol. Cell, 2000, 6:1389-1399) were maintained in Dulbecco's modified Eagle's medium (DMEM) containing 10% fetal bovine serum (FBS, from GIBCO). H1650 and HCC827 cells (both from ATCC) were maintained in RPMI-1640 medium (GIBCO) containing 10% FBS. Primary thymocytes were obtained from 6 week Bim+/+ or Bim−/− mice. Thymi were harvested and single cell suspensions obtained by passing through a fine mesh sieve. Thymocytes were maintained in high-glucose DME (GIBCO) supplemented with 250 mM L-asparagine, 50 μM mercaptoethanol, and 10% FCS.

Purification and activation of primary human CD4+ T cells. Peripheral blood mononuclear cells (PBMCs) from healthy donors were isolated from leukopacks (New York Blood Center) using Ficoll-Paque Plus (Amersham Biosciences, NJ). Samples were depleted of adherent cells by plastic adherence in complete medium (RPMI 1640 medium supplemented with 10% FCS, 2 mM L-glutamine, 100 U/ml penicillin) for 1 hour at 37° C. Non-adherent cells were collected and naïve CD4+ T cells were enriched using a negative selection magnetic beads kit (Miltenyi Biotech, CA). The cell composition (>85% naïve CD4+) was confirmed by flow cytometry. The naïve CD4+ T cells were then activated on plates coated with anti-CD3 and anti-CD28 antibodies (BD Pharmingen, CA). After 48 hours, the cells were transferred to new plates at a density of $1\times10^6$ cells/ml and supplemented with 100 U/ml IL-2 (NIH).

Cycloheximide Treatment. To inhibit protein synthesis, cells were cultured in the presence of 10 μg/ml cycloheximide for the indicated time points. Inhibition of protein synthesis in metaphase-arrested cells was achieved as follows: cells were treated with 0.05 μg/ml nocodazole for 16 hours, and rounded cells were collected by gentle pipetting and cultured further with 0.05 μg/ml nocodazole and 10 μg/ml cycloheximide for up to 120 minutes. Inhibition of protein synthesis in cells exiting mitosis was achieved as follows: nocodazole-arrested cells were released in drug-free medium for 1 hour and cultured further with 10 μg/ml cycloheximide for up to 60 minutes.

Transient Transfections and Retrovirus-Mediated Gene Transfer. Transfections using the calcium phosphate and retrovirus-mediated gene transfer were performed essentially as described in Dorrello et al., Science, 2006, 314:467-471.

$CaPO_4$ Transfection. The following protocol describes transfection in a 24-well plate. On Day 1, cells were seeded at $5\times10^5$ cells/well, and left in medium containing fetal calf serum (FCS). On Day 2, cells were re-feed cells with 1 ml fresh medium containing FCS. A DNA precipitate was prepared by mixing 47.5 μl 1×TBS (TBS: 8 g NaCl, 0.2 g KCl, 3 g Tris base, in 1 L, pH 7.4)| with 20 μl DNA (500 μg/ml), and 7.5 μl 2.5 M $CaCl_2$. The above mix was added to 75 μl 2×HBS (8 g NaCl, 6 g HEPES, 0.2 g $Na_2HPO_4$ (anhydrous) per 500 ml, pH 7.1, sterile-filtered). The precipitate was then added directly to the medium on cells, and the cells incubated for 3 hours at 37° C. The medium was removed, and 1 ml 15% glycerol in PBS (8 g NaCl, 0.2 g KCl, 1.44 g $Na_2HPO_4$, 0.24 g $KH_2PO_4$ in 1 L, pH 7.4, autoclaved) was added to each well. After 1 minute, the glycerol was removed, taking great care not to dislodge cells (some cell types become less well attached after glycerol shock), and the cells washed with PBS or serum free medium. One ml growth medium was added, and left at 37° C. for 6-72 hours.

Plasmids. Flag- and His-tagged β-TrCP1/2, RSK1/2, BimEL, and Cdc25A mutants were generated using the QuickChange Site-directed Mutagenesis kit (Stratagene, La Jolla, Calif.). All constructs were verified by DNA sequencing. Both wild-type BimEL and BimEL mutants were subcloned into the pBabe retroviral vector (obtained from Dr. Weinberg laboratory at the Whitehead Institute for Biomedical Research, Cambridge, Mass.; see Hahn et al., Mol Cell Biol. 2002, 22:2111-2123). Flag-tagged constructs encoding full-length or truncated versions of β-TrCP1/2, RSK1/2, or Cdc25A were generated as follows: the full-length cDNA for β-TrCP1/2, RSK1/2, or Cdc25A was obtained as a PCR product from pRC-CMV-X (where X is the desired gene) and was cloned into the EcoRV restriction site of pcDNA3.1-FlagA; the 51-CT mutant was generated by PvuII-XhoI digestion of the full-length flagged construct and the insertion of the fragment into EcoRV-XhoI-digested FlagB-plasmid; and the 170-CT was produced by BglII-XhoI digestion of the full-length flagged construct and the insertion of the fragment into BamHI-XhoI-digested FlagB-plasmid. pCDNA3.1-Flag-X point mutants were generated using the QuikChange Site-directed Mutagenesis kit (Stratagene). All constructs are verified by DNA sequencing.

Cell Lysis. This procedure was used to lyse cells prior to immunoblotting and immunoprecipitation. Each plate was rinsed once with cold PBS (5 ml for a 100 mm plate), and aspirated off. The plates were placed on ice and 1 ml of lysis buffer (see below) added. When lysis became apparent, keeping the lid on, the plate was held partially open with one hand while tilting the plate to one side. Using a pipette, buffer was aspirated and re-released until the particulate cellular matter accumulated in the pool. Each of the lysates was collected into centrifuge tubes, and spun at maximum speed for 5-10 minutes at 4° C. to pellet cell debris. 50 to 100 μl of Protein A beads were added (in a 50% slurry, pre-washed with PBS) to new centrifuge tubes. The cell lysate supernatants were transferred to the new tubes, and placed at 4° C. for 20 to 30 minutes (pre-clearing step). Preimmune sera or non-al sera was optionally used to further pre-clear the cell lysate as necessary. After the pre-clearing step, the lysate was spun in a microcentrifuge for 5 minutes at low speed (4000-5000 rpm) to pellet the beads. The supernatant was used for immunoprecipitation. Lysis buffer: Nonidet P-40 lysis buffer (NP-40 LB). NP-40: 50 mM Tris-HCl (pH 7.5), 150 mM NaCl, 0.5% NP-40, and 50 mM NaF). Immediately before use, the following 100× stocks were added to the lysis buffer: 100 mM NaVO$_3$ in ddH$_2$O, 100 mM DTT in ddH$_2$O, 100 mM PMSF in 100% isopropyl alcohol, and 100× Protease inhibitor (2.5 mg/ml Leupeptin, 2.5 mg/ml Aprotinin, 100 mM (=15 mg/ml) Benzamidine, and 1 mg/ml Trypsin inhibitor in ddH$_2$O.

Antibodies. The following antibodies were used for immunoblotting and/or immunoprecipitation: anti-Cdc25A (F6, Santa Cruz Biotechnology, Santa Cruz, Calif.); anti-Flag (M2, Sigma); anti-Cul1 (Zymed, San Francisco, Calif.); anti-Skp1 (1C10F4, Zymed), anti-βTrCP1 (rabbit polyclonal antibodies from Bethyl Laboratories; monoclonal antibody from Invitrogen), anti-βTrCP2 (N-15, Santa Cruz); anti-Emi1 antibody (provided by P. K. Jackson at Stanford University School of Medicine, CA, USA); anti-Bim (Zymed, San Francisco Calif. and Invitrogen); anti-phospho-Bim(Ser69) (Biosource); anti-phosphor-Bim(Ser93/94/98) (designed by Dr. Pagano's laboratory at NYU, produced by YenZym Antibodies); anti-ERK1/2 (Zymed, San Francisco Calif.); anti-phosphor-ERK1/2 (Thr185/Tyr187) (Biosource, CA); anti-RSK1 (Zymed San Francisco Calif.); anti-phosho-RSK (Ser380) (Cell signaling Technology); anti-Mcl1 (Santa Cruz, #sc-20679); anti-Hsp70 (Santa Cruz). Gefitinib was from LC Laboratories.

Immunoprecipitation. The desired antibody or antibodies (with or without competing peptides) were added as appropriate to fresh 1.5 ml Eppendorf tubes. Ppre-cleared cell lysate supernatant was added to the appropriate tubes, not carrying over any beads, and incubated at cold temperature for 2 hours to overnight. Pre-washed Protein A beads were added to each of the tubes, and placed in cold for 1 hour. The tubes were spun for 2 minutes at 2000 rpm to pellet the beads. The supernatants were aspirated and the pellets were washed with a large volume (1 ml) of lysis buffer per tube (i.e., lysis buffer without protease inhibitors). The tubes were spun for 2 minutes at 2000 rpm, and the supernatant aspirated as before. The procedure was repeated for a total of three washes. After the final aspiration, 10 µl of 2×SDS sample buffer was added to the lid of each tube, and the tubes were briefly spun to draw the sample buffer down to the pellet. The samples were boiled on a 100° C. heater for 4 minutes. All of the supernatant was loaded onto a SDS gel. For autoradiography, the gel was dried and developed via phospho-imaging (2 hours to an overnight exposure) and/or standard autoradiography (2 to 5 day exposure while stored at −80 degrees with enhancer screens).

Western Blotting (IP-Western). Immuno-blotting was conducted essentially as described in Donzelli et al. (2002), supra. Three pieces of the Whatman paper were wetted in Western transfer buffer (48 mM Tris Base, 39 mM Glycine, 0.0375% SDS, and 20% Methanol in ddH$_2$O), excess of buffer was removed and pieces were placed onto the platinum anode (BIO-RAD semi-dry trans-blot SD). The nitrocellulose was wetted in the same buffer and placed onto the Whatman paper. The gel was wetted in the transfer buffer for 5 to 10 seconds and placed onto the nitrocellulose. Three pieces of Whatman paper were wetted and, removing excess of buffer, placed onto the gel. Air bubbles were removed throughout this procedure. The trans-blot cathode was placed onto the stack. The gel was transferred at a constant voltage between 15 to 25V for 30 minutes.

The nitrocellulose was placed in staining solution (100 mill dH$_2$O and 1 ml Ponceau S solution (2 g Ponceau S, 30 ml trichloroacetic acid, 100 ml dH$_2$O) to stain for 2 to 5 minutes. The Ponceau S staining solution was poured out, and the nitrocellulose was rinsed twice with dH$_2$O. The dH$_2$O was poured out, and PBS was added to de-stain the nitrocellulose, with slow shaking until the protein bands disappeared (about 5 to 10 minutes). The PBS was poured out, and blocking solution (100 ml 1×PBS, 0.1 ml Tween-20, 5 g non-fat dry milk) was added to the nitrocellulose (30 to 50 ml per filter). The dish was placed on a shaker (slow) for at least 1 hour to overnight. The blocking solution was poured out, and the blot was rinsed once with PBS. The PBS was poured out, and enough blocking solution was added to cover the nitrocellulose. Also, the primary antibody was added. The dilution of antibody used was antibody-dependent. The range of dilution was from 1:5 (for some low titer monoclonal antibodies) to 1:5000. The dish was placed on a shaker (slow) for at least 1 hour to overnight at room temperature. The blot was transferred to a new dish and washed five to six times each for 10 minutes with 0.1% Tween-20 in PBS and slow shaking. Blocking solution and secondary antibody (e.g. horseradish peroxidase-conjugated mouse anti-rabbit antibody in a 1:10, 000 dilution if the primary antibody is of rabbit origin and the signal is to be detected by luminescence) were added to the nitrocellulose and slow shaking was continued for 1 hour at room temperature. The blot was washed 5 times for 10 minutes each with 0.1% Tween-20 in PBS and slow shaking as before. The blot was then washed once for 5 minutes with PBS and slow shaking.

The blot was developed using ECL detection reagents (RPN 2106, Amersham) by mixing equal volumes of each of the reagents in a fresh dish. The blot was placed in the mixture for exactly 1 minute, with frequent agitation, making sure all blot surfaces receive sufficient contact with the reagents. Saran-wrapped blot was then placed in an X-ray cassette, and using a timer, exposed to X-ray film for between 30 seconds to 5 minutes.

Phosphatase treatment. 500 units of λ protein phosphatase (New England Biolabs, Beverly, Mass.) were added to β-TrCP immunocomplexes in the presence of MgCl$_2$ for 30 minutes at 30° C.

Peptide binding assay. The peptides were coupled to agarose beads using the Aminolink Kit (Pierce, Rockford, Ill.). Coupled BimEL, β-TrCP1/2, RSK1/2, or Cdc25A peptides (10 mg) were incubated with $^{35}$S-methionine-labeled in vitro-translated β-TrCP1/2, FBXW2 or FBXW4, using the TNT-coupled reticulocyte lysate system (Promega, Madison, Wis.) in the presence of 5 µCi of $^{35}$S-labeled methionine (Amersham Biosciences, Piscataway, N.Y.). Agarose beads were washed with RIPA buffer and binding was assayed by SDS-PAGE followed by autoradiography.

Apoptosis Assay. Apoptosis was assessed using Annexin V-FITC and propidium iodide staining (BD Pharmigen).

siRNA. β-TrCP1/2 siRNA GUGGAAUUUGUGGAA-CAUC (SEQ ID NO:19) (Guardavaccaro et al., In vivo Dev Cell, 2003, 4:799-812; Margottin-Goguet cl al., Dev Cell, 2003; 4:813-26); RSK1 siRNA CCCAACAUCAUCACU-CUGAAA (SEQ ID NO:21) and RSK2 siRNA AGCGCUGAGAAUGGACAGCAA (SEQ ID NO:22) (Anjum et al., Curr Biol., 2005, 15:1762-7; Roux et al., J Biol. Chem., 2007, 282:14056-64). Control oligonucleotide was a dsRNA oligo to LacZ mRNA CGUACGCGGAAUACU-UCGA (SEQ ID NO:28). All siRNA oligonucleotides were from Dharmacon Research Inc. (Lafayette, Colo.). Cells were transfected with siRNA duplexes by Oligofectamine (Invitrogen, Carlsbad, Calif.), following manufacturer's instructions. Cells were transfected with the oligos twice (at 24 and 48 hours after plating) using oligofectamine (Invitrogen) for HEK293, HiPerFect (Qiagen) for NSCLC cell lines, or the AMAXA nucleofactor (Amaxa Inc. Gaithersburg, Md.) for CD4+ human T cell blasts at day 5, according to manufacturer's recommendations. 24 or 48 hours after the last transfection, cells were collected and analyzed.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Binding Characteristics of Human BimEL

Immunoprecipitation analysis identified human BimEL as a protein that interacts with the F-box protein β-TrCP. FIG. 1 shows human BimEL specifically binding to β-TrCP1 and β-TrCP2. For these binding studies, HEK293 cells were transfected with the indicated FLAG-tagged Fbw family F-box protein constructs (in FIG. 1). Twenty-four hours after transfection cells were treated for 3 hours with PMA (20 nM) and the proteasome inhibitor MG132 (10 μM) then harvested and lysed. Whole cell extracts (WCE) were subjected to immunoprecipitation using FLAG resin (α-FLAG), followed by immunoblotting with indicated antibodies (EV: empty vector). Lysates from transfected cells were immunoprecipitated using anti-FLAG constructs prior to Western blotting for BimEL, phosphorylated-BimEL(ser69) CUL1, and the FLAG epitope, as shown in FIG. 1.

β-TrCP1/2 bind to their substrates via phosphorylated residues located in a conserved motif (also termed a degron) which is composed of the sequence DpSGXXpS. A search for a β-TrCP1/2 degron sequence in BimEL, has identified the sequence $^{91}$RSSSGYFSFD$^{100}$ (SEQ ID NO:23), which contains a conserved motif similar to the canonical β-TrCP1/2 degron. These experiments confirmed that phosphorylation of the degron serines (93, 94, 98) are important for BimEL binding to β-TrCP1/2 by generating BimEL constructs where the relevant Serines are mutated to Alanines.

Figure 2A:
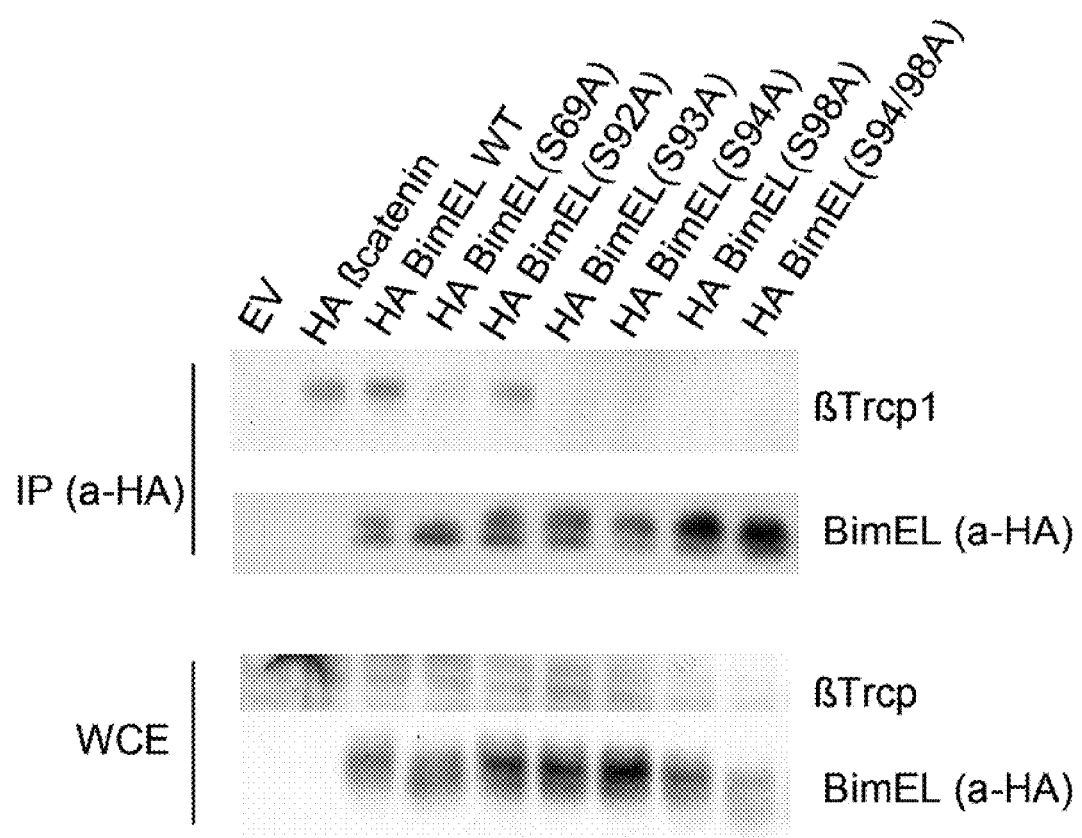

As depicted in FIG. 2A, Serine to Alanine mutation of Serines 93, 94, and 98 inhibited the interaction between β-TrCP1 and BimEL. Serine 69, which was previously demonstrated to be phosphorylated by ERK1/2 and to be important for BimEL's degradation, was also found to be important for BimEL binding to β-TrCP1/2. This result suggests that Serine 69 may function as a priming phosphorylation site, triggering the phosphorylation of the downstream serines 93, 94 and 98. This mode of action has been demonstrated in other known substrates of β-TrCP1/2 such as cdc25a and wee 1.

In the binding assays shown in FIG. 2A, HEK293 cells were transfected with empty vector, HA-β catenin (used as a positive control), HA-BimEL WT (lane 1-3), HA-BimEL (S69A) mutant (lane 4), or HA-BimEL (S94/98A) mutant (lane 5), or other HA-Bim phosphorylation mutants. Twenty-four hours after transfection, cells were treated for 3 hours with PMA and MG 132. Whole cell extracts (WCE) were subjected to immunoprecipitation using HA resin (α-HA) followed by immunoblotting with indicated antibodies. The presence of Ser69 stimulates phosphorylation of the downstream serine residues. The results show that Ser93, Ser94 and Ser98 are required for BimEL interaction with β-TrCP1.

FIG. 2B shows that phosphorylation of Serines 93, 94 and 98 is necessary for the interaction between β-TrCP1 and BimEL. In this experiment in vitro binding assays were performed using in, vitro translated β-TrCP1 and a purified BimEL peptide composed of 13 amino-acids containing the degron motif. The in vitro binding assays were performed between $^{35}$S-labeled in vitro transcribed/translated β-Trcp1, Fbxw2 and Fbxw4 and beads-coupled BimEL peptide $^{88}$CLSRSSSGYFSFD$^{100}$ (SEQ ID NO:24) or BimEL phosphopeptide $^{88}$CLSRSpSpSGYFpSFD$^{100}$ (SEQ ID NO:25). Bound proteins were eluted and subjected to electrophoresis and autoradiography. FIG. 2B shows βTrCP1 binds specifically to the phosphorylated peptide.

Serines 93, 94 and 98 were also shown to be phosphorylated in vivo following activation of ERK by either serum addition or PMA (FIG. 2C). In this experiment, BimEL from cells treated with PMA as well as from cells released from serum starvation were immunoprecipitated. In the experiments in FIG. 2C, cells were serum deprived (SD) for 24 hours, serum released (SR) for 10 minutes (lane 2) or treated with PMA for 10 minutes (lane 3-5). Whole cell extracts (WCE) were subjected to immunoprecipitation using HA resin (α-HA) followed by immunoblotting for β-TrCP1, and antiHA (for BimEL). Using an antibody that specifically recognizes BimEL forms that are phosphorylated on these three Serines, BimEL's degron was found to be phosphorylated in vivo in response ERK1/2 activation induced by either PMA or serum addition. Moreover, Serine 69 phosphorylation is required for phosphorylation of the degron Serines as their phosphorylation significantly decreased when Serine 69 is mutated to Alanine (FIG. 2C). These data also show that in vivo phosphorylation of BimEL on Ser93/94/98 is rapidly induced by serum or PMA.

Figure 3:
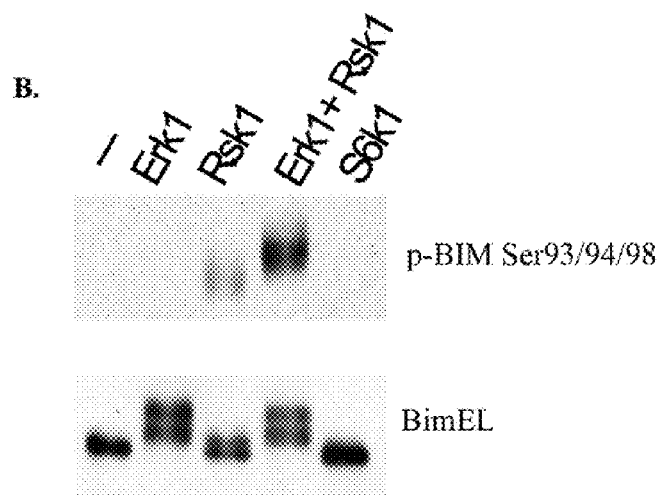
FIG. 3A shows RSK substrates and their representative phosphorylation sites IκBα (SEQ ID NO:15), BAD (SEQ ID NO:16), DAPK (SEQ ID NO:17), and BIM (SEQ ID NO:1)
FIG. 3B shows immunoblots of in vitro phosphorylation assays.
FIG. 3C illustrates HEK293 cells transfected with RSK and BimEL constructs and immunoblots showing RSK1 binding to BimEL.
Figure 3:
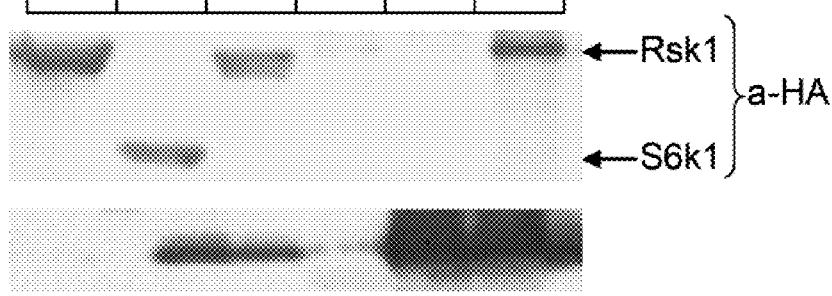

In addition RSK1/2 were identified as the kinases that phosphorylate BimEL on the degron serines. RSK family of kinases are activated by ERK and were demonstrated to phosphorylate substrates on a site identical to BimEL's degron. FIG. 3A shows known RSK substrates and their representative phosphorylation sites IκBα (SEQ ID NO:15), BAD (SEQ ID NO:16), DAPK (SEQ ID NO:17), and BIM (SEQ ID NO:18). In addition, many of the RSKs known substrates are involved in apoptosis. A kinase assay using bacterially purified BimEL and commercially available purified kinases was performed. FIG. 3B shows that RSK1 phosphorylates BimEL in vitro on serines 93/94/98 (the degron serines). Incubating RSK1 together with ERK1 enhances BimEL phosphorylation, most likely due to phosphorylation of Serine 69 by ERK which facilitates phosphorylation of the downstream kinases. In contrast, ERK1 by itself or S6K1 (a kinase downstream of the PI3K signalling pathway that has the same phosphorylation site as RSK1) did not promote BimEL's phosphorylation on serines 93/94/98. In addition, these results demonstrate that BimEL specifically binds to RSK1 (FIG. 3C).

To show that βTrCP1/2 and RSK1/2 control the protein levels of BimEL, siRNA experiments were performed. When βTrCP1/2 is silenced (FIG. 4A) or RSK1/2 is silenced (FIG. 4B), BimEL's degradation (induced with PMA) is inhibited.

Figure 4:
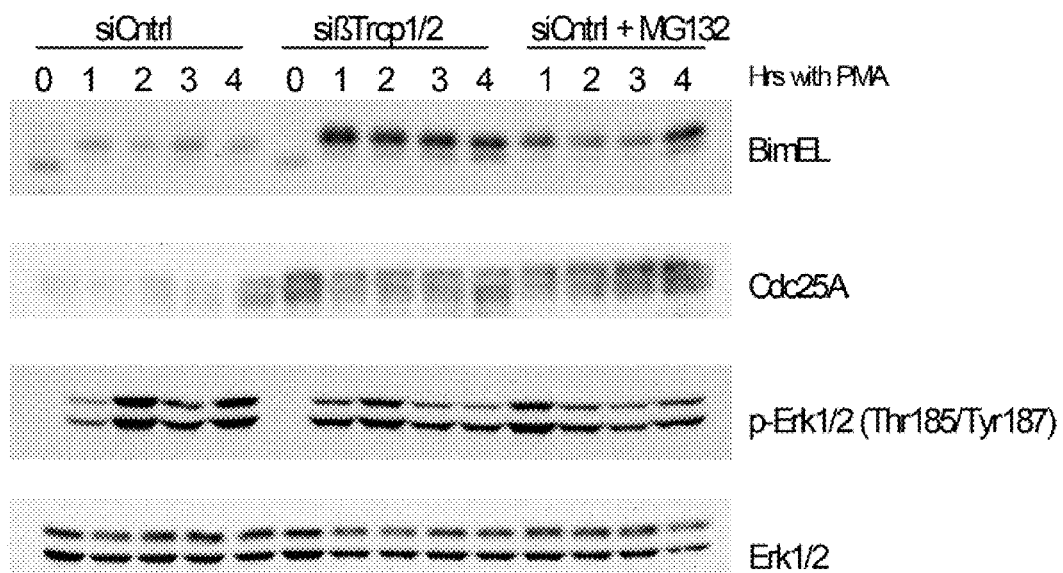
FIGS. 4A-B are Western blots of siRNA reactions showing when βTrCP1/2 is silenced (A) or RSK1/2 (B) is silenced, BimEL's degradation as induced with PMA is inhibited.
Figure 4:
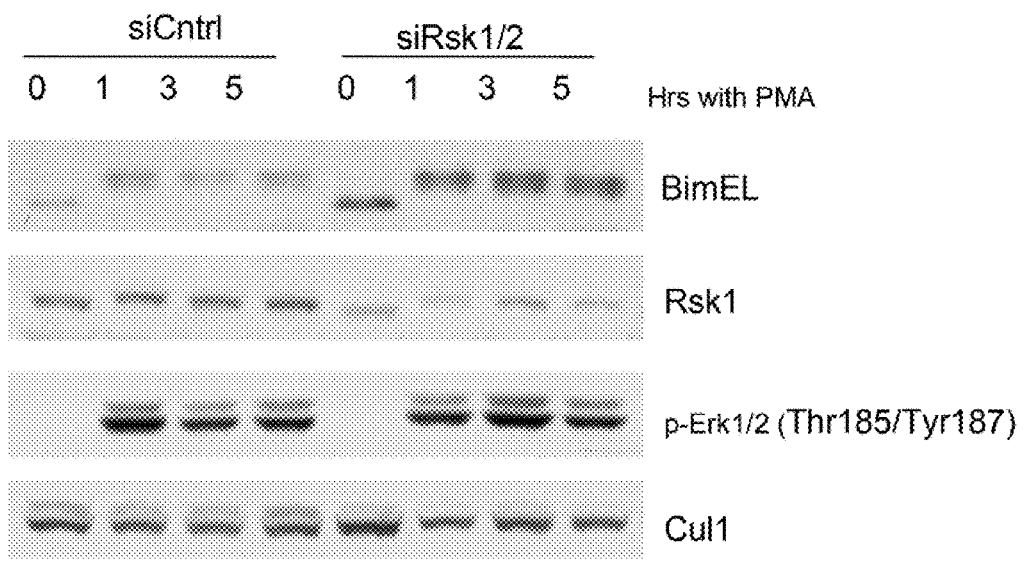
Figure 8:
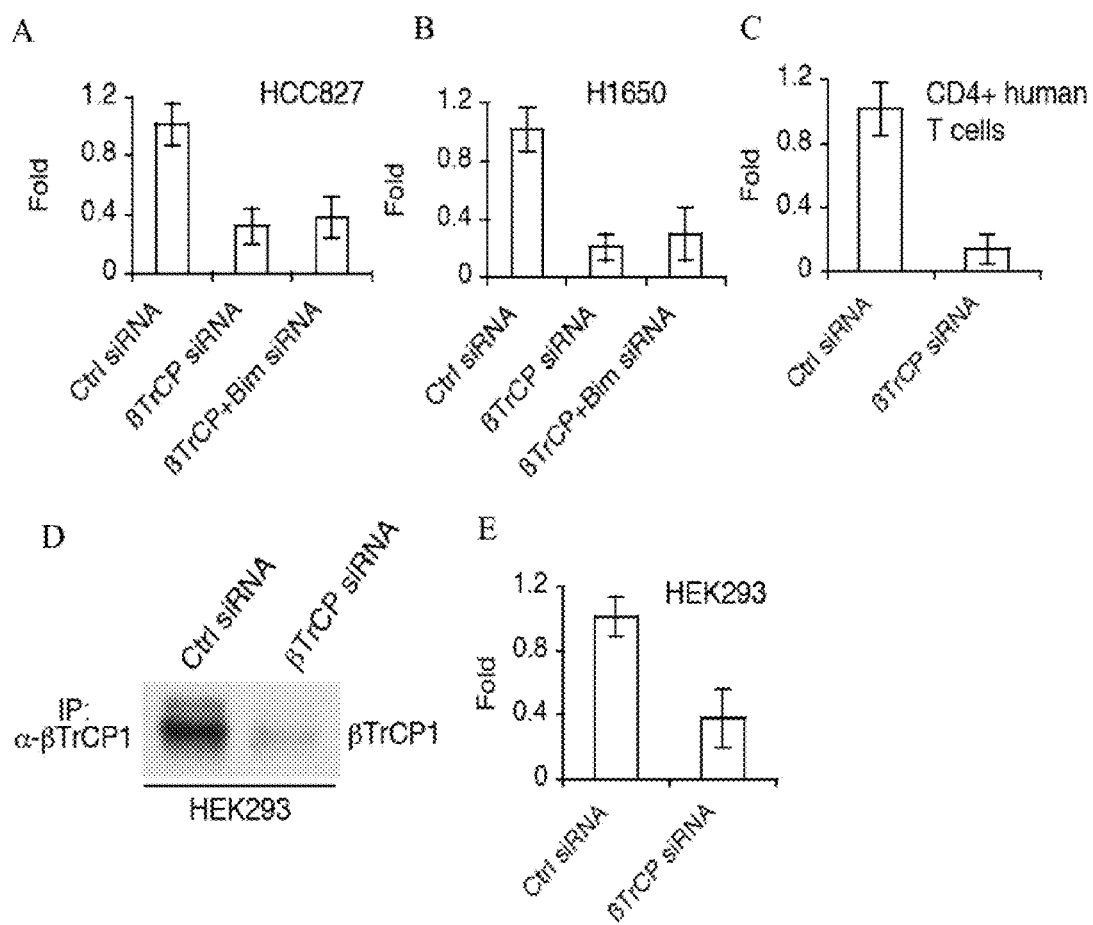
FIGS. 8A-E represent quantitative analysis of βTrCP1 mRNA in HEK293, HCC827, H1650 cell lines and CD4+ human T cells treated with an siRNA oligo targeting both βTrCP1 and βTrCP2 mRNAs (SEQ ID NO:19). Representative examples showing knockdown efficiency for βTrCP siRNA by RT-PCR analysis with oligo-dT-primed, reverse-transcribed cDNA derived from total RNA that was prepared from the indicated cells transfected with either control or βTrCP siRNAs. Quantitative PCR was conducted using locus-specific primers: forward GGCATTGCCTGTTTG-CAGTA (SEQ ID NO:29) and reverse GCACCACATTC-TATGTCCCA (SEQ ID NO:30) (n=3, ±SD). For HEK293 cells, knockdown efficiency was additionally analyzed by βTrCP1 immunoprecipitation and subsequent immunoblot analysis (D).

Inhibition of BimEL's degradation is also demonstrated in FIG. 4A by the use of the proteasome inhibitor MG132 (last 4 lanes). For the experiments shown in FIG. 4A, HEK293 cells were treated with control siRNA (SEQ ID NO:28) or siRNA targeting βTrcp1/2 (SEQ ID NO:19). 48 hours after siRNA treatment cells were treated with PMA or with PMA+ MG 132 (last four lanes) for indicated times. Protein extracts were immunoblotted for the indicated proteins. The accumulation of Cdc25A (a known βTrCP substrate) demonstrates efficient βTrCP knockdown (also confirmed by RT-PCR as shown in FIG. 8 for various cell lines). FIG. 4A shows that βTrCP silencing counteracted the effect of PMA on BimEL degradation, stabilizing BimEL.

For the experiments shown in FIG. 4B, HEK293 cells were treated with control siRNA (SEQ ID NO:28) or siRNA targeting RSK 1 (SEQ ID NO:21) and RSK2 (SEQ ID NO:22). 48 hours after siRNA treatment cells were treated with PMA for indicated times. Protein extracts were immunoblotted for the indicated proteins. FIG. 4B shows that RSK 1/2 silencing counteracted the effect of PMA on BimEL degradation, stabilizing BimEL.

Figure 6:
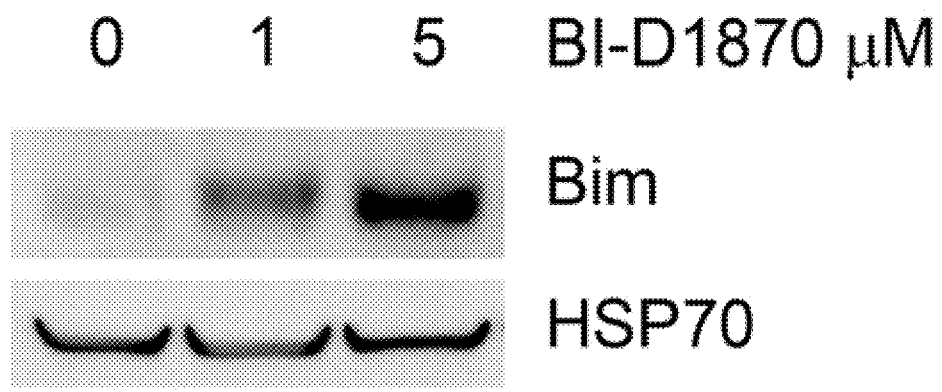
FIG. 6 demonstrates that pharmacological inhibition of RSK induces an accumulation of BimEL. MEFs were treated with 0, 1 and 5 μM BI-D1870 for 12 hours. Cell extracts were then immunoblotted for the Bim and HSP70 (control) proteins.

Similarly, as demonstrated in FIG. 6, specific pharmacological inhibition of RSK with BI-D1870 (Sapkota et al., Biochem. J., 2007, 401:29-38) induced BimEL accumulation.

The above data strongly support a model in which phosphorylation of BimEL on Ser93/Ser94/Ser98 mediates binding to βTrCP and degradation via $SCF^{\beta TrCP}$. Therefore, failure to bind βTrCP should result in stabilization of BimEL. To test this hypothesis, wild-type BimEL or BimEL(S94/98A) were transfected into HEK293 cells and subsequently treated with PMA and cycloheximide. In contrast to wild-type BimEL, BimEL(S94/98A), which does not bind βTrCP, was not degraded upon PMA treatment (FIG. 5A). Importantly, expression of BimEL(S94/98A) in immortalized $Bim^{-/-}$ mouse embryo fibroblasts (MEFs) triggered a much more robust apoptotic response than that obtained by expressing wild-type BimEL or even BimEL(S69A) (FIG. 5B). Neither wild-type BimEL nor BimEL mutants induced apoptosis in immortalized $Bak^{-/-}$; $Bax^{-/-}$ MEFs, confirming that BimEL (S94/98A)-dependent cell death occurs via the intrinsic mitochondrial pathway.

Figure 5C:
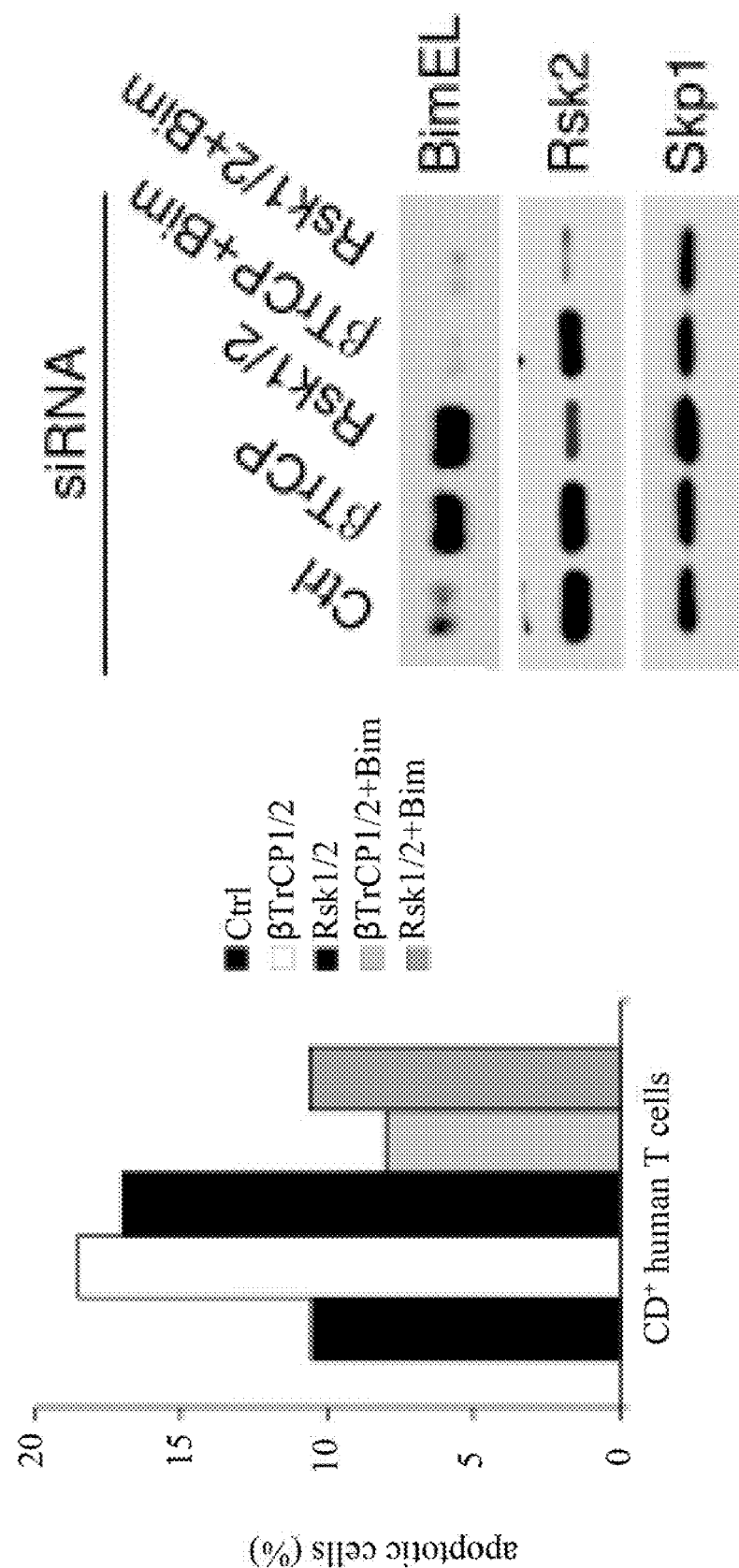
FIGS. 5A-F show that $SCF^{\beta TrCP}$- and Rsk-mediated degradation of BimEL controls the apoptotic response. (A) Mutation of Ser94/98 stabilizes BimEL despite ERK activation. Cells were transfected with either wild-type BimEL or BimEL(S94/98A) mutant. 24 hours posttransfection, cells were treated with PMA and cyclohexamide (CHX) for 0, 2, 4, 6, or 8 hours before immunoblotting for the indicated proteins. (B) Mutation of Ser94/98 augments the apoptotic activity of BimEL. $Bim^{-/-}$ and $Bax^{-/-}$; $Bak^{-/-}$ immortalized mouse embryo fibroblasts (MEFs) were infected with a retrovirus expressing either wild-type BimEL or different BimEL mutants. Apoptosis was measured 48 hours following infection using propidium iodide and Annexin V staining, with flowcytometric analysis (n=3, ±SD). (C) Silencing Rsk1/2 or βTrCP promotes Bim-dependent apoptosis in primary human T cells. Human T cells were transfected twice with the indicated siRNAs and collected 24 hours thereafter. Apoptosis (left panel) was determined as in (B), and cell extracts were analyzed by immunoblotting for the indicated proteins (right panel). (D) Silencing Rsk1/2 or βTrCP promotes apoptosis in NSCLC cells independent of their sensitivity to gefitinib. HCC827 and H1650 cells were transfected with the indicated siRNAs and collected at the indicated times. Apoptosis was determined as in (B) (n=3, ±SD). (E) Silencing Bim rescues apoptosis induced by downregualtion of Rsk1/2 or βTrCP. HCC827 and H1650 cells were treated with gefitinib for 24 hours or transfected with the indicated siRNAs and collected 48 hours thereafter. Apoptosis was determined as in (B) (n=3, ±SD). (F) HCC827 and H 1650 cells, treated as in (E), were collected, and cell extracts were analyzed by immunoblotting for the indicated proteins.
Figure 5:
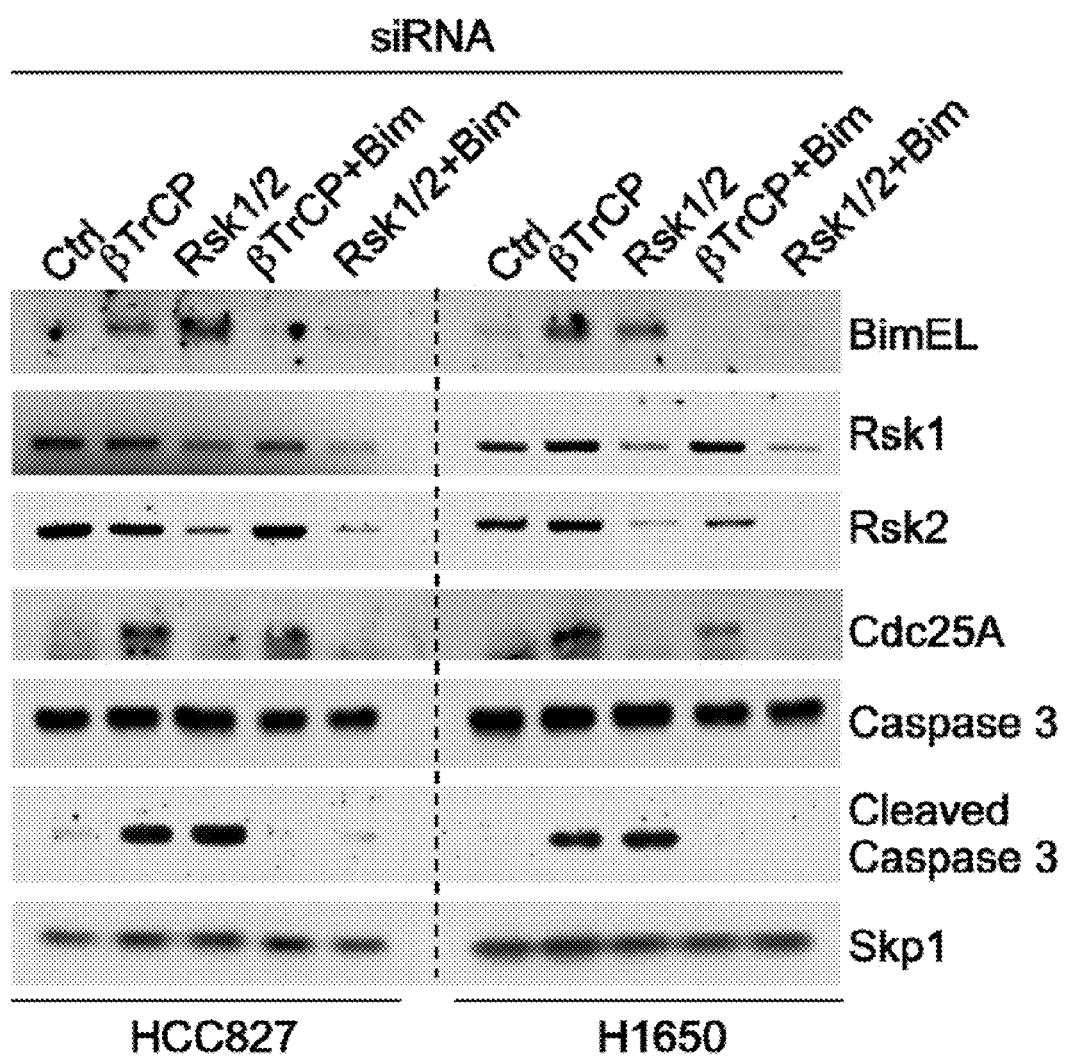
Figure 7:
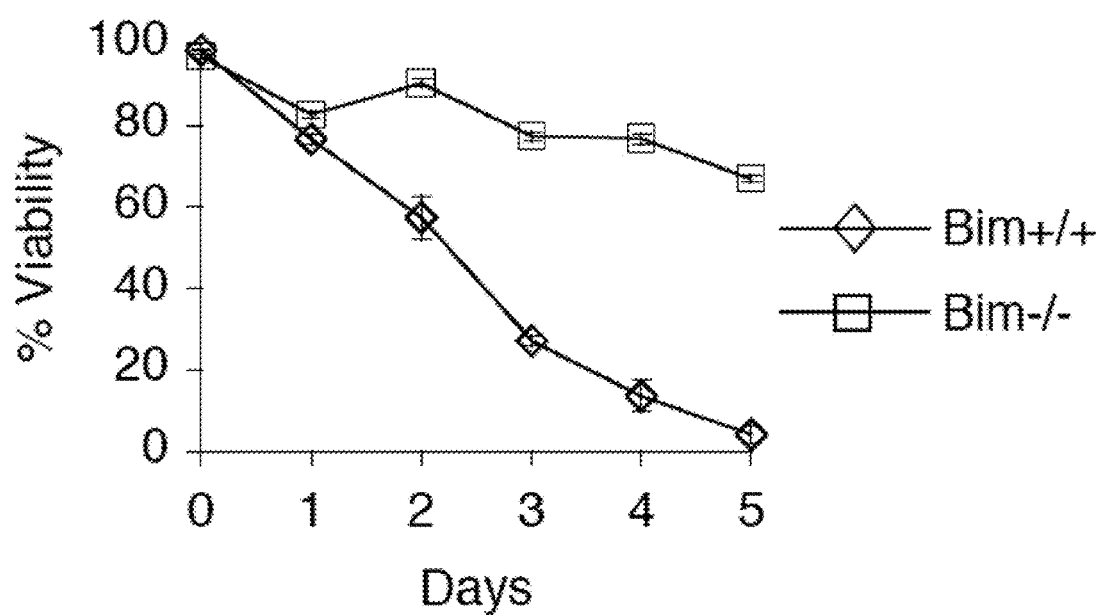
FIG. 7 demonstrates that pharmacological inhibition of RSK induces Bim-dependent cell death. Cell death was induced by addition of 10 mM BI-D1870 for 0-5 days in primary thymocytes obtained from Bim+/+ or Bim−/− mice. Cell viability was determined by flow cytometric analysis by staining the cells with propidium iodide. Cell debris was excluded from analysis based on its forward and sideward scatter characteristics. The experiment was performed in triplicate using 3 Bim+/+ and 2 Bim−/− mice for each experiment. Data shown are the means±1 SD.

It was also investigated whether RSK and TrCP mediate survival of primary human CD4+ T cells. FIG. 5C shows that the silencing of either Rsk1/2 or βTrCP in these cells resulted in BimEL accumulation and BimEL-mediated apoptosis (as demonstrated by the return of cell death to background levels when BimEL was downregulated together with Rsk1/2 or βTrCP). Accordingly, primary mouse T cells from wild-type mice, but not from $Bim^{-/-}$ mice, died in response to pharmacologic inhibition of RSK with BI-D1870 (FIG. 7).

To further study the biological significance of the βTrCP- and Rsk1/2-mediated degradation of BimEL, NSCLC cells that harbor activating mutations in the epidermal growth factor receptor (EGFR) were used. Initially, clinically relevant inhibitors of EGFR tyrosine kinase activity, such as gefitinib, trigger a BimEL-dependent apoptotic response in NSCLCs with EGFR mutations (Costa et al., 2007; Cragg et al., 2007; Deng et al., 2007b; Gong et al., 2007). However, these tumors eventually become resistant to tyrosine kinase inhibitors and lose their ability to die via BimEL upregulation. Two EGFR mutant NSCLC cell lines were examined: HCC827 (which are known to be sensitive to gefitinib) and H1650 (which are not) (see also FIG. 5E). Significantly, in the absence of gefitinib, apoptosis was promoted in both HCC827 and H1650 cells when either Rsk1/2 or βTrCP was downregulated (FIGS. 5D-F). When BimEL was also silenced, cell death returned to background levels (FIGS. 5E-F). Notably, upregulation of BimEL correlated with the induction of apoptosis in H1650 and HCC827 cells. These experiments showed that restoration of BimEL levels in cells harboring activating mutations in EGFR promotes apoptosis in both gefitinib-sensitive and gefitinib-insensitive NSCLC cells.

Discussion

Degradation of BimEL enables tumor cells to escape chemotherapy-induced apoptosis. The experimental results disclosed herein demonstrate that silencing of either βTrCP or Rsk 1/2 induces Bim-dependent apoptosis in NSCLC cells harboring activating mutations in EGFR, irrespective of their sensitivity to gefitinib. It follows that inhibition of RSK or βTrCP can be pursued as a therapeutic strategy to induce apoptosis of tumor cells in NSCLC and other malignancies such as, e.g., Bcr/Abl+ leukemias and melanomas (see, e.g., Kuribara et al., Mol. Cell. Biol., 2004, 24:6172-83; Kuroda et al., Proc. Natl. Acad. Sci. USA, 2006, 103:14907-12; Cartlidge et al., Pigment Cell Melanoma Res., 2008, 21:534-44; and Sheridan et al., J. Biol. Chem., 2008, 283:22128-35).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for increasing the level of BimEL (Bcl-2-Interacting Mediator of cell death, Extra Long isoform) protein in a cell comprising
   (a) contacting the cell with an effective amount of (i) an inhibitor of β-TrCP1 and an inhibitor of β-TrCP2 or (ii) an inhibitor of RSK1 and an inhibitor of RSK2, and
   (b) detecting an increase in the level of BimEL protein in the cell (i) as compared to the level of BimEL protein in the cell prior to administration of the inhibitor(s) or (ii) as compared to the level of BimEL protein in a control cell in the absence of the inhibitor(s).

2. The method of claim 1, wherein the cell is a diseased or abnormal cell from a tissue or a cell line that exhibits a disease or abnormal condition selected from the group consisting of cancer, infection, immune disorder, cardiovascular disease, and inflammatory disorder.

3. The method of claim 1, further comprising contacting the cell with a second agent for sensitizing the cell to DNA damage, or for inducing apoptosis or cell death of the cell.

4. The method of claim 1, wherein the inhibitor of β-TrCP1, β-TrCP2, RSK1, or RSK2 is an siRNA molecule.

5. The method of claim 4, wherein the siRNA molecule comprises the sequence selected from the group consisting of SEQ ID NO:19, SEQ ID NO:20, SEQ ID NO:21, and SEQ ID NO:22.

6. The method of claim 4, wherein the siRNA molecule consists of the sequence selected from the group consisting of SEQ ID NO:19, SEQ ID NO:20, SEQ ID NO:21, and SEQ ID NO:22.

* * * * *

UNITED STATES PATENT AND TRADEMARK OFFICE
CERTIFICATE OF CORRECTION

PATENT NO. : 8,093,043 B2
APPLICATION NO. : 12/478003
DATED : January 10, 2012
INVENTOR(S) : Michele Pagano and Elinor Dehan Page 1 of 1

It is certified that error appears in the above-identified patent and that said Letters Patent is hereby corrected as shown below:

In the Specification

Column 1, Lines 15-21 should read:
--STATEMENT REGARDING FEDERALLY SPONSORED RESEARCH OR DEVELOPMENT
This invention was made with government support under grant numbers R01 GM057587, R37 CA076584, and R21 CA125173 awarded by The National Institutes of Health and under grant number W81XWH-06-1-0377 awarded by the Department of Defense.
The government has certain rights in the invention.--

Signed and Sealed this
Sixth Day of December, 2022

Katherine Kelly Vidal
*Director of the United States Patent and Trademark Office*

SEQUENCE LISTING

<160> NUMBER OF SEQ ID NOS: 30

<210> SEQ ID NO 1
<211> LENGTH: 605
<212> TYPE: PRT

-continued

<213> ORGANISM: Homo sapiens

<400> SEQUENCE: 1

```
Met Asp Pro Ala Glu Ala Val Leu Gln Glu Lys Ala Leu Lys Phe Met
1               5                   10                  15
Cys Ser Met Pro Arg Ser Leu Trp Leu Gly Cys Ser Ser Leu Ala Asp
            20                  25                  30
Ser Met Pro Ser Leu Arg Cys Leu Tyr Asn Pro Gly Thr Gly Ala Leu
        35                  40                  45
Thr Ala Phe Gln Asn Ser Ser Glu Arg Glu Asp Cys Asn Asn Gly Glu
    50                  55                  60
Pro Pro Arg Lys Ile Ile Pro Glu Lys Asn Ser Leu Arg Gln Thr Tyr
65                  70                  75                  80
Asn Ser Cys Ala Arg Leu Cys Leu Asn Gln Glu Thr Val Cys Leu Ala
                85                  90                  95
Ser Thr Ala Met Lys Thr Glu Asn Cys Val Ala Lys Thr Lys Leu Ala
            100                 105                 110
Asn Gly Thr Ser Ser Met Ile Val Pro Lys Gln Arg Lys Leu Ser Ala
        115                 120                 125
Ser Tyr Glu Lys Glu Lys Glu Leu Cys Val Lys Tyr Phe Glu Gln Trp
    130                 135                 140
Ser Glu Ser Asp Gln Val Glu Phe Val Glu His Leu Ile Ser Gln Met
145                 150                 155                 160
Cys His Tyr Gln His Gly His Ile Asn Ser Tyr Leu Lys Pro Met Leu
                165                 170                 175
Gln Arg Asp Phe Ile Thr Ala Leu Pro Ala Arg Gly Leu Asp His Ile
            180                 185                 190
Ala Glu Asn Ile Leu Ser Tyr Leu Asp Ala Lys Ser Leu Cys Ala Ala
        195                 200                 205
Glu Leu Val Cys Lys Glu Trp Tyr Arg Val Thr Ser Asp Gly Met Leu
    210                 215                 220
Trp Lys Lys Leu Ile Glu Arg Met Val Arg Thr Asp Ser Leu Trp Arg
225                 230                 235                 240
Gly Leu Ala Glu Arg Arg Gly Trp Gly Gln Tyr Leu Phe Lys Asn Lys
                245                 250                 255
Pro Pro Asp Gly Asn Ala Pro Asn Ser Phe Tyr Arg Ala Leu Tyr
            260                 265                 270
Pro Lys Ile Ile Gln Asp Ile Glu Thr Ile Glu Ser Asn Trp Arg Cys
        275                 280                 285
Gly Arg His Ser Leu Gln Arg Ile His Cys Arg Ser Glu Thr Ser Lys
    290                 295                 300
Gly Val Tyr Cys Leu Gln Tyr Asp Asp Gln Lys Ile Val Ser Gly Leu
305                 310                 315                 320
Arg Asp Asn Thr Ile Lys Ile Trp Asp Lys Asn Thr Leu Glu Cys Lys
                325                 330                 335
Arg Ile Leu Thr Gly His Thr Gly Ser Val Leu Cys Leu Gln Tyr Asp
            340                 345                 350
Glu Arg Val Ile Ile Thr Gly Ser Ser Asp Ser Thr Val Arg Val Trp
        355                 360                 365
Asp Val Asn Thr Gly Glu Met Leu Asn Thr Leu Ile His His Cys Glu
    370                 375                 380
Ala Val Leu His Leu Arg Phe Asn Asn Gly Met Met Val Thr Cys Ser
385                 390                 395                 400
Lys Asp Arg Ser Ile Ala Val Trp Asp Met Ala Ser Pro Thr Asp Ile
```

```
                    405                 410                 415
Thr Leu Arg Arg Val Leu Val Gly His Arg Ala Ala Val Asn Val Val
        420                 425                 430

Asp Phe Asp Asp Lys Tyr Ile Val Ser Ala Ser Gly Asp Arg Thr Ile
            435                 440                 445

Lys Val Trp Asn Thr Ser Thr Cys Glu Phe Val Arg Thr Leu Asn Gly
    450                 455                 460

His Lys Arg Gly Ile Ala Cys Leu Gln Tyr Arg Asp Arg Leu Val Val
465                 470                 475                 480

Ser Gly Ser Ser Asp Asn Thr Ile Arg Leu Trp Asp Ile Glu Cys Gly
                485                 490                 495

Ala Cys Leu Arg Val Leu Glu Gly His Glu Glu Leu Val Arg Cys Ile
        500                 505                 510

Arg Phe Asp Asn Lys Arg Ile Val Ser Gly Ala Tyr Asp Gly Lys Ile
            515                 520                 525

Lys Val Trp Asp Leu Val Ala Ala Leu Asp Pro Arg Ala Pro Ala Gly
    530                 535                 540

Thr Leu Cys Leu Arg Thr Leu Val Glu His Ser Gly Arg Val Phe Arg
545                 550                 555                 560

Leu Gln Phe Asp Glu Phe Gln Ile Val Ser Ser Ser His Asp Asp Thr
                565                 570                 575

Ile Leu Ile Trp Asp Phe Leu Asn Asp Pro Ala Ala Gln Ala Glu Pro
        580                 585                 590

Pro Arg Ser Pro Ser Arg Thr Tyr Thr Tyr Ile Ser Arg
            595                 600                 605

<210> SEQ ID NO 2
<211> LENGTH: 6146
<212> TYPE: DNA
<213> ORGANISM: Homo sapiens

<400> SEQUENCE: 2
taagagaggg cgggggggaag gaagaggagg cgggatccgg gcgctgcgtt ggctgcggcc      60
tggcaccaaa ggggcggccc cggcggagag cggacccagt ggcctcggcg attatggacc     120
cggccgaggc ggtgctgcaa gagaaggcac tcaagtttat gtgctctatg cccaggtctc     180
tgtggctggg ctgctccagc ctggcggaca gcatgccttc gctgcgatgc ctgtataacc     240
cagggactgg cgcactcaca gctttccaga attcctcaga gagagaagac tgtaataatg     300
gcgaaccccc taggaagata taccagaga agaattcact tagacagaca tacaacagct     360
gtgccagact ctgcttaaac caagaaacag tatgtttagc aagcactgct atgaagactg     420
agaattgtgt ggccaaaaca aaacttgcca atggcacttc cagtatgatt gtgcccaagc     480
aacgaaaact ctcagcaagc tatgaaaagg aaaaggaact gtgtgtcaaa tactttgagc     540
agtggtcaga gtcagatcaa gtggaatttg tggaacatct tatatcccaa atgtgtcatt     600
accaacatgg gcacataaac tcgtatctta aacctatgtt gcagagagat ttcataactg     660
ctctgccagc tcggggattg gatcatattg ctgagaacat tctgtcatac ctggatgcca     720 atcactatg tgctgctgaa cttgtgtgca aggaatggta ccgagtgacc tctgatggca     780
tgctgtggaa gagcttatc gagagaatgg tcaggacaga ttctctgtgg agaggcctgg     840
cagaacgaag aggatgggga cagtatttat tcaaaaacaa acctcctgac gggaatgctc     900
ctcccaactc ttttttataga gcactttatc ctaaaattat acaagacatt gagcaaatag     960
aatctaattg gagatgtgga agacatagtt tacagagaat tcactgccga agtgaaacaa    1020
```

```
gcaaaggagt ttactgttta cagtatgatg atcagaaaat agtaagcggc cttcgagaca    1080
acacaatcaa gatctgggat aaaaacacat tggaatgcaa gcgaattctc acaggccata    1140
caggttcagt cctctgtctc cagtatgatg agagagtgat cataacagga tcatcggatt    1200
ccacggtcag agtgtgggat gtaaatacag gtgaaatgct aaacacgttg attcaccatt    1260
gtgaagcagt tctgcacttg cgtttcaata atggcatgat ggtgacctgc tccaaagatc    1320
gttccattgc tgtatgggat atggcctccc caactgacat tacctccgg agggtgctgg    1380 tcggacaccg agctgctgtc aatgttgtag actttgatga caagtacatt gtttctgcat    1440
ctggggatag aactataaag gtatggaaca caagtacttg tgaatttgta aggaccttaa    1500
atggacacaa acgaggcatt gcctgtttgc agtacaggga caggctggta gtgagtggct    1560
catctgacaa cactatcaga ttatgggaca tagaatgtgg tgcatgttta cgagtgttag    1620
aaggccatga ggaattggtg cgttgtattc gatttgataa caagaggata gtcagtgggg    1680
cctatgatga aaaaattaaa gtgtgggatc ttgtggctgc tttggacccc cgtgctcctg    1740
cagggacact ctgtctacgg acccttgtgg agcattccgg aagagttttt cgactacagt    1800
ttgatgaatt ccagattgtc agtagttcac atgatgacac aatcctcatc tgggacttcc    1860
taaatgatcc agctgcccaa gctgaacccc cccgttcccc ttctcgaaca tacacctaca    1920
tctccagata aataaccata cactgacctc atacttgccc aggacccatt aaagttgcgg    1980
tatttaacgt atctgccaat accaggatga gcaacaacag taacaatcaa actactgccc    2040
agtttccctg gactagccga ggagcagggc tttgagactc ctgttgggac acagttggtc    2100
tgcagtcggc ccaggacggt ctactcagca caactgactg cttcagtgct gctatcagaa    2160
gatgtcttct atcttttgtg aatgattgga acttttaaac ctcccctcct ctcctccttt    2220
cacctctgca cctagttttt tcccattggt tccagacaaa ggtgacttat aaatatattt    2280
agtgttttgc cagaatctct cttgctttgc cattaagcag aagaactagt ttccctgtat    2340
agcctgctgg gagagaccca cttctagggt atgggggatg cagcttcaag cccagtgccc    2400
agtgtctccc tgttaactgc aggaatgcca agcacctggc cagagcagcc cagccccaat    2460
atgcttagga ggagacagag ttccctctgt atagcctctg ggacaagaaa aagaaaacac    2520
aagaatgtat acactggaag atttgggcct cctgcctgcc ttctcttgt ttctgttcct    2580 cttcccatct actcccctac gcccctccaa ccttttttct ctgtctgctt cacctgagaa    2640
gaaagtgtac gaagagagtg tcctcctctc acatgagcca gatcagccag aaaatgcaac    2700
acttggaaga gttaaatgct gttcagtgaa gatttcagcc ccaggccttt gctgcaagtg    2760
accctgtggc aacagtggat tctcagacat gatactctca tcatatttgc aactcttctc    2820
tctctttctt ccccacaccc aagaggagga ttggtggtag gggcaggca gagggggtgg    2880 ggagaagttt cctgggctcc atcaatggct gcatctttc tggactcagc agtctccttg    2940
attccatgta gagtgtggaa aggagttgct gattgcattt cctctcatta acaattgggt    3000
gtgtaataaa aagcattgta cttcatctta aatcactggt aaggctcagc ctacagaaag    3060
atttgaaatg gccagagcca atcgcttggt gcattctgcg taatggtttc catctccgat    3120
ttcctcatca gggcctgtga atacccaggt gcctgtatct ttgccaagac cgtgatcaag    3180
gtagcttaag agagatggtc aggagaaaac actgttttg tttttttgt tgttttgttt    3240 tgttttggcc agttaaatat catctctcaa atattgatct caccgtgtca accttgcact    3300
gcacaacctt cctctgctt ctcccacacc cagtatttgc agaagggcaa agctgcttaa    3360
gagagaggat cagggtgaag tttggcacac agggtttatt aatggggcaa aaactgcctt    3420
```

```
ttcttcctcc tcctgacctt attttgctct tcactctccc cagccaataa agcgtctgtg    3480
gcgattggtg aacagcataa acagctggac ctcagcaagg gtcaggcaaa cccagtcact    3540
cggaaggcag ctgtgtgagc tgccaagcta gtgggcttca ggtgcaaggg tacctgtgcc    3600
acaccaacct gggagcacac agaatactat taatgtgcac ccagctggtc tccccaggca    3660
agaaggtatc ctcttcccaa ggtgtaccca ctgaatgttg ttactacata ttgagagtca    3720
ttttatgcat atgcattcta ccttctcctgc tttatgagta tttttaagct tttagttcaa    3780
ggttatattc agaaaatatt tcccagtata atgatacatc gtagcctaag aaatattttc    3840
tcaatgtaat tcccttccca gctacccaaa tgctacagag aaatgttttc tacttggcca    3900
ctatcagggt tcgtcatcta ttgtgttgac tattaatggc ttttttgattg ggtaaggatt    3960 ttgctataga tgaaggtaga gggctgtcag ccctgaaaaa cacacaggtc agacatttaa    4020
aaggcatggg tttcgagctg tctcaaaata ttgcccaata gccataattt taccagcctt    4080
tctgtcatat gctgctatta caaagtgaaa gctgttgaat gtttattggt gcccaggggtt    4140 ttgctctcca atctaggttc agttgaagga atattgtttc taagactgtt ttgagacatg    4200
tccagtacat cacaaaggag atcggggcga cccctgcaga tgtggagcca ttagcccagt    4260
tgaggatatt ctccaagttg tcctctctcc tgctgatgga aatgggaatg aagttaagtg    4320
gtctgaaaaa cttgaatcgt tcacatttct cagctctggg ggtcatttac cagtttgttg    4380
tagaagaaat aatcaggtaa gttaaaagtt catttccaga gaaggtaaac cccacttacc    4440
atctctgcat gatttcagtg ggaattgatt atcactaatc cccaactggg ctagaataaa    4500
tgtaaagttt gaccttttta aaacgaaaag agagacaaag tctcagcaca ttccaaggag    4560
tggtagaaac agagctgaag gtgtccccat tgtagattag tctcttctca ctaaaattta    4620
ctttccaacg tagggcctaa aggaaacctt tcttaaagac aggctgaaac cccttcaaag    4680
gcagatgagg aggtacagac acgtgacctt ttggtgcaca ctggagctac ttggacaaga    4740
ccagcatgcc ttgctgcacg tgtgtgtatt tcactgctga gaacatcctt taacttggtg    4800
tgcaatttga aaggatgtga atcatggatg gaaggccatt tgtacatgtc ccttggcaaa    4860
attctttctg gtgtctccta acttcagaga cagggactct ttttggatct ctattgacaa    4920
gtaataaaag tctggccctc ataacttgtt tccgaactag aaaagtctgt gagaccccta    4980
catcattctg gttttttgc ttgagtaaga acaatccttt tttattttttc ttctgtacag    5040 tctaaagcta cagagaaaaa aaatgcact cttcccttgc cggctcctgg taccattggt    5100
ctgaacagct gtagttggtc tactccttac ttagcacttg attgtgtggg gaaacaaagg    5160
tgggaggggt ggggaatact ggaaataatc agggcaattt ttttctttcc cataattgga    5220
ctagatacct tggtactgtt gaccttctca gcatctccct tttgccttag atggcaacac    5280
cctccagtct gtagcagagc agtccaaccc agattagtgc agcccggagg cttagggtgc    5340
agcctccctg gtcttcctcc acacagttgt tcaccaacag accagacctc ctttaaccac    5400
agtgtcaaca tagtatcgga aagagagcca tttcttaggg gaataaaaca gtttcgcttc    5460
tttagctcat ctgtggtgtc agaatccttg gagctgaaga gagaaatcaa aagagcatga    5520
tgatggctgc ctggtttcag gtggaactta atgcattgat ctttagaagc tccttctgtt    5580
ggaagttgag tacctgtgat ctaaaatgtc ctggaggcag atgacatcta aaatatgtgc    5640
tttccaacca gcacagctgg cgctcttagc tcctgattgg ttgtgtgttt tattaaggat    5700
cagtgcagtt aagtcgtatt ttaaagtgtt acctcccctc ctaacccttc cccttccttgg   5760 acactgaagg aaaaggccaa ctagggtgtt agccctctgg gcaccaagga aactaacagc    5820
```

```
tttctcaaag cggtgaccac tcaggccagc ccagacaaat ctgagggatg gccagtgcac    5880
tccaatgatg ggacaggcct aacaacacat gtaagcttcc ccgagagctt tcagctggtt    5940
cacctctttg ttctctagac tcttaagtac tgactgcttt gacttttgtg attatgttat    6000
ggtgatgtgt agtcagtgta ccaatatgtt cacaacctag gatcatgata atggagtgtg    6060
ttttgggttt ttttttaactg ttcagaaaaa aagtaaatta caaatataag attaaagtga    6120
aaaaaaaaaa aaaaaaaaaa aaaaaa                                         6146

<210> SEQ ID NO 3
<211> LENGTH: 2151
<212> TYPE: DNA
<213> ORGANISM: Homo sapiens

<400> SEQUENCE: 3
tgcgttggct gcggcctggc accaaagggg cggccccggc ggagagcgga cccagtggcc      60
tcggcgatta tggaccccgc cgaggcggtg ctgcaagaga aggcactcaa gtttatgaat     120
tcctcagaga gagaagactg taataatggc gaaccccta ggaagataat accagagaag      180
aattcactta gacagacata caacagctgt gccagactct gcttaaaacca gaaacagta    240 tgtttagcaa gcactgctat gaagactgag aattgtgtgg ccaaaacaaa acttgccaat    300
ggcacttcca gtatgattgt gcccaagcaa cggaaactct cagcaagcta tgaaaaggaa    360
aaggaactgt gtgtcaaata ctttgagcag tggtcagagt cagatcaagt ggaatttgtg    420
gaacatctta tatcccaaat gtgtcattac caacatgggc acataaaactc gtatcttaaa   480 cctatgttgc agagagattt cataactgct ctgccagctc ggggattgga tcatatcgct    540
gagaacattc tgtcatacct ggatgccaaa tcactatgtg ctgctgaact tgtgtgcaag    600
gaatggtacc gagtgacctc tgatggcatg ctgtggaaga agcttatcga gagaatggtc    660
aggacagatt ctctgtggag aggcctggca gaacgaagag gatggggaca gtatttattc    720
aaaaacaaac ctcctgacgg gaatgctcct cccaactctt tttatagagc actttatcct    780
aaaattatac aagacattga gacaatagaa tctaattgga gatgtggaag acatagttta    840
cagagaattc actgccgaag tgaaacaagc aaggagtttt actgtttaca gtatgatgat    900
cagaaaatag taagcggcct tcgagacaac acaatcaaga tctgggataa aaacacattg    960
gaatgcaagc gaattctcac aggccataca ggttcagtcc tctgtctcca gtatgatgag   1020
agagtgatca taacaggatc atcggattcc acggtcagag tgtgggatgt aaatacaggt   1080
gaaatgctaa acacgttgat tcaccattgt gaagcagttc tgcacttgcg tttcaataat   1140
ggcatgatgg tgacctgctc caaagatcgt ccattgctg tatgggatat ggcctcccca   1200
actgacatta ccctccggag ggtgctggtc ggacaccgag ctgctgtcaa tgttgtagac    1260
tttgatgaca gtacattgt ttctgcatct ggggatagaa ctataaaggt atggaacaca   1320
agtacttgtg aatttgtaag gaccttaaat ggacacaaac gaggcattgc ctgtttgcag   1380
tacagggaca ggctggtagt gagtggctca tctgacaaca ctatcagatt atgggacata   1440
gaatgtggtg catgtttacg agtgttagaa ggccatgagg aattggtgcg ttgtattcga   1500
tttgataaca gaggatagt cagtggggcc tatgatggaa aaattaaagt gtgggatctt   1560
gtggctgctt tggaccccg tgctcctgca gggacactct gtctacggac ccttgtggag   1620
cattccggaa gagttttcg actacagtttt gatgaattcc agattgtcag tagttcacat   1680
gatgacacaa tcctcatctg ggacttccta aatgatccag ctgcccaagc tgaacccccc   1740 cgttccccctt ctcgaacata cacctacatc tccagataaa taaccataca ctgacctcat   1800
```

```
acttgcccag gacccattaa agttgcggta tttaacgtat ctgccaatac caggatgagc   1860
aacaacagta acaatcaaac tactgcccag tttccctgga ctagccgagg agcagggctt   1920
tgagactcct gttgggacac agttggtctg cagtcggccc aggacggtct actcagcaca   1980
actgactgct tcagtgctgc tatcagaaga tgtcttctat caattgtgaa tgattggaac   2040
ttttaaacct cccctcctct cctcctttca cctctgcacc tagttttttc ccattggttc   2100
cagacaaagg tgacttataa atatatttag tgttttgcca gaaaaaaaaa a            2151
```

<210> SEQ ID NO 4
<211> LENGTH: 569
<212> TYPE: PRT
<213> ORGANISM: Homo sapiens

<400> SEQUENCE: 4

```
Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285

Ile Lys Ile Trp Asp Lys Asn Thr Leu Glu Cys Lys Arg Ile Leu Thr
    290                 295                 300

Gly His Thr Gly Ser Val Leu Cys Leu Gln Tyr Asp Glu Arg Val Ile
305                 310                 315                 320
```

```
Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
        355                 360                 365

Ile Ala Val Trp Asp Met Ala Ser Pro Thr Asp Ile Thr Leu Arg Arg
    370                 375                 380

Val Leu Val Gly His Arg Ala Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
            420                 425                 430

Ile Ala Cys Leu Gln Tyr Arg Asp Arg Leu Val Val Ser Gly Ser Ser
        435                 440                 445

Asp Asn Thr Ile Arg Leu Trp Asp Ile Glu Cys Gly Ala Cys Leu Arg
    450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
            500                 505                 510

Arg Thr Leu Val Glu His Ser Gly Arg Val Phe Arg Leu Gln Phe Asp
        515                 520                 525

Glu Phe Gln Ile Val Ser Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 5
<211> LENGTH: 6013
<212> TYPE: DNA
<213> ORGANISM: Homo sapiens

<400> SEQUENCE: 5
taagagaggg cgggggggaag gaagaggagg cgggatccgg gcgctgcgtt ggctgcggcc      60
tggcaccaaa gggcggcccc cggcggagag cggacccagt ggcctcggcg attatggacc     120
cggccgaggc ggtgctgcaa gagaaggcac tcaagtttat gaattcctca gagagagaag     180
actgtaataa tggcgaaccc cctaggaaga taataccaga gaagaattca cttagacaga     240
catacaacag ctgtgccaga ctctgcttaa accaagaaac agtatgttta gcaagcactg     300
ctatgaagac tgagaattgt gtggccaaaa caaaacttgc caatggcact tccagtatga     360
ttgtgcccaa gcaacggaaa ctctcagcaa gctatgaaaa ggaaaaggaa ctgtgtgtca     420
aatactttga gcagtggtca gagtcagatc aagtggaatt tgtggaacat cttatatccc     480
aaatgtgtca ttaccaacat gggcacataa actcgtatct aaacctatg ttgcagagag      540 atttcataac tgctctgcca gctcggggat tggatcatat tgctgagaac attctgtcat     600
acctggatgc caaatcacta tgtgctgctg aacttgtgtg caaggaatgg taccgagtga     660
cctctgatgg catgctgtgg aagaagctta tcgagagaat ggtcaggaca gattctctgt     720
```

| | |
|---|---|
| ggagaggcct ggcagaacga agaggatggg gacagtattt attcaaaaac aaacctcctg | 780 |
| acgggaatgc tcctcccaac tcttttata gagcacttta tcctaaaatt atacaagaca | 840 |
| ttgagacaat agaatctaat tggagatgtg aagacatag tttacagaga attcactgcc | 900 |
| gaagtgaaac aagcaaagga gtttactgtt tacagtatga tgatcagaaa atagtaagcg | 960 |
| gccttcgaga caacacaatc aagatctggg ataaaacac attggaatgc aagcgaattc | 1020 |
| tcacaggcca tacaggttca gtcctctgtc tccagtatga tgagagagtg atcataacag | 1080 |
| gatcatcgga ttccacggtc agagtgtggg atgtaaatac aggtgaaatg ctaaacacgt | 1140 |
| tgattcacca ttgtgaagca gttctgcact tgcgtttcaa taatggcatg atggtgacct | 1200 |
| gctccaaaga tcgttccatt gctgtatggg atatggcctc cccaactgac attaccctcc | 1260 |
| ggagggtgct ggtcggacac cgagctgctg tcaatgttgt agactttgat gacaagtaca | 1320 |
| ttgtttctgc atctggggat agaactataa aggtatggaa cacaagtact tgtgaatttg | 1380 |
| taaggacctt aaatggacac aaacgaggca ttgcctgttt gcagtacagg gacaggctgg | 1440 |
| tagtgagtgg ctcatctgac aacactatca gattatggga catagaatgt ggtgcatgtt | 1500 |
| tacgagtgtt agaaggccat gaggaattgg tgcgttgtat tcgatttgat aacaagagga | 1560 |
| tagtcagtgg ggcctatgat ggaaaaatta agtgtgggga tcttgtggct gctttggacc | 1620 |
| cccgtgctcc tgcagggaca ctctgtctac ggacccttgt ggagcattcc ggaagagttt | 1680 |
| ttcgactaca gtttgatgaa ttccagattg tcagtagttc acatgatgac acaatcctca | 1740 |
| tctgggactt cctaaatgat ccagctgccc aagctgaacc ccccgttcc ccttctcgaa | 1800 |
| cataccccta catctccaga taaataacca tacactgacc tcatacttgc ccaggaccca | 1860 |
| ttaaagttgc ggtatttaac gtatctgcca ataccaggat gagcaacaac agtaacaatc | 1920 |
| aaactactgc ccagtttccc tggactagcc gaggagcagg gctttgagac tcctgttggg | 1980 |
| acacagttgg tctgcagtcg gcccaggacg gtctactcag cacaactgac tgcttcagtg | 2040 |
| ctgctatcag aagatgtctt ctatcttttg tgaatgattg gaacttttaa acctcccctc | 2100 |
| ctctcctcct ttcacctctg cacctagttt tttcccattg gttccagaca aaggtgactt | 2160 |
| ataaatatat ttagtgtttt gccagaatct ctcttgcttt gccattaagc agaagaacta | 2220 |
| gtttccctgt atagcctgct gggagagacc cacttctagg gtatggggga tgcagcttca | 2280 |
| agcccagtgc ccagtgtctc cctgttaact gcaggaatgc caagcacctg gccagagcag | 2340 |
| cccagcccca atatgcttag gaggagacag agttccctct gtatagcctc tgggacaaga | 2400 |
| aaaagaaaac acaagaatgt atacactgga agatttgggc ctcctgcctg ccttctcttt | 2460 |
| gtttctgttc ctcttcccat ctactcccct acgccccttc aacctttttt ctctgtctgc | 2520 |
| ttcacctgag aagaaagtgt acgaagagag tgtcctcctc tcacatgagc cagatcagcc | 2580 |
| agaaaatgca acacttggaa gagttaaatg ctgttcagtg aagatttcag ccccaggcct | 2640 |
| ttgctgcaag tgaccctgtg gcaacagtgg attctcagac atgatactct catcatattt | 2700 |
| gcaactcttc tctctcttc ttccccacac ccaagaggag gattggtggt aggggcagg | 2760 |
| cagaggggt ggggagaagt ttcctgggct ccatcaatgg ctgcatcttt tctggactca | 2820 |
| gcagtctcct tgattccatg tagagtgtgg aaggagttg ctgattgcat ttcctctcat | 2880 |
| taacaattgg gtgtgtaata aaaagcattg tacttcatct taaatcactg gtaaggctca | 2940 |
| gcctacagaa agatttgaaa tggccagagc caatcgcttg gtgcattctg cgtaatggtt | 3000 |
| tccatctccg atttcctcat cagggcctgt gaatacccag gtgcctgtat cttgccaag | 3060 |
| accgtgatca aggtagctta agagagatgg tcaggagaaa acactgtttt tgtttttttt | 3120 |

```
gttgttttgt tttgttttgg ccagttaaat atcatctctc aaatattgat ctcaccgtgt    3180
caaccttgca ctgcacaacc ttccttctgc ttctcccaca cccagtattt gcagaagggc    3240
aaagctgctt aagagagagg atcagggtga agtttggcac acagggttta ttaatggggc    3300
aaaaactgcc ttttcttcct cctcctgacc ttatttttgct cttcactctc cccagccaat    3360
aaagcgtctg tggcgattgg tgaacagcat aaacagctgg acctcagcaa gggtcaggca    3420
aacccagtca ctcggaaggc agctgtgtga gctgccaagc tagtgggctt caggtgcaag    3480
ggtacctgtg ccacaccaac ctgggagcac acagaatact attaatgtgc acccagctgg    3540
tctccccagg caagaaggta tcctcttccc aaggtgtacc cactgaatgt tgttactaca    3600
tattgagagt cattttatgc atatgcattc tacctttcct gctttatgag tattttttaag    3660 cttttagttc aaggttatat tcagaaaata tttcccagta taatgataca tcgtagccta    3720
agaaatattt tctcaatgta attcccttcc cagctaccca aatgctacag agaaatgttt    3780
tctacttggc cactatcagg gttcgtcatc tattgtgttg actattaatg cttttttgat    3840
tgggtaagga ttttgctata gatgaaggta gagggctgtc agccctgaaa aacacacagg    3900
tcagacattt aaaaggcatg ggtttcgagc tgtctcaaaa tattgcccaa tagccataat    3960
tttaccagcc tttctgtcat atgctgctat tacaaagtgg aagctgttga atgtttattg    4020
gtgcccaggg ttttgctctc caatctaggt tcagttgaag gaatattgtt tctaagactg    4080
ttttgagaca tgtccagtac atcacaaagg agatcggggc gacccctgca gatgtggagc    4140
cattagccca gttgaggata ttctccaagt tgtcctctct cctgctgatg gaaatgggaa    4200
tgaagttaag tggtctgaaa aacttgaatc gttcacattt ctcagctctg ggggtcattt    4260
accagtttgt tgtagaagaa ataatcaggt aagttaaaag ttcatttcca gagaaggtaa    4320
accccactta ccatctctgc atgatttcag tgggaattga ttatcactaa tccccaactg    4380
ggctagaata aatgtaaagt ttgacctttt taaaacgaaa agagagacaa agtctcagca    4440
cattccaagg agtggtagaa acagagctga aggtgtcccc attgtagatt agtctcttct    4500
cactaaaatt tactttccaa cgtagggcct aaaggaaacc tttcttaaag acaggctgaa    4560 acccccttcaa aggcagatga ggaggtacag acacgtgacc ttttggtgca cactggagct    4620
acttggacaa gaccagcatg ccttgctgca cgtgtgtgta tttcactgct gagaacatcc    4680
tttaacttgg tgtgcaattt gaaaggatgt gaatcatgga tggaaggcca tttgtacatg    4740
tcccttggca aaattctttc tggtgtctcc taacttcaga gacagggact ctttttggat    4800
ctctattgac aagtaataaa agtctggccc tcataacttg tttccgaact agaaaagtct    4860
gtgagacccc tacatcattc tggttttttt gcttgagtaa gaacaatcct ttttattttt    4920
tcttctgtac agtctaaagc tacagagaaa aaaaaatgca ctcttccctt gccggctcct    4980
ggtaccattg gtctgaacag ctgtagttgg tctactcctt acttagcact tgattgtgtg    5040
gggaaacaaa ggtgggaggg gtggggaata ctggaaataa tcaggcaat ttttttcttt    5100 cccataattg gactagatac cttggtactg ttgaccttct cagcatctcc cttttgcctt    5160
agatggcaac accctccagt ctgtagcaga gcagtccaac ccagattagt gcagcccgga    5220
ggcttagggt gcagcctccc tggtcttcct ccacacagtt gttcaccaac agaccagacc    5280
tcctttaacc acagtgtcaa catagtatcg gaaagagagc catttcttag gggaataaaa    5340
cagtttcgct tctttagctc atctgtggtg tcagaatcct tggagctgaa gagagaaatc    5400
aaaagagcat gatgatggct gcctggtttc aggtggaact taatgcattg atctttagaa    5460
gctccttctg ttggaagttg agtacctgtg atctaaaatg tcctggaggc agatgacatc    5520
```

```
taaaatatgt gctttccaac cagcacagct ggcgctctta gctcctgatt ggttgtgtgt    5580
tttattaagg atcagtgcag ttaagtcgta ttttaaagtg ttacctcccc tcctaaccct    5640
tccccttctt ggacactgaa ggaaaaggcc aactagggtg ttagccctct gggcaccaag    5700
gaaactaaca gctttctcaa agcggtgacc actcaggcca gcccagacaa atctgaggga    5760
tggccagtgc actccaatga tgggacaggc ctaacaacac atgtaagctt ccccgagagc    5820
tttcagctgg ttcacctctt tgttctctag actcttaagt actgactgct ttgacttttg    5880
tgattatgtt atggtgatgt gtagtcagtg taccaatatg ttcacaacct aggatcatga    5940
taatggagtg tgtttgggt tttttttaac tgttcagaaa aaagtaaat tacaaatata     6000 agattaaagt gaa                                                       6013

<210> SEQ ID NO 6
<211> LENGTH: 198
<212> TYPE: PRT
<213> ORGANISM: Homo sapiens

<400> SEQUENCE: 6

Met Ala Lys Gln Pro Ser Asp Val Ser Ser Glu Cys Asp Arg Glu Gly
 1               5                  10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
        195

<210> SEQ ID NO 7
<211> LENGTH: 597
<212> TYPE: DNA
<213> ORGANISM: Homo sapiens

<400> SEQUENCE: 7
atggcaaagc aaccttctga tgtaagttct gagtgtgacc gagaaggtag acaattgcag    60
cctgcggaga ggcctcccca gctcagacct ggggccccta cctccctaca gacagagcca    120
caaggtaatc ctgaaggcaa tcacggaggt gaagggggaca gctgccccca cggcagccct    180
cagggcccgc tggccccacc tgccagccct ggccttttg ctaccagatc cccgcttttc    240
```

```
atctttatga gaagatcctc cctgctgtct cgatcctcca gtgggtattt ctcttttgac      300
acagacagga gcccagcacc catgagttgt gacaaatcaa cacaaacccc aagtcctcct      360
tgccaggcct tcaaccacta tctcagtgca atggcttcca tgaggcaggc tgaacctgca      420
gatatgcgcc agagatatg gatcgcccaa gagttgcggc gtatcggaga cgagtttaac      480
gcttactatg caaggagggt attttttgaat aattaccaag cagccgaaga ccacccacga    540
atggttatct tacgactgtt acgttacatt gtccgcctgg tgtggagaat gcattga        597
```

<210> SEQ ID NO 8
<211> LENGTH: 744
<212> TYPE: PRT
<213> ORGANISM: Homo sapiens

<400> SEQUENCE: 8

```
Met Glu Gln Asp Pro Lys Pro Pro Arg Leu Arg Leu Trp Ala Leu Ile
1               5                   10                  15

Pro Trp Leu Pro Arg Lys Gln Arg Pro Arg Ile Ser Gln Thr Ser Leu
                20                  25                  30

Pro Val Pro Gly Pro Gly Ser Gly Pro Gln Arg Asp Ser Asp Glu Gly
            35                  40                  45

Val Leu Lys Glu Ile Ser Ile Thr His His Val Lys Ala Gly Ser Glu
        50                  55                  60

Lys Ala Asp Pro Ser His Phe Glu Leu Leu Lys Val Leu Gly Gln Gly
65                  70                  75                  80

Ser Phe Gly Lys Val Phe Leu Val Arg Lys Val Thr Arg Pro Asp Ser
                85                  90                  95

Gly His Leu Tyr Ala Met Lys Val Leu Lys Lys Ala Thr Leu Lys Val
            100                 105                 110

Arg Asp Arg Val Arg Thr Lys Met Glu Arg Asp Ile Leu Ala Asp Val
        115                 120                 125

Asn His Pro Phe Val Val Lys Leu His Tyr Ala Phe Gln Thr Glu Gly
    130                 135                 140

Lys Leu Tyr Leu Ile Leu Asp Phe Leu Arg Gly Gly Asp Leu Phe Thr
145                 150                 155                 160

Arg Leu Ser Lys Glu Val Met Phe Thr Glu Glu Asp Val Lys Phe Tyr
                165                 170                 175

Leu Ala Glu Leu Ala Leu Gly Leu Asp His Leu His Ser Leu Gly Ile
            180                 185                 190

Ile Tyr Arg Asp Leu Lys Pro Glu Asn Ile Leu Leu Asp Glu Glu Gly
        195                 200                 205

His Ile Lys Leu Thr Asp Phe Gly Leu Ser Lys Glu Ala Ile Asp His
    210                 215                 220

Glu Lys Lys Ala Tyr Ser Phe Cys Gly Thr Val Glu Tyr Met Ala Pro
225                 230                 235                 240

Glu Val Val Asn Arg Gln Gly His Ser His Ser Ala Asp Trp Trp Ser
                245                 250                 255

Tyr Gly Val Leu Met Phe Glu Met Leu Thr Gly Ser Leu Pro Phe Gln
            260                 265                 270

Gly Lys Asp Arg Lys Glu Thr Met Thr Leu Ile Leu Lys Ala Lys Leu
        275                 280                 285

Gly Met Pro Gln Phe Leu Ser Thr Glu Ala Gln Ser Leu Leu Arg Ala
    290                 295                 300

Leu Phe Lys Arg Asn Pro Ala Asn Arg Leu Gly Ser Gly Pro Asp Gly
305                 310                 315                 320
```

```
Ala Glu Glu Ile Lys Arg His Val Phe Tyr Ser Thr Ile Asp Trp Asn
            325                 330                 335

Lys Leu Tyr Arg Arg Glu Ile Lys Pro Pro Phe Lys Pro Ala Val Ala
        340                 345                 350

Gln Pro Asp Asp Thr Phe Tyr Phe Asp Thr Glu Phe Thr Ser Arg Thr
            355                 360                 365

Pro Lys Asp Ser Pro Gly Ile Pro Pro Ser Ala Gly Ala His Gln Leu
    370                 375                 380

Phe Arg Gly Phe Ser Phe Val Ala Thr Gly Leu Met Glu Asp Asp Gly
385                 390                 395                 400

Lys Pro Arg Ala Pro Gln Ala Pro Leu His Ser Val Val Gln Gln Leu
                405                 410                 415

His Gly Lys Asn Leu Val Phe Ser Asp Gly Tyr Val Val Lys Glu Thr
            420                 425                 430

Ile Gly Val Gly Ser Tyr Ser Glu Cys Lys Arg Cys Val His Lys Ala
            435                 440                 445

Thr Asn Met Glu Tyr Ala Val Lys Val Ile Asp Lys Ser Lys Arg Asp
    450                 455                 460

Pro Ser Glu Glu Ile Glu Ile Leu Leu Arg Tyr Gly Gln His Pro Asn
465                 470                 475                 480

Ile Ile Thr Leu Lys Asp Val Tyr Asp Asp Gly Lys His Val Tyr Leu
                485                 490                 495

Val Thr Glu Leu Met Arg Gly Gly Glu Leu Leu Asp Lys Ile Leu Arg
            500                 505                 510

Gln Lys Phe Phe Ser Glu Arg Glu Ala Ser Phe Val Leu His Thr Ile
        515                 520                 525

Gly Lys Thr Val Glu Tyr Leu His Ser Gln Gly Val Val His Arg Asp
    530                 535                 540

Leu Lys Pro Ser Asn Ile Leu Tyr Val Asp Glu Ser Gly Asn Pro Glu
545                 550                 555                 560

Cys Leu Arg Ile Cys Asp Phe Gly Phe Ala Lys Gln Leu Arg Ala Glu
                565                 570                 575

Asn Gly Leu Leu Met Thr Pro Cys Tyr Thr Ala Asn Phe Val Ala Pro
            580                 585                 590

Glu Val Leu Lys Arg Gln Gly Tyr Asp Glu Gly Cys Asp Ile Trp Ser
        595                 600                 605

Leu Gly Ile Leu Leu Tyr Thr Met Leu Ala Gly Tyr Thr Pro Phe Ala
    610                 615                 620

Asn Gly Pro Ser Asp Thr Pro Glu Glu Ile Leu Thr Arg Ile Gly Ser
625                 630                 635                 640

Gly Lys Phe Thr Leu Ser Gly Gly Asn Trp Asn Thr Val Ser Glu Thr
                645                 650                 655

Ala Lys Asp Leu Val Ser Lys Met Leu His Val Asp Pro His Gln Arg
            660                 665                 670

Leu Thr Ala Lys Gln Val Leu Gln His Pro Trp Val Thr Gln Lys Asp
        675                 680                 685

Lys Leu Pro Gln Ser Gln Leu Ser His Gln Asp Leu Gln Leu Val Lys
    690                 695                 700

Gly Ala Met Ala Ala Thr Tyr Ser Ala Leu Asn Ser Ser Lys Pro Thr
705                 710                 715                 720

Pro Gln Leu Lys Pro Ile Glu Ser Ser Ile Leu Ala Gln Arg Arg Val
                725                 730                 735

Arg Lys Leu Pro Ser Thr Thr Leu
```

<210> SEQ ID NO 9
<211> LENGTH: 2235
<212> TYPE: DNA
<213> ORGANISM: Homo sapiens

<400> SEQUENCE: 9

| | | | | | |
|---|---|---|---|---|---|
| atggagcagg | atcccaagcc | gccccgtctg | cggctctggg | ccctgatccc | ctggcttccc | 60 |
| aggaagcagc | ggcccaggat | cagccagacc | tctctgcctg | tccctggccc | tggctctggc | 120 |
| ccccagcggg | actcggatga | gggcgtcctc | aaggagatct | ccatcacgca | ccacgtcaag | 180 |
| gctggctctg | agaaggctga | tccatcccat | ttcgagctcc | tcaaggttct | gggccaggga | 240 |
| tcctttggca | aagtcttcct | ggtgcggaaa | gtcacccggc | ctgacagtgg | gcacctgtat | 300 |
| gctatgaagg | tgctgaagaa | ggcaacgctg | aaagtacgtg | accgcgtccg | gaccaagatg | 360 |
| gagagagaca | tcctggctga | tgtaaatcac | ccattcgtgg | tgaagctgca | ctatgccttc | 420 |
| cagaccgagg | gcaagctcta | tctcattctg | gacttcctgc | gtggtgggga | cctcttcacc | 480 |
| cggctctcaa | agaggtgat | gttcacggag | gaggatgtga | gtttttacct | ggccgagctg | 540 |
| gctctgggcc | tggatcacct | gcacagcctg | ggtatcattt | acagagacct | caagcctgag | 600 |
| aacatccttc | tggatgagga | gggccacatc | aaactcactg | actttggcct | gagcaaagag | 660 |
| gccattgacc | acgagaagaa | ggcctattct | ttctgcggga | cagtggagta | catggcccct | 720 |
| gaggtcgtca | accgccaggg | ccactcccat | agtgcggact | ggtggtccta | tggggtgttg | 780 |
| atgtttgaga | tgctgacggg | ctccctgccc | ttccagggga | aggaccggaa | ggagaccatg | 840 |
| acactgattc | tgaaggcgaa | gctaggcatg | ccccagtttc | tgagcactga | agcccagagc | 900 |
| ctcttgcggg | ccctgttcaa | gcggaatcct | gccaaccggc | tcggctccgg | ccctgatggg | 960 |
| gcagaggaaa | tcaagcggca | tgtcttctac | tccaccattg | actggaataa | gctataccgt | 1020 |
| cgtgagatca | agccaccctt | caagccagca | gtggctcagc | tgatgacac | cttctacttt | 1080 |
| gacaccgagt | tcacgtcccg | cacacccaag | gattccccag | gcatcccccc | cagcgctggg | 1140 |
| gcccatcagc | tgttccgggg | cttcagcttc | gtggccaccg | gcctgatgga | agacgacggc | 1200 |
| aagcctcgtg | ccccgcaggc | accoctgcac | tcggtggtac | agcaactcca | tgggaagaac | 1260 |
| ctggttttta | gtgacggcta | cgtggtaaag | agacaattg | tgtgggctc | ctactctgag | 1320 |
| tgcaagcgct | gtgtccacaa | ggccaccaac | atggagtatg | ctgtcaaggt | cattgataag | 1380 |
| agcaagcggg | atccttcaga | agagattgag | attcttctgc | ggtatggcca | gcaccccaac | 1440 |
| atcatcactc | tgaaagatgt | gtatgatgat | ggcaaacacg | tgtacctggt | gacagagctg | 1500 |
| atgcggggtg | gggagctgct | ggacaagatc | ctgcggcaga | gttcttctc | agagcggag | 1560 |
| gccagctttg | tcctgcacac | cattggcaaa | actgtggagt | atctgcactc | acagggggtt | 1620 |
| gtgcacaggg | acctgaagcc | cagcaacatc | ctgtatgtgg | acgagtccgg | gaatcccgag | 1680 |
| tgcctgcgca | tctgtgactt | tggttttgcc | aaacagctgc | gggctgagaa | tgggctcctc | 1740 |
| atgacacctt | gctacacagc | caactttgtg | gcgcctgagg | tgctgaagcg | ccagggctac | 1800 |
| gatgaaggct | gcgacatctg | gagcctgggc | attctgctgt | acaccatgct | ggcaggatat | 1860 |
| actccatttg | ccaacggtcc | cagtgacaca | ccagaggaaa | tcctaaccg | gatcggcagt | 1920 |
| gggaagttta | ccctcagtgg | gggaaattgg | aacacagttt | cagagacagc | caaggacctg | 1980 |
| gtgtccaaga | tgctacacgt | ggatcccac | cagcgcctca | cagctaagca | ggttctgcag | 2040 |
| catccatggg | tcacccagaa | agacaagctt | ccccaaagcc | agctgtccca | ccaggaccta | 2100 |

```
cagcttgtga agggagccat ggctgccacg tactccgcac tcaacagctc caagcccacc   2160 cccagctga agcccatcga gtcatccatc ctggcccagc ggcgagtgag gaagttgcca    2220
tccaccaccc tgtga                                                    2235
```

<210> SEQ ID NO 10
<211> LENGTH: 740
<212> TYPE: PRT
<213> ORGANISM: Homo sapiens

<400> SEQUENCE: 10

```
Met Pro Leu Ala Gln Leu Ala Asp Pro Trp Gln Lys Met Ala Val Glu
1               5                   10                  15

Ser Pro Ser Asp Ser Ala Glu Asn Gly Gln Gln Ile Met Asp Glu Pro
            20                  25                  30

Met Gly Glu Glu Glu Ile Asn Pro Gln Thr Glu Val Ser Ile Lys
        35                  40                  45

Glu Ile Ala Ile Thr His His Val Lys Glu Gly His Glu Lys Ala Asp
50                  55                  60

Pro Ser Gln Phe Glu Leu Leu Lys Val Leu Gly Gln Gly Ser Phe Gly
65                  70                  75                  80

Lys Val Phe Leu Val Lys Lys Ile Ser Gly Ser Asp Ala Arg Gln Leu
                85                  90                  95

Tyr Ala Met Lys Val Leu Lys Lys Ala Thr Leu Lys Val Arg Asp Arg
            100                 105                 110

Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
130                 135                 140

Leu Ile Leu Asp Phe Leu Arg Gly Gly Asp Leu Phe Thr Arg Leu Ser
145                 150                 155                 160

Lys Glu Val Met Phe Thr Glu Glu Asp Val Lys Phe Tyr Leu Ala Glu
                165                 170                 175

Leu Ala Leu Ala Leu Asp His Leu His Ser Leu Gly Ile Ile Tyr Arg
            180                 185                 190

Asp Leu Lys Pro Glu Asn Ile Leu Leu Asp Glu Glu Gly His Ile Lys
        195                 200                 205

Leu Thr Asp Phe Gly Leu Ser Lys Glu Ser Ile Asp His Glu Lys Lys
210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
            260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
290                 295                 300

Arg Asn Pro Ala Asn Arg Leu Gly Ala Gly Pro Asp Gly Val Glu Glu
305                 310                 315                 320

Ile Lys Arg His Ser Phe Phe Ser Thr Ile Asp Trp Asn Lys Leu Tyr
                325                 330                 335

Arg Arg Glu Ile His Pro Pro Phe Lys Pro Ala Thr Gly Arg Pro Glu
            340                 345                 350
```

Asp Thr Phe Tyr Phe Asp Pro Glu Phe Thr Ala Lys Thr Pro Lys Asp
            355                 360                 365

Ser Pro Gly Ile Pro Pro Ser Ala Asn Ala His Gln Leu Phe Arg Gly
370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
                405                 410                 415

Gln Phe Thr Asp Gly Tyr Glu Val Lys Glu Asp Ile Gly Val Gly Ser
            420                 425                 430

Tyr Ser Val Cys Lys Arg Cys Ile His Lys Ala Thr Asn Met Glu Phe
        435                 440                 445

Ala Val Lys Ile Ile Asp Lys Ser Lys Arg Asp Pro Thr Glu Glu Ile
450                 455                 460

Glu Ile Leu Leu Arg Tyr Gly Gln His Pro Asn Ile Ile Thr Leu Lys
465                 470                 475                 480

Asp Val Tyr Asp Asp Gly Lys Tyr Val Tyr Val Val Thr Glu Leu Met
                485                 490                 495

Lys Gly Gly Glu Leu Leu Asp Lys Ile Leu Arg Gln Lys Phe Phe Ser
            500                 505                 510

Glu Arg Glu Ala Ser Ala Val Leu Phe Thr Ile Thr Lys Thr Val Glu
        515                 520                 525

Tyr Leu His Ala Gln Gly Val Val His Arg Asp Leu Lys Pro Ser Asn
530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
                565                 570                 575

Thr Pro Cys Tyr Thr Ala Asn Phe Val Ala Pro Glu Val Leu Lys Arg
            580                 585                 590

Gln Gly Tyr Asp Ala Ala Cys Asp Ile Trp Ser Leu Gly Val Leu Leu
        595                 600                 605

Tyr Thr Met Leu Thr Gly Tyr Thr Pro Phe Ala Asn Gly Pro Asp Asp
610                 615                 620

Thr Pro Glu Glu Ile Leu Ala Arg Ile Gly Ser Gly Lys Phe Ser Leu
625                 630                 635                 640

Ser Gly Gly Tyr Trp Asn Ser Val Ser Asp Thr Ala Lys Asp Leu Val
                645                 650                 655

Ser Lys Met Leu His Val Asp Pro His Gln Arg Leu Thr Ala Ala Leu
            660                 665                 670

Val Leu Arg His Pro Trp Ile Val His Trp Asp Gln Leu Pro Gln Tyr
        675                 680                 685

Gln Leu Asn Arg Gln Asp Ala Pro His Leu Val Lys Gly Ala Met Ala
690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Arg Gly Ile Lys Lys Ile Thr
                725                 730                 735

Ser Thr Ala Leu
            740

<210> SEQ ID NO 11
<211> LENGTH: 2223
<212> TYPE: DNA
<213> ORGANISM: Homo sapiens

<400> SEQUENCE: 11

```
atgccgctgg cgcagctggc ggacccgtgg cagaagatgg ctgtggagag cccgtccgac      60
agcgctgaga atggacagca aattatggat gaacctatgg gagaggagga gattaaccca     120
caaactgaag aagtcagtat caaagaaatt gcaatcacac atcatgtaaa ggaaggacat     180
gaaaaggcag atccttccca gtttgaactt ttaaaagtat tagggcaggg atcatttgga     240
aaggttttct tagttaaaaa aatctcaggc tctgatgcta ggcagcttta tgccatgaag     300
gtattgaaga aggccacact gaaagttcga gaccgagttc ggacaaaaat ggaacgtgat     360
atcttggtag aggttaatca tccttttatt gtcaagttgc attatgcttt tcaaactgaa     420
gggaagttgt atcttatttt ggattttctc aggggaggag atttgtttac acgcttatcc     480
aaagaggtga tgttcacaga agaagatgtc aaattctact ggctgaact tgcacttgct      540
ttagaccatc tacatagcct gggaataatt tatagagact taaaaccaga aaatatactt     600
cttgatgaag aaggtcacat caagttaaca gatttcggcc taagtaaaga gtctattgac     660
catgaaaaga aggcatattc ttttttgtgga actgtggagt atatggctcc agaagtagtt    720
aatcgtcgag gtcatactca gagtgctgac tggtggtctt ttggtgtgtt aatgtttgaa     780
atgcttactg gtacactccc tttccaagga aaagatcgaa agaaacaat gactatgatt      840
cttaaagcca aacttggaat gccacagttt ttgagtcctg aagcgcagag tcttttacga     900
atgcttttca gcgaaatcc tgcaaacaga ttaggtgcag gaccagatgg agttgaagaa      960
attaaaagac attcatttt ctcaacgata gactggaata aactgtatag aagagaaatt     1020
catccgccat ttaaacctgc aacgggcagg cctgaagata cattctattt tgatcctgag   1080
tttactgcaa aaactcccaa agattcacct ggcattccac ctagtgctaa tgcacatcag   1140
cttttttcggg ggtttagttt tgttgctatt acctcagatg atgaaagcca agctatgcag 1200
acagttggtg tacattcaat tgttcagcag ttacacagga acagtattca gtttactgat  1260
ggatatgaag taaagaaga tattggagtt ggctcctact ctgtttgcaa agagatgtata 1320
cataaagcta caacatgga gtttcagtg aagattattg ataaaagcaa gagagaccca   1380
acagaagaaa ttgaaattct tcttcgttat ggacagcatc caaacattat cactctaaag 1440
gatgtatatg atgatggaaa gtatgtgtat gtagtaacag aacttatgaa aggaggtgaa 1500
ttgctggata aaattcttag acaaaaattt ttctctgaac gagaggccag tgctgtcctg 1560
ttcactataa ctaaaaccgt tgaatatctt cacgcacaag gggtggttca tagagacttg 1620
aaacctagca acattcttta tgtggatgaa tctggtaatc cggaatctat tcgaatttgt 1680
gattttggct ttgcaaaaca gctgagagcg gaaaatggtc ttctcatgac tccttgttac 1740
actgcaaatt ttgttgcacc agaggtttta aaaagacaag gctatgatgc tgcttgtgat 1800
atatggagtc ttggtgtcct actctataca atgcttaccg gttacactcc atttgcaaat 1860
ggtcctgatg atacaccaga ggaaatattg gcacgaatag gtagcggaaa attctcactc 1920
agtggtggtt actggaattc tgtttcagac acagcaaagg acctggtgtc aaagatgctt 1980
catgtagacc ctcatcagag actgactgct gctcttgtgc tcagacatcc ttggatcgtc 2040
cactgggacc aactgccaca ataccaacta acagacagg atgcaccaca tctagtaaag 2100
ggtgccatgg cagctacata ttctgctttg aaccgtaatc agtcaccagt tttggaacca 2160
gtaggccgct ctactcttgc tcagcggaga ggtattaaaa aaatcacctc aacagccctg 2220
tga                                                                 2223
```

<210> SEQ ID NO 12
<211> LENGTH: 524
<212> TYPE: PRT
<213> ORGANISM: Homo sapiens

<400> SEQUENCE: 12

```
Met Glu Leu Gly Pro Glu Pro Pro His Arg Arg Leu Leu Phe Ala
1               5                   10                  15

Cys Ser Pro Pro Ala Ser Gln Pro Val Val Lys Ala Leu Phe Gly
                20                  25                  30

Ala Ser Ala Ala Gly Gly Leu Ser Pro Val Thr Asn Leu Thr Val Thr
            35                  40                  45

Met Asp Gln Leu Gln Gly Leu Gly Ser Asp Tyr Glu Gln Pro Leu Glu
50                  55                  60

Val Lys Asn Asn Ser Asn Leu Gln Arg Met Gly Ser Ser Glu Ser Thr
65                  70                  75                  80

Asp Ser Gly Phe Cys Leu Asp Ser Pro Gly Pro Leu Asp Ser Lys Glu
                85                  90                  95

Asn Leu Glu Asn Pro Met Arg Arg Ile His Ser Leu Pro Gln Lys Leu
                100                 105                 110

Leu Gly Cys Ser Pro Ala Leu Lys Arg Ser His Ser Asp Ser Leu Asp
            115                 120                 125

His Asp Ile Phe Gln Leu Ile Asp Pro Asp Glu Asn Lys Glu Asn Glu
130                 135                 140

Ala Phe Glu Phe Lys Lys Pro Val Arg Pro Val Ser Arg Gly Cys Leu
145                 150                 155                 160

His Ser His Gly Leu Gln Gly Gly Lys Asp Leu Phe Thr Gln Arg Gln
                165                 170                 175

Asn Ser Ala Pro Ala Arg Met Leu Ser Ser Asn Glu Arg Asp Ser Ser
                180                 185                 190

Glu Pro Gly Asn Phe Ile Pro Leu Phe Thr Pro Gln Ser Pro Val Thr
            195                 200                 205

Ala Thr Leu Ser Asp Glu Asp Gly Phe Val Asp Leu Leu Asp Gly
210                 215                 220

Glu Asn Leu Lys Asn Glu Glu Glu Thr Pro Ser Cys Met Ala Ser Leu
225                 230                 235                 240

Trp Thr Ala Pro Leu Val Met Arg Thr Thr Asn Leu Asp Asn Arg Cys
                245                 250                 255

Lys Leu Phe Asp Ser Pro Ser Leu Cys Ser Ser Ser Thr Arg Ser Val
                260                 265                 270

Leu Lys Arg Pro Glu Arg Ser Gln Glu Glu Ser Pro Pro Gly Ser Thr
            275                 280                 285

Lys Arg Arg Lys Ser Met Ser Gly Ala Ser Pro Lys Glu Ser Thr Asn
290                 295                 300

Pro Glu Lys Ala His Glu Thr Leu His Gln Ser Leu Ser Leu Ala Ser
305                 310                 315                 320

Ser Pro Lys Gly Thr Ile Glu Asn Ile Leu Asp Asn Asp Pro Arg Asp
                325                 330                 335

Leu Ile Gly Asp Phe Ser Lys Gly Tyr Leu Phe His Thr Val Ala Gly
                340                 345                 350

Lys His Gln Asp Leu Lys Tyr Ile Ser Pro Glu Ile Met Ala Ser Val
            355                 360                 365

Leu Asn Gly Lys Phe Ala Asn Leu Ile Lys Glu Phe Val Ile Ile Asp
370                 375                 380

Cys Arg Tyr Pro Tyr Glu Tyr Glu Gly Gly His Ile Lys Gly Ala Val
```

```
                385                 390                 395                 400
Asn Leu His Met Glu Glu Val Glu Asp Phe Leu Leu Lys Lys Pro
                    405                 410                 415
Ile Val Pro Thr Asp Gly Lys Arg Val Ile Val Val Phe His Cys Glu
                420                 425                 430
Phe Ser Ser Glu Arg Gly Pro Arg Met Cys Arg Tyr Val Arg Glu Arg
            435                 440                 445
Asp Arg Leu Gly Asn Glu Tyr Pro Lys Leu His Tyr Pro Glu Leu Tyr
        450                 455                 460
Val Leu Lys Gly Gly Tyr Lys Glu Phe Phe Met Lys Cys Gln Ser Tyr
465                 470                 475                 480
Cys Glu Pro Pro Ser Tyr Arg Pro Met His His Glu Asp Phe Lys Glu
                485                 490                 495
Asp Leu Lys Lys Phe Arg Thr Lys Ser Arg Thr Trp Ala Gly Glu Lys
            500                 505                 510
Ser Lys Arg Glu Met Tyr Ser Arg Leu Lys Lys Leu
        515                 520

<210> SEQ ID NO 13
<211> LENGTH: 3717
<212> TYPE: DNA
<213> ORGANISM: Homo sapiens

<400> SEQUENCE: 13
gaacagcgaa gacagcgtga gcctgggccg ttgcctcgag gctctcgccc ggcttctctt      60
gccgacccgc cacgtttgtt tggatttaat cttcaggttg ccggcgcccg cccgcccgct    120
ggcctcgcgg tgtgagaggg aagcaccggt gcctgtggct ggtggctggc gcctggaggg    180
tccgcacacc cgcccggccg cgccgcttgc ccgcggcagc cgcgtccctg aaccgcggag    240
tcgtgtttgt gtttgacccc cggggcgccg tggcgcgcgg ccgaggccgg tgtcggcggg    300
gcggggcggt cgcggcggag gcagaggaag agggagcggg agctctgcga ggccgggcgc    360
cgccatggaa ctgggcccgg agccccgca ccgccgccgc ctgctcttcg cctgcagccc    420
ccctcccgcg tcgcagcccg tcgtgaaggc gctatttggc gcttcagccg ccggggact    480
gtcgcctgtc accaacctga ccgtcactat ggaccagctg cagggtctgg gcagtgatta    540
tgagcaacca ctggaggtga agaacaacag taatctgcag agaatgggct cctccgagtc    600
aacagattca ggtttctgtc tagattctcc tgggccattg gacagtaaag aaaaccttga    660
aaatcctatg agaagaatac attccctacc tcagaagctg ttgggatgta gtccagctct    720
gaagaggagc cattctgatt ctcttgacca tgacatcttt cagctcatcg acccagatga    780
gaacaaggaa aatgaagcct tgagtttaa aagccagta agacctgtat ctcgtggctg    840
cctgcactct catggactcc aggagggtaa agatctcttc acacagaggc agaactctgc    900
cccagctcgg atgctttcct caaatgaaag agatagcagt gaaccaggga atttcattcc    960
tcttttaca ccccagtcac ctgtgacagc cactttgtct gatgaggatg atggcttcgt   1020
ggaccttctc gatggagaga atctgaagaa tgaggaggag acccctcgt gcatggcaag   1080
cctctggaca gctcctctcg tcatgagaac tacaaaccct gacaaccgat gcaagctgtt   1140
tgactcccct tccctgtgta gctccagcac tcggtcagtg ttgaagagac agaacgatc   1200
tcaagaggag tctccacctg gaagtacaaa gaggaggaag agcatgtctg gggccagccc   1260
caaagagtca actaatccag agaaggccca tgagactctt catcagtctt tatccctggc   1320
atcttccccc aaaggaacca ttgagaacat tttggacaat gacccaaggg accttatagg   1380
```

```
agacttctcc aagggttatc tctttcatac agttgctggg aaacatcagg atttaaaata      1440
catctctcca gaaattatgg catctgtttt gaatggcaag tttgccaacc tcattaaaga      1500
gtttgttatc atcgactgtc gatacccata tgaatacgag ggaggccaca tcaagggtgc      1560
agtgaacttg cacatggaag aagaggttga agacttctta ttgaagaagc ccattgtacc      1620
tactgatggc aagcgtgtca ttgttgtgtt tcactgcgag ttttcttctg agagaggtcc      1680
ccgcatgtgc cggtatgtga gagagagaga tcgcctgggt aatgaatacc ccaaactcca      1740
ctaccctgag ctgtatgtcc tgaaggggGG atacaaggag ttctttatga aatgccagtc      1800
ttactgtgag ccccctagct accggcccat gcaccacgag gactttaaag aagacctgaa      1860
gaagttccgc accaagagcc ggacctgggc aggggagaag agcaagaggg agatgtacag      1920
tcgtctgaag aagctctgag gcggcagga ccagccagca gcagcccaag cttccctcca      1980
tccccctttta ccctctttgc tgcagagaaa cttaagcaaa ggggacagct gtgtgacatt      2040
tggagagggg gcctgggact tccatgcctt aaacctacct cccacactcc caaggttgga      2100
gcccagggca tcttgctggc tacgcctctt ctgtccctgt tagacgtcct ccgtccatat      2160
cagaactgtg ccacaatgca gttctgagca ccgtgtcaag ctgctctgag ccacagtggg      2220
atgaaccagc cggggcctta tcgggctcca gccatctcat gaggggagag gagacggagg      2280
ggagtagaga agttacacag aaatgctgct ggccaaatag caaagacaac ctgggaagga      2340
aaggtctttg tgggataatc catatgttta atttattcaa cttcatcaat cactttattt      2400
tattttttt tctaactcct ggagacttat tttactgctt cattaggttg aaatactgcc      2460
attctaggta gggttttatt atcccaggga ctacctcggc ttttaattta aaaaaaaaaa      2520
agaagtgggt aagaaaatgc aaacctgtta taagttatcg gacagaaagc taggtgctct      2580
gtcaccccca ggaggcgctg tggtactggg gctgctgcta tttaagccaa gaactgaggt      2640
cctggtgaga gcgttggacc caggcttggc tgcctgacat aagctaaatc tcccagaccc      2700
accactggct accgatatct atttggtggg aggtgtggcc ctgttcttcc tcaccccagt      2760
tccatgacat tggctggtat aggagccaca gtcaggaaag cacttgaggc agcatctgtt      2820
gggccacccc cggctcagtg ctggaatgtt gcagtgtagg tttcccaggg aagggggggtg     2880
ggggtaggtg ggctccacag gatgggggag gagcatgtcc actgagtatc ttccttatgt      2940
tgctgtgata ttgatagctt ttattttcta attttttaaaa aatggtcata ttatgagtca      3000
aagagtatca aatcagtgtt ggatggacca cccaagggtg aggagagggg ctggaagccc      3060
tgggcattag gagaagggag tgggtgctgg catggacatg actggataga attttctcag      3120
gagggagctt ggtggatttt gaaggtaaaa cttttctgggt ttatcatgtt ttaattttag      3180
agacaggag tgatgaatca tcaccggttg tccccttatc taactccata aaagtgggaa      3240
tttcaaaaga acacctcatc caaggagctg gggcagactt cattgattct agagagacct      3300
gtttcagtgc ctactcatcc ctgccctctg gtgccagcct ccttaccatc acggcttcac      3360
tgaggtgtag gtgggttttt cttaaacagg agacagtctc tccctctta cctcaacttc       3420
ttggggtggg aatcagtgat actggagatg gctagttgct gtgttacggg tttgagttac      3480
atttggctat aaaacaatct tgttgggaaa aatgtggggg agaggacttc ttcctacacg      3540
cgcattgaga cagattccaa ctggttaatg atattgtttg taagaaagag attctgttgg      3600
ttgactgcct aaagagaaag gtgggatggc cttcagatta taccagctta gctagcatta      3660
ctaaccaact gttggaagct ctgaaaataa aagatcttga acccataaaa aaaaaaa       3717
```

<210> SEQ ID NO 14

```
<211> LENGTH: 38
<212> TYPE: PRT
<213> ORGANISM: Homo sapiens

<400> SEQUENCE: 14

Asp His Ile Ala Glu Asn Ile Leu Ser Tyr Leu Asp Ala Lys Ser Leu
1               5                   10                  15

Cys Ala Ala Glu Leu Val Cys Lys Glu Trp Tyr Arg Val Thr Ser Asp
            20                  25                  30

Gly Met Leu Trp Lys Lys
        35

<210> SEQ ID NO 15
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 15

Asp Asp Arg His Asp Ser Gly Leu
1               5

<210> SEQ ID NO 16
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 16

Arg Ser Arg His Ser Ser Tyr Pro
1               5

<210> SEQ ID NO 17
<211> LENGTH: 8
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 17

Leu Ser Arg Lys Ala Ser Ala Val
1               5

<210> SEQ ID NO 18
<211> LENGTH: 8
<212> TYPE: PRT
<213> ORGANISM: Homo sapiens
<220> FEATURE:
<221> NAME/KEY: MOD_RES
<222> LOCATION: (3)..(3)
```

```
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION

<400> SEQUENCE: 18

Leu Ser Arg Ser Ser Ser Gly Tyr
1               5

<210> SEQ ID NO 19
<211> LENGTH: 19
<212> TYPE: RNA
<213> ORGANISM: Homo sapiens

<400> SEQUENCE: 19
aucaagauca gggauaaaa                                                  19

<210> SEQ ID NO 20
<211> LENGTH: 19
<212> TYPE: RNA
<213> ORGANISM: Mus musculus

<400> SEQUENCE: 20
aucaagauca gggauaaaa                                                  19

<210> SEQ ID NO 21
<211> LENGTH: 21
<212> TYPE: RNA
<213> ORGANISM: Homo sapiens

<400> SEQUENCE: 21
cccaacauca ucacucugaa a                                               21

<210> SEQ ID NO 22
<211> LENGTH: 21
<212> TYPE: RNA
<213> ORGANISM: Homo sapiens

<400> SEQUENCE: 22
agcgcugaga auggacagca a                                               21

<210> SEQ ID NO 23
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 23

Arg Ser Ser Ser Gly Tyr Phe Ser Phe Asp
1               5                   10

<210> SEQ ID NO 24
```

```
<211> LENGTH: 13
<212> TYPE: PRT
<213> ORGANISM: Homo sapiens

<400> SEQUENCE: 24

Cys Leu Ser Arg Ser Ser Ser Gly Tyr Phe Ser Phe Asp
1               5                   10

<210> SEQ ID NO 25
<211> LENGTH: 13
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 25

Cys Leu Ser Arg Ser Ser Ser Gly Tyr Phe Ser Phe Asp
1               5                   10

<210> SEQ ID NO 26
<211> LENGTH: 735
<212> TYPE: PRT
<213> ORGANISM: Homo sapiens

<400> SEQUENCE: 26

Met Pro Leu Ala Gln Leu Lys Glu Pro Trp Pro Leu Met Glu Leu Val
1               5                   10                  15

Pro Leu Asp Pro Glu Asn Gly Gln Thr Ser Gly Glu Glu Ala Gly Leu
                20                  25                  30

Gln Pro Ser Lys Asp Glu Gly Val Leu Lys Glu Ile Ser Ile Thr His
            35                  40                  45

His Val Lys Ala Gly Ser Glu Lys Ala Asp Pro Ser His Phe Glu Leu
    50                  55                  60

Leu Lys Val Leu Gly Gln Gly Ser Phe Gly Lys Val Phe Leu Val Arg
65                  70                  75                  80

Lys Val Thr Arg Pro Asp Ser Gly His Leu Tyr Ala Met Lys Val Leu
                85                  90                  95

Lys Lys Ala Thr Leu Lys Val Arg Asp Arg Val Arg Thr Lys Met Glu
            100                 105                 110

Arg Asp Ile Leu Ala Asp Val Asn His Pro Phe Val Val Lys Leu His
        115                 120                 125

Tyr Ala Phe Gln Thr Glu Gly Lys Leu Tyr Leu Ile Leu Asp Phe Leu
    130                 135                 140

Arg Gly Gly Asp Leu Phe Thr Arg Leu Ser Lys Glu Val Met Phe Thr
145                 150                 155                 160

Glu Glu Asp Val Lys Phe Tyr Leu Ala Glu Leu Ala Leu Gly Leu Asp
                165                 170                 175

His Leu His Ser Leu Gly Ile Ile Tyr Arg Asp Leu Lys Pro Glu Asn
            180                 185                 190

Ile Leu Leu Asp Glu Glu Gly His Ile Lys Leu Thr Asp Phe Gly Leu
        195                 200                 205

Ser Lys Glu Ala Ile Asp His Glu Lys Lys Ala Tyr Ser Phe Cys Gly
```

```
               210                 215                 220
Thr Val Glu Tyr Met Ala Pro Glu Val Val Asn Arg Gln Gly His Ser
225                 230                 235                 240

His Ser Ala Asp Trp Ser Tyr Gly Val Leu Met Phe Glu Met Leu
            245                 250                 255

Thr Gly Ser Leu Pro Phe Gln Gly Lys Asp Arg Lys Glu Thr Met Thr
            260                 265                 270

Leu Ile Leu Lys Ala Lys Leu Gly Met Pro Gln Phe Leu Ser Thr Glu
            275                 280                 285

Ala Gln Ser Leu Leu Arg Ala Leu Phe Lys Arg Asn Pro Ala Asn Arg
290                 295                 300

Leu Gly Ser Gly Pro Asp Gly Ala Glu Glu Ile Lys Arg His Val Phe
305                 310                 315                 320

Tyr Ser Thr Ile Asp Trp Asn Lys Leu Tyr Arg Arg Glu Ile Lys Pro
                325                 330                 335

Pro Phe Lys Pro Ala Val Ala Gln Pro Asp Asp Thr Phe Tyr Phe Asp
            340                 345                 350

Thr Glu Phe Thr Ser Arg Thr Pro Lys Asp Ser Pro Gly Ile Pro Pro
            355                 360                 365

Ser Ala Gly Ala His Gln Leu Phe Arg Gly Phe Ser Phe Val Ala Thr
            370                 375                 380

Gly Leu Met Glu Asp Asp Gly Lys Pro Arg Ala Pro Gln Ala Pro Leu
385                 390                 395                 400

His Ser Val Val Gln Gln Leu His Gly Lys Asn Leu Val Phe Ser Asp
                405                 410                 415

Gly Tyr Val Val Lys Glu Thr Ile Gly Val Gly Ser Tyr Ser Glu Cys
                420                 425                 430

Lys Arg Cys Val His Lys Ala Thr Asn Met Glu Tyr Ala Val Lys Val
            435                 440                 445

Ile Asp Lys Ser Lys Arg Asp Pro Ser Glu Glu Ile Glu Ile Leu Leu
450                 455                 460

Arg Tyr Gly Gln His Pro Asn Ile Ile Thr Leu Lys Asp Val Tyr Asp
465                 470                 475                 480

Asp Gly Lys His Val Tyr Leu Val Thr Glu Leu Met Arg Gly Gly Glu
                485                 490                 495

Leu Leu Asp Lys Ile Leu Arg Gln Lys Phe Phe Ser Glu Arg Glu Ala
            500                 505                 510

Ser Phe Val Leu His Thr Ile Gly Lys Thr Val Glu Tyr Leu His Ser
            515                 520                 525

Gln Gly Val Val His Arg Asp Leu Lys Pro Ser Asn Ile Leu Tyr Val
530                 535                 540

Asp Glu Ser Gly Asn Pro Glu Cys Leu Arg Ile Cys Asp Phe Gly Phe
545                 550                 555                 560

Ala Lys Gln Leu Arg Ala Glu Asn Gly Leu Leu Met Thr Pro Cys Tyr
                565                 570                 575

Thr Ala Asn Phe Val Ala Pro Glu Val Leu Lys Arg Gln Gly Tyr Asp
            580                 585                 590

Glu Gly Cys Asp Ile Trp Ser Leu Gly Ile Leu Leu Tyr Thr Met Leu
            595                 600                 605

Ala Gly Tyr Thr Pro Phe Ala Asn Gly Pro Ser Asp Thr Pro Glu Glu
            610                 615                 620

Ile Leu Thr Arg Ile Gly Ser Gly Lys Phe Thr Leu Ser Gly Gly Asn
625                 630                 635                 640
```

```
Trp Asn Thr Val Ser Glu Thr Ala Lys Asp Leu Val Ser Lys Met Leu
                645                 650                 655

His Val Asp Pro His Gln Arg Leu Thr Ala Lys Gln Val Leu Gln His
            660                 665                 670

Pro Trp Val Thr Gln Lys Asp Lys Leu Pro Gln Ser Gln Leu Ser His
        675                 680                 685

Gln Asp Leu Gln Leu Val Lys Gly Ala Met Ala Ala Thr Tyr Ser Ala
    690                 695                 700

Leu Asn Ser Ser Lys Pro Thr Pro Gln Leu Lys Pro Ile Glu Ser Ser
705                 710                 715                 720

Ile Leu Ala Gln Arg Arg Val Arg Lys Leu Pro Ser Thr Thr Leu
                725                 730                 735

<210> SEQ ID NO 27
<211> LENGTH: 3199
<212> TYPE: DNA
<213> ORGANISM: Homo sapiens

<400> SEQUENCE: 27
gccgaagtgc tagtgccgcg gcggcggcgg cggacggccc agccggagcg cgaggggctc      60 ggggggggcgc ggcggttcgg gtcgcagagc cagggacccc aggacccggg aggcggcgca     120
gccggggccg ccggaggagc gcgggtgacc tggcggcggc gagatgccgc tcgcccagct     180
caaggagccc tggccgctca tggagctagt gcctctggac ccggagaatg acagacctc      240 aggggaagaa gctggacttc agccgtccaa ggatgagggc gtcctcaagg agatctccat     300
cacgcaccac gtcaaggctg ctctgagaa ggctgatcca tcccatttcg agctcctcaa      360
ggttctgggc cagggatcct ttggcaaagt cttcctggtg cggaaagtca cccggcctga     420
cagtgggcac ctgtatgcta tgaaggtgct gaagaaggca acgctgaaag tacgtgaccg     480
cgtccggacc aagatggaga gagacatcct ggctgatgta aatcacccat cgtggtgaa     540 gctgcactat gccttccaga ccgagggcaa gctctatctc attctggact tcctgcgtgg     600 tgggacctc ttcacccggc tctcaaaaga ggtgatgttc acggaggagg atgtgaagtt     660
ttacctggcc gagctggctc tgggcctgga tcacctgcac agcctgggta tcatttacag     720
agacctcaag cctgagaaca tccttctgga tgaggagggc cacatcaaac tcactgactt     780
tggcctgagc aaagaggcca ttgaccacga agaagaaggcc tattcttctc tgcgggacagt     840 ggagtacatg gcccctgagg tcgtcaaccg ccagggccac tcccatagtg cggactggtg     900
gtcctatggg gtgttgatgt tgagatgct gacgggctcc ctgccctcc aggggaagga      960 ccggaaggag accatgacac tgattctgaa ggcgaagcta ggcatgcccc agtttctgag    1020
cactgaagcc cagagcctct tgcgggccct gttcaagcgg aatcctgcca accggctcgg    1080
ctccggccct gatggggcag aggaaatcaa gcggcatgtc ttctactcca ccattgactg    1140
gaataagcta taccgtcgtg agatcaagcc acccttcaag ccagcagtgg ctcagcctga    1200
tgacaccttc tactttgaca ccgagttcac gtcccgcaca cccaaggatt ccccaggcat    1260
cccccccagc gctggggccc atcagctgtt ccggggcttc agcttcgtgg ccaccggcct    1320
gatggaagac gacggcaagc tcgtgccccc gcaggcaccc ctgcactcgg tggtacagca    1380
actccatggg aagaacctgg tttttagtga cggctacgtg gtaaaggaga caattggtgt    1440
gggctcctac tctgagtgca gcgctgtgt ccacaaggcc accaacatgg agtatgctgt    1500
caaggtcatt gataagagca agcgggatc ttcagaagag attgagattc ttctgcggta    1560
tggccagcac cccaacatca tcactctgaa agatgtgtat gatgatggca aacacgtgta    1620
```

```
cctggtgaca gagctgatgc ggggtgggga gctgctggac aagatcctgc ggcagaagtt    1680
cttctcagag cgggaggcca gctttgtcct gcacaccatt ggcaaaactg tggagtatct    1740
gcactcacag ggggttgtgc acagggacct gaagcccagc aacatcctgt atgtggacga    1800
gtccgggaat cccgagtgcc tgcgcatctg tgactttggt tttgccaaac agctgcgggc    1860
tgagaatggg ctcctcatga caccttgcta cacagccaac tttgtggcgc ctgaggtgct    1920
gaagcgccag ggctacgatg aaggctgcga catctggagc ctgggcattc tgctgtacac    1980
catgctggca ggatatactc catttgccaa cggtcccagt gacacaccag aggaaatcct    2040
aacccggatc ggcagtggga agtttaccct cagtggggga aattggaaca cagtttcaga    2100
gacagccaag gacctggtgt ccaagatgct acacgtggat ccccaccagc gcctcacagc    2160
taagcaggtt ctgcagcatc catgggtcac ccagaaagac aagcttcccc aaagccagct    2220
gtcccaccag gacctacagc ttgtgaaggg agccatggct gccacgtact ccgcactcaa    2280
cagctccaag cccaccccccc agctgaagcc catcgagtca tccatcctgg cccagcggcg    2340
agtgaggaag ttgccatcca ccaccctgtg aggcaccagg gcattcgggc cacagggcgg    2400
tgctagcttg acacagtcag catgcttccc agagggagca ggccggaacc acagggccag    2460
agggagctgg aacccgaggg gccggggaag ctgccagccc agaacacccc taatgagggt    2520
gtgagaagtg ccttctcctt ccccaggatg gactcttctc ggctcaggct ctgctggtgg    2580
aaagcgattc actgtataaa cttttttta tgaaaaaat ggcatcaacc accatggatt     2640
tttacaagat ccatttgcct ttctgggagc agaaacagcc attgcggccc caggagggga    2700
actgagtcac gctggggctc tctgagactc tttagagcag ctttgggatc ccaccctggg    2760 gaccccacg attggccacc tgtagccatc tgcacacacc tccgagacag tccagtgtca    2820
cctctctcag agcatctggc tgtttagcag aactcattct atcccaatc agctcctttt    2880 ccgttctgtt ctgctgggag ttctagaacc acttcctgct acaggagggg tctcatgtcc    2940
tgctggcttc cagcttcagg caccagcatc caccttggct ctgccagtgg atcccctgcg    3000
gtcaggctgg gcagcccag agagaggatg tggaaagcac ttttggctg acttcatctg     3060 gggttggcaa caggacagag ttcacaggag gccagtgggc gggccatgag ggacagggtc    3120 tttttttcatt tcttcctcag ctggttactc agggttcatc tgtccatggc ctttctaata    3180
aactgttgag ttgaagcac                                                 3199
```

<210> SEQ ID NO 28
<211> LENGTH: 19
<212> TYPE: DNA
<213> ORGANISM: Artificial Sequence
<220> FEATURE:
<223> OTHER INFORMATION: control oligonucleotide

<400> SEQUENCE: 28
cguacgcgga auacuucga                                                  19

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ggcattgcct gtttgcagta                                                 20

<210> SEQ ID NO 30

-continued

```
<211> LENGTH: 20
<212> TYPE: DNA
<213> ORGANISM: Artificial Sequence
<220> FEATURE:
<223> OTHER INFORMATION: primer

<400> SEQUENCE: 30
gcaccacatt ctatgtccca                                                 20
```